(12) United States Patent
Okiyama et al.

(10) Patent No.: US 10,596,068 B2
(45) Date of Patent: Mar. 24, 2020

(54) DRUG CONTAINER CONNECTOR AND MALE MEMBER COVER

(71) Applicant: JMS CO., LTD., Hiroshima-shi, Hiroshima (JP)

(72) Inventors: Tadashi Okiyama, Hiroshima (JP); Hidetoshi Kato, Hiroshima (JP); Masahiko Takeuchi, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 447 days.

(21) Appl. No.: 15/303,700

(22) PCT Filed: Apr. 30, 2015

(86) PCT No.: PCT/JP2015/063005
§ 371 (c)(1),
(2) Date: Oct. 12, 2016

(87) PCT Pub. No.: WO2015/166993
PCT Pub. Date: Nov. 5, 2015

(65) Prior Publication Data
US 2017/0027820 A1   Feb. 2, 2017

(30) Foreign Application Priority Data

| May 2, 2014 | (JP) | ................................ | 2014-095348 |
| May 2, 2014 | (JP) | ................................ | 2014-095349 |
| Jan. 14, 2015 | (JP) | ................................ | 2015-005316 |

(51) Int. Cl.
*A61J 1/20* (2006.01)
*A61J 1/14* (2006.01)
(Continued)

(52) U.S. Cl.
CPC .............. *A61J 1/201* (2015.05); *A61J 1/065* (2013.01); *A61J 1/1406* (2013.01); *A61J 1/1481* (2015.05);
(Continued)

(58) Field of Classification Search
CPC ........ A61J 1/201; A61J 1/1481; A61J 1/1487; A61J 1/2044; A61J 1/2055; A61J 1/2065;
(Continued)

(56) References Cited

U.S. PATENT DOCUMENTS 4,576,211 A * 3/1986 Valentini ............... A61J 1/2096
141/329
2008/0300536 A1   12/2008 Wang et al.
(Continued)

FOREIGN PATENT DOCUMENTS

| CA | 2 785 130 | 2/2014 |
| EP | 2 939 648 | 11/2015 |

(Continued)

OTHER PUBLICATIONS

Office Action issued in corresponding Japanese Application No. 2015-005316, dated Oct. 2, 2018, 12 pages with translation.
(Continued)

*Primary Examiner* — Adam Marcetich
*Assistant Examiner* — Jessica R Arble
(74) *Attorney, Agent, or Firm* — Hamre, Schumann, Mueller & Larson, P.C.

(57) ABSTRACT

A drug container connector (1) is provided with a puncture needle (20) capable of puncturing a plug (186) that seals a mouth (183) of a container (180); and a cover (90) that covers an opening, on a tip side, of a flow channel (21) formed in the puncture needle (20). The puncture needle (20) is configured to penetrate the cover (90) and puncture the plug (186). The puncture needle (20) is provided on a connector main body (10). The cover (90) is held by a slider (50). The slider (90) is movable with respect to the connector main body (10) in a longitudinal direction of the puncture
(Continued)

needle (20). The slider (50) is provided with claws (66, 76) capable of engaging with a flange (182) at the mouth of the container (180).

22 Claims, 45 Drawing Sheets

(51) Int. Cl.
    *A61M 39/10*     (2006.01)
    *A61J 1/06*     (2006.01)
    *A61M 39/20*     (2006.01)

(52) U.S. Cl.
    CPC ........... *A61J 1/1487* (2015.05); *A61J 1/2044* (2015.05); *A61J 1/2055* (2015.05); *A61J 1/2065* (2015.05); *A61M 39/1011* (2013.01); *A61M 39/20* (2013.01); *A61M 2039/1027* (2013.01); *A61M 2039/1072* (2013.01)

(58) Field of Classification Search
    CPC .... A61J 1/065; A61J 1/1406; A61M 39/1011; A61M 39/20; A61M 2039/1026; A61M 2039/1072
    See application file for complete search history.

(56) References Cited

U.S. PATENT DOCUMENTS

| | | | | |
|---|---|---|---|---|
| 2009/0069783 | A1* | 3/2009 | Ellstrom | A61M 39/10 604/415 |
| 2010/0168712 | A1 | 7/2010 | Tuckwell et al. | |
| 2010/0218846 | A1* | 9/2010 | Kriheli | A61J 1/2096 141/5 |
| 2014/0021714 | A1 | 1/2014 | Ueda et al. | |
| 2014/0114292 | A1* | 4/2014 | Tachizaki | F16L 37/30 604/535 |
| 2015/0083950 | A1 | 3/2015 | Okiyama | |
| 2015/0265499 | A1 | 9/2015 | Takeuchi | |
| 2015/0359709 | A1* | 12/2015 | Kriheli | A61J 1/2072 604/405 |

FOREIGN PATENT DOCUMENTS

| | | |
|---|---|---|
| JP | 2001-511056 | 8/2001 |
| JP | 2008-110802 | 5/2008 |
| JP | 2008-523851 | 7/2008 |
| JP | 2012-135439 | 7/2012 |
| JP | 2012-254142 | 12/2012 |
| JP | 2015-066067 | 4/2015 |
| WO | 39/27886 | 6/1999 |
| WO | 2012/128321 | 9/2012 |
| WO | 2013/161979 | 10/2013 |
| WO | 2013/175970 | 11/2013 |
| WO | 2014/041529 | 3/2014 |

OTHER PUBLICATIONS

Office Action issued in corresponding Japanese Patent Application No. 2014-095348, dated Dec. 19, 2017, 8 pages with translation.
Search Report and Written Opinion issued in corresponding Singaporean Patent Application No. 11201609142W, dated Sep. 20, 2017, 10 pages.

* cited by examiner

DRUG CONTAINER CONNECTOR AND MALE MEMBER COVER

TECHNICAL FIELD

The present invention relates to a connector that is to be connected to a closed drug container such as a vial bottle. Furthermore, the present invention relates to a male member cover capable of being mounted to a male member that is to be inserted into (including "to puncture") a female member.

BACKGROUND ART

Closed drug containers such as vial bottles generally contain a powdered medicine. When administering the medicine to a patient, a dissolving solution is injected into the vial bottle to dissolve the medicine and obtain a drug solution, and then the drug solution is taken out of the vial bottle. In general, the taken-out drug solution is temporarily accumulated in a drug solution bag.

The medicine contained in the vial bottle may be a medicine designated as, for example, a dangerous drug such as an anticancer drug. It is necessary to prevent such a situation that a drug solution including such a dangerous medicine leaks and is attached to a finger or the like of an operator, or that the operator inhales vapor thereof. Accordingly, the above-described series of operations of dissolving the medicine in the vial bottle, and transporting the drug solution to the drug solution bag are desired to be carried out using a "closed system device" from which the drug solution is unlikely to leak.

An example of such a closed system device is disclosed in Patent Document 1. The device of Patent Document 1 (that is referred to as "medical connector" in Patent Document 1) is provided with two connectors to which a vial bottle and a drug solution bag are respectively connected, and with a port to which a syringe is connected. The device is further provided with a cock for switching flow channels between the vial bottle, the drug solution bag, and the syringe. The vial bottle, the drug solution bag, and the syringe are connected to the device. A dissolving solution for dissolving a medicine is stored in the drug solution bag in advance. By operating the cock to switch the flow channels appropriately, it is possible to transport the dissolving solution in the drug solution bag to the vial bottle via the syringe, dissolve the medicine in the vial bottle to obtain a drug solution, and then transport the drug solution in the vial bottle to the drug solution bag via the syringe. The vial bottle is replaced by a new vial bottle and the same operation is performed, if the need arises. Accordingly, drug solutions that are obtained by dissolving medicines in the required number and types of vial bottles can be accumulated in common drug solution bags.

The mouth (opening) of the vial bottle is generally sealed by a plug (rubber plug). The connector of the device to which the vial bottle is connected is provided with a puncture needle that has a sharp tip and is to puncture this plug. The drug solution remaining in the flow channel of the puncture needle may leak to the outside from the opening, on a tip side, of the flow channel of the puncture needle after the vial bottle and the connector are separated from each other.

Patent Document 2 discloses a flexible cover (shield) configured to cover a rod-shaped male member (male luer) that is to be inserted into a female member (needle-less port). The cover is provided with a compressible and deformable outer circumferential wall in the shape of an accordion, a head portion that is provided at one end of the outer circumferential wall and into which the tip of the male member is inserted, and a base portion that is provided at the other end of the outer circumferential wall. The base portion of the cover is fixed to a base substrate that holds the male member. The female member is provided with a partition wall member (generally referred to as "septum") that is made of an elastic material such as rubber in which a linear slit (incision) is formed. When connecting the male member and the female member to each other, the male member penetrates the cover, and is further inserted into the slit of the septum. At this time, the outer circumferential wall of the cover is elastically compressed. When the male member has been separated from the female member, the outer circumferential wall of the cover reverts to an initial shape, and covers the male member.

By applying the cover of Patent Document 2 to the puncture needle of the above-described device, it is conceivable that a drug solution can be prevented from leaking from the puncture needle to the outside after the vial bottle and the connector are separated from each other.

PRIOR ART DOCUMENTS

Patent Document

[Patent Document 1] WO 2013/161979
[Patent Document 2] JP 2012-254142A

DISCLOSURE OF INVENTION

Problem to be Solved by the Invention

However, when the cover of Patent Document 2 is actually applied to the puncture needle of the device of Patent Document 1, there is a case where the outer circumferential wall of the cover does not immediately revert to the initial shape after the vial bottle and the connector are separated from each other. In this case, the opening, on the tip side, of the flow channel of the puncture needle is exposed to the outside, and thus the drug solution remaining in the flow channel will leak from the opening.

Patent Document 2 discloses that the tip of the head portion of the cover has an engaging shape so as to be able to engage with a female member, in order to help the outer circumferential wall of the cover revert to the initial shape. However, vial bottles do not generally have a shape with which the engaging shape of the cover can engage.

Furthermore, there may be a case where the cover of Patent Document 2 is not in sufficient intimate contact with the plug when the puncture needle is punctures the plug. If the cover is not favorably in intimate contact with the plug, and the cover and the plug are then separated from each other, a large amount of a drug solution will be attached to surfaces of the cover and the plug.

The present invention was made in order to solve the above-described problems. It is a first object of the present invention to reduce, in a connector in which a puncture needle for puncturing a plug of a container typified by a vial bottle is covered by a cover, the likelihood of a drug solution leaking to the outside after the connector and the container are separated from each other. It is a second object of the present invention to improve the intimate contact between the cover and a female member (for example, the plug) so as to reduce the amount of a drug solution that is to be attached to surfaces of the cover and the female member after the cover and the female member are separated from each other.

Means for Solving Problem

According to the present invention, a drug container connector includes: a puncture needle capable of puncturing a plug that seals a mouth of a container; and a cover that covers an opening, on a tip side, of a flow channel through which liquid flows and that is formed in the puncture needle, the puncture needle being configured to penetrate the cover and puncture the plug. The puncture needle is provided on a connector main body. The cover is held by a slider. The slider is movable with respect to the connector main body in a longitudinal direction of the puncture needle. The slider is provided with a claw capable of engaging with a flange at the mouth of the container.

According to the present invention, a male member cover covers an opening, on a tip side, of a flow channel of a male member through which liquid flows, and is configured to be penetrated by the male member when the male member is inserted into a female member. The cover includes: a seal region that comes in intimate contact with an outer circumferential surface of the male member; a deformable region that is arranged on a tip side relative to the seal region; a slit that is provided at a tip of the deformable region so as to be penetrated by the male member; and a hold portion that is to be used for the cover to be held. The deformable region is more easily subjected to compression deformation and stretching deformation in a longitudinal direction of the male member than the seal region. A closed space is formed in the deformable region in an initial state in which the cover is distanced from the female member. The hold portion is provided in the seal region.

Effect of the Invention

According to the drug container connector of the present invention, the slider that is movable with respect to the connector main body provided with the puncture needle holds the cover, and is provided with the claw capable of engaging with the flange of the container. Accordingly, when drawing the puncture needle from the plug, the opening, on the tip side, of the flow channel of the puncture needle can be covered by the cover without being exposed to the outside. Accordingly, it is possible to reduce the likelihood of a drug solution leaking to the outside after the connector and the container are separated from each other.

The male member cover of the present invention includes, on a tip side relative to the seal region, the deformable region that can be subjected relatively easily to compression deformation and stretching deformation. The hold portion that is to be used for the cover to be held is provided in the seal region. Accordingly, the deformable region selectively deforms depending on deformation or a difference in the outer size of the female member. Therefore, the intimate contact between the cover and the female member is favorable. The cover that is in intimate contact with the female member prevents a drug solution from leaking via the female member.

Furthermore, the closed space is formed in the deformable region in the initial state in which the cover is distanced from the female member. When the deformable region is compressed/stretched, the atmospheric pressure in the closed space changes. By generating negative pressure in the closed space, it is possible to suction the drug solution into the closed space via the slit.

As a result, according to the male member cover of the present invention, it is possible to reduce the amount of a drug solution that is attached to surfaces of the cover and the female member after the cover and the female member are separated from each other.

The male member cover of the present invention can be mounted to a male member provided on a connector. According to the connector having such a configuration, since the intimate contact between the cover and the female member is favorable, it is possible to reduce the amount of a drug solution that is attached to surfaces of the cover and the female member after the connector and the female member are separated from each other.

DESCRIPTION OF THE INVENTION

Figure 1:
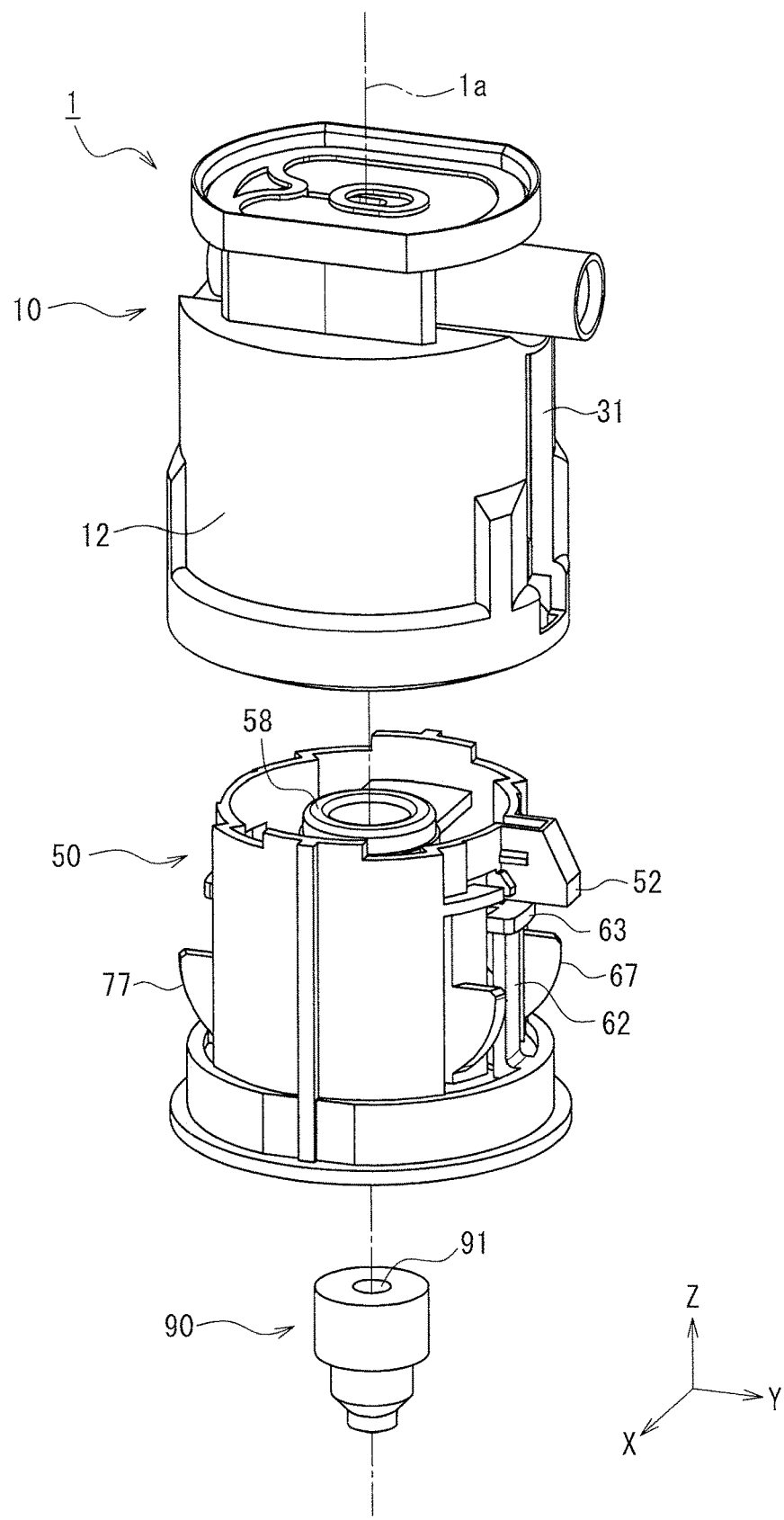
FIG. 1 is an exploded perspective view of a connector according to Embodiment 1 of the present invention.

According to the present invention, a drug container connector includes: a puncture needle capable of puncturing a plug that seals a mouth of a container; and a cover that covers an opening, on a tip side, of a flow channel through which liquid flows and that is formed in the puncture needle, the puncture needle being configured to penetrate the cover and puncture the plug. The puncture needle is provided on a connector main body. The cover is held by a slider. The slider is movable with respect to the connector main body in a longitudinal direction of the puncture needle. The slider is provided with a claw capable of engaging with a flange at the mouth of the container.

Preferably, the above-described drug container connector of the present invention is configured such that a tip of the cover abuts against the plug in a state in which the claw is engaged with the flange of the container. Accordingly, as long as the claw is engaged with the flange, the opening, on the tip side, of the flow channel of the puncture needle is reliably stored in the cover without being exposed to the outside when the puncture needle is drawn from the plug. Therefore, it is possible to reduce the likelihood of a drug solution leaking to the outside after the connector and the container are separated from each other.

Preferably, the above-described drug container connector of the present invention further includes a lock mechanism for preventing disengagement between the claw and the flange. Accordingly, it is possible to prevent an erroneous operation in which the claw and the flange are unintentionally disengaged from each other.

The lock mechanism may include: a grip arm on which the claw is formed and that can elastically bend and deform outwardly (that is, in a direction away from the puncture needle); and the connector main body for restricting bending and deformation of the grip arm. Accordingly, it is possible to configure the lock mechanism with a simple configuration.

Preferably, a locked state and an unlocked state of the lock mechanism can be switched based on a position of the slider with respect to the connector main body in the longitudinal direction of the puncture needle. Accordingly, in a process in which, for example, the puncture needle punctures the plug, a configuration is possible in which the lock mechanism automatically switches from the unlocked state to the locked state at the same time as when the slider is moved toward the connector main body. Accordingly, it is possible to prevent an erroneous operation in which the claw and the flange are unintentionally disengaged from each other due to the lock mechanism not being switched to the locked state.

The above-described drug container connector of the present invention may be configured such that the lock mechanism does not function when the slider is drawn, to the maximum, from the connector main body. Accordingly, only by moving the container in a punctured state in which the puncture needle has punctured the plug away from the connector main body in one direction, it is possible to achieve the state in which the connector and the container can be separated from each other. Accordingly, the operation of separating the connector from the container is simplified, and it is easy for a non-skilled person to understand the separating operation.

In a process of drawing the slider from the connector main body toward an unlocked position at which the lock mechanism does not function, an intermediate stop position at which movement of the slider with respect to the connector main body is restricted so that the slider cannot be further drawn from the connector main body may be provided at a position prior to the unlocked position. Accordingly, the operation of separating the connector from the container is temporarily stopped at the intermediate stop position. Thus, the length of time in which the hole of the plug that the puncture needle has punctured closes is reliably ensured. Accordingly, thereafter, when the cover is separated from the plug, it is possible to reduce the likelihood of a drug solution leaking from the plug.

A release button for releasing the restriction of the movement of the slider with respect to the connector main body at the intermediate stop position may be provided. It is not possible to move the slider to the unlocked position unless the release button is pressed. Accordingly, the operation of separating the connector from the container is reliably stopped at the intermediate stop position. Thus, the length of time in which the hole of the plug that the puncture needle has punctured closes is reliably ensured. Accordingly, thereafter, when the cover is separated from the plug, it is possible to reduce the likelihood of a drug solution leaking from the plug.

Preferably, the opening of the puncture needle is covered by the cover when the slider is located at the unlocked position at which the lock mechanism does not function. Accordingly, even if the claw and the flange are disengaged when the slider is at the unlocked position, it is possible to prevent the occurrence of a situation in which a drug solution leaks to the outside from the opening, on the tip side, of the liquid flow channel.

Preferably, the above-described drug container connector of the present invention is configured such that the slider cannot move with respect to the connector main body in the longitudinal direction of the puncture needle when the claw is not engaged with the flange of the container. Accordingly, even by applying a compression force for causing the claw to engage with the flange of the container to the connector main body instead of the slider, the slider does not move with respect to the connector main body. Accordingly, the operation of mounting the connector to the container can be performed efficiently. Furthermore, it is possible to prevent an erroneous operation in which the slider and the connector main body are separated from each other by mistake.

Preferably, the above-described drug container connector of the present invention is configured such that the slider can move with respect to the connector main body in the longitudinal direction of the puncture needle when the claw is engaged with the flange of the container. Accordingly, it is possible to move the container engaged with the claw toward the connector main body and to cause the puncture needle to puncture the plug. Furthermore, in the state in which the puncture needle has punctured the plug, it is possible to move the container engaged with the claw in a direction away from the connector main body, and to draw the puncture needle from the plug.

In the above-described drug container connector of the present invention, the slider may include: an abutting protrusion that abuts against an upper edge of the plug when the claw is engaged with the flange of the container; and a slide restricting arm on which the abutting protrusion is formed and that can elastically bend and deform outwardly (that is, in a direction away from the puncture needle). Accordingly, it is possible to hold the flange and the plug of the container, using the claw and the abutting protrusion. Furthermore, since the abutting protrusion is formed on the bendable and deformable slide restricting arm, acceptable ranges for the sizes of the flange and the plug to which the connector can be mounted increase.

Preferably, when the claw is not engaged with the flange of the container, the slide restricting arm collides with the connector main body, so as to restrict the slider from moving with respect to the connector main body in the longitudinal direction of the puncture needle. Furthermore, preferably, when the claw is engaged with the flange of the container, the slide restricting arm elastically bends and deforms to a position at which the slide restricting arm does not collide with the connector main body, so as to enable the slider to move with respect to the connector main body in the longitudinal direction of the puncture needle. Accordingly, when the claw is not engaged with the flange, a compression force toward the container can be applied to the connector main body so that the claw can engage with the flange. Once the claw is engaged with the flange, a compression force toward the container can be applied to the connector main body so that the puncture needle punctures the plug. Accordingly, by only applying a compression force toward the container to the connector main body, the state in which the claw is not engaged with the flange can continuously shift to the state in which the puncture needle has punctured the plug. Moreover, this can be realized with a simple configuration.

Preferably, the edge of the abutting protrusion that abuts against the plug is inclined with respect to the longitudinal direction of the puncture needle. Accordingly, acceptable ranges for the sizes of the flange and the plug to which the connector can be mounted increase.

In the above-described drug container connector of the present invention, the cover may be provided with: a slit through which the puncture needle can penetrate and that is provided at a tip of the cover; a seal region that is in intimate contact with an outer circumferential surface of the puncture needle; and a deformable region that is arranged on the tip side relative to the seal region. In this case, preferably, the deformable region is more easily subjected to compression deformation and stretching deformation in the longitudinal direction of the puncture needle than the seal region. Accordingly, the deformable region can deform conforming to deformation of the plug. Thus, the state in which the tip of the cover is in intimate contact with the plug can be kept regardless of the position of the slider with respect to the connector main body, as long as the claw is engaged with the flange of the container. As a result, it is possible to reduce the amount of a drug solution that is attached to the tip of the cover and the outer surface of the plug after the cover and the plug are separated from each other. Furthermore, it is possible to reduce the amount of a drug solution leaking to the outside, even for containers having different sizes.

Preferably, a closed space is formed in the deformable region when the claw is not engaged with the flange of the container. Accordingly, it is possible to accumulate a drug solution in the closed space. This is advantageous for reducing the amount of a drug solution leaking to the outside.

Preferably, the closed space is reduced or has disappeared when the puncture needle has penetrated the plug. When the puncture needle is drawn from the plug, and the claw and the flange are then disengaged from each other, the reduced or disappearing space then reverts to the initial shape. In this reverting process, negative pressure is generated in this space. A drug solution between the tip of the cover and the plug is suctioned, with the negative pressure, into this space via the slit. Accordingly, it is possible to reduce the amount of a drug solution that is attached to the tip of the cover and the outer surface of the plug after the cover and the plug are separated from each other.

The cover may include a hold portion that is used for the cover to be held to the slider. In this case, preferably, the hold portion is provided in the seal region. Accordingly, the position of the seal region with respect to the slider in the longitudinal direction of the puncture needle is kept as being substantially fixed regardless of the position of the slider with respect to the connector main body. Accordingly, when the puncture needle is drawn from the plug, the opening, on the tip side, of the flow channel of the puncture needle is reliably covered by the cover without being exposed to the outside. Therefore, it is possible to further reduce the likelihood of a drug solution leaking to the outside after the connector and the vial bottle are separated from each other.

Preferably, the above-described drug container connector of the present invention is such that a tip of the cover that is configured to be penetrated by the puncture needle has a projection surface that projects toward the plug. Accordingly, the intimate contact between the tip of the cover and the plug is improved. It is thus possible to further reduce the likelihood of a drug solution leaking to the outside.

Preferably, the above-described drug container connector of the present invention is such that the cover does not have an engaging shape to engage with the container. In the present invention, even if no such an engaging shape is provided, the opening, on the tip side, of the flow channel of the puncture needle is covered by the cover without being exposed to the outside, when the puncture needle is drawn from the plug. Accordingly, for containers that do not have a shape with which the engaging shape engages, it is possible to always reduce the likelihood of a drug solution leaking to the outside.

The slit may be a linear incision. The slider may further include a pair of side walls that are opposite to each other in a direction orthogonal to a longitudinal direction of the slit. In this case, preferably, the pair of side walls compress the deformable region so as to bring a pair of edges forming the slit into intimate contact with each other. Accordingly, the sealing property of the slit is improved, and thus the likelihood of a drug solution stored in the closed space in the deformable region leaking to the outside via the slit is reduced. As a result, it is possible to further reduce the amount of a drug solution that is attached to the surface of the cover after the connector and the container are separated from each other.

The side walls may be able to elastically bend and deform so that a distance between the pair of side walls increases. Accordingly, it is possible to prevent the side walls and the cover from being damaged when the puncture needle penetrates the slit. Furthermore, it is possible to suppress an increase, due to the provision of the side walls, in resistance when the puncture needle penetrates the slit.

Preferably, the slider and the cover may respectively have engaging shapes that engage with each other so as to define a position of the cover in a direction of rotation about the puncture needle. Accordingly, it is easy to perform the operation of mounting the cover to the slider so that the longitudinal direction of the slit is orthogonal to the direction in which the pair of side walls are opposite to each other. The engaging shape on the cover side can be provided on the hold portion in the seal region, and the engaging shape on the slider side can be provided on the holder for holding the hold portion.

According to the present invention, a male member cover covers an opening, on a tip side, of a flow channel of a male member (for example, a puncture needle) through which liquid flows, and is configured to be penetrated by the male member when the male member is inserted into a female member (for example, a plug that seals a mouth of a container). The cover includes: a seal region that comes in intimate contact with an outer circumferential surface of the male member; a deformable region that is arranged on a tip side relative to the seal region; a slit that is provided at a tip of the deformable region so as to be penetrated by the male member; and a hold portion that is to be used for the cover to be held. The deformable region is more easily subjected to compression deformation and stretching deformation in a longitudinal direction of the male member than the seal region. A closed space is formed in the deformable region in an initial state in which the cover is distanced from the female member. The hold portion is provided in the seal region.

In the foregoing male member cover of the present invention, preferably, the closed space is reduced or has disappeared when the puncture needle has inserted into the female member. Accordingly, in the process in which the cover reverts from the state in which the male member was inserted into the female member to the initial state, negative pressure can be generated in the closed space. A drug solution between the cover and the female member is suctioned, with the negative pressure in the closed space, into the closed space via the slit. Accordingly, it is possible to further reduce the amount of the drug solution that is attached to the surfaces of the cover and the female member after the cover and the female member are separated from each other.

Preferably, a projection surface that projects toward a female member is formed at the position on the outer surface of the cover at which the slit is provided. This is advantageous for improving the intimate contact between the tip of the cover and the female member. Accordingly, it is possible to further reduce the amount of a drug solution that is attached to the surfaces of the cover and the female member after the cover and the female member are separated from each other.

The cover does not need to be provided with an engaging shape to engage with the female member. Accordingly, it is not necessary to prepare a plurality of covers having different engaging shapes that correspond to the specifications of female members. The cover of the present invention can reduce the amount of a drug solution that is attached to the surfaces of the cover and a female member (for example, a vial bottle), even if the female member does not have a structure capable of engaging with the engaging shape, after the cover and the female member are separated from each other.

It is possible to configure a connector that is provided with a male member that can be inserted into a female member, and a cover that covers an opening, on the tip side, of a flow channel of the male member through which liquid flows. The connector has a configuration in which the male member penetrates the cover and is inserted into the female member. The cover may be the above-described male member cover of the present invention.

The male member is preferably provided on a connector main body. The hold portion of the cover is preferably held by a slider. The slider is preferably movable with respect to the connector main body in a longitudinal direction of the male member. The slider is preferably provided with a claw capable of engaging with the female member. Accordingly, when the male member is drawn from the female member, the opening, on the tip side, of the flow channel of the male member can be covered by the cover without being exposed to the outside. Accordingly, it is possible to reduce the likelihood of a drug solution leaking to the outside after the connector and the female member are separated from each other.

Preferably, the above-described connector is configured such that the tip of the cover abuts against the female member in the state in which the claw is engaged with the female member. Accordingly, the opening, on the tip side, of the flow channel of the male member is reliably stored in the cover without being exposed to the outside when the male member is drawn from the female member, as long as the claw is engaged with the female member. Therefore, it is possible to reduce the likelihood of a drug solution leaking to the outside after the connector and the female member are separated from each other.

Preferably, the above-described connector includes a lock mechanism for preventing disengagement between the claw and the female member. Accordingly, it is possible to prevent an erroneous operation in which the claw and the female member are unintentionally disengaged from each other.

The lock mechanism may include: a grip arm on which the claw is formed and that can elastically bend and deform outwardly (that is, in a direction away from the male member); and the connector main body for restricting bending and deformation of the grip arm. Accordingly, it is possible to configure the lock mechanism with a simple configuration.

Preferably, a locked state and an unlocked state of the lock mechanism can be switched based on the position of the slider with respect to the connector main body in the longitudinal direction of the male member. Accordingly, in a process in which, for example, the male member is inserted into the female member, a configuration is possible in which the lock mechanism automatically switches from the unlocked state to the locked state at the same time as when the slider is moved toward the connector main body. Accordingly, it is possible to prevent an erroneous operation in which the claw and the female member are unintentionally disengaged from each other due to the lock mechanism not being switched to the locked state.

It is possible to configure such that the lock mechanism does not function when the slider is drawn, to the maximum, from the connector main body. Accordingly, only by moving the female member in the state in which the male member is inserted into the female member (inserted state) away from the connector main body in one direction, it is possible to achieve a state in which the connector and the female member can be separated from each other. Accordingly, the operation of separating the connector from the female member is simplified, and it is easy for a non-skilled person to understand the separating operation.

In a process of drawing the slider from the connector main body toward an unlocked position at which the lock mechanism does not function, an intermediate stop position at which movement of the slider with respect to the connector main body is restricted so that the slider cannot be further drawn from the connector main body may be provided at a position prior to the unlocked position. Accordingly, the operation of separating the connector from the female member is temporarily stopped at the intermediate stop position. Thus, the length of time in which the hole of the female member into which the male member has been inserted closes is reliably ensured. Accordingly, thereafter, when the cover is separated from the female member, it is possible to reduce the likelihood of a drug solution leaking from the female member.

Preferably, a release button for releasing the restriction of the movement of the slider with respect to the connector main body at the intermediate stop position may be provided. It is not possible to move the slider to the unlocked position unless the release button is pressed. Accordingly, the operation of separating the connector from the female member is reliably stopped at the intermediate stop position. Thus, the length of time in which the hole of the female member into which the male member has been inserted closes is reliably ensured. Accordingly, thereafter, when the cover is separated from the female member, it is possible to reduce the likelihood of a drug solution leaking from the female member.

Preferably, the opening of the male member is covered by the cover when the slider is located at the unlocked position at which the lock mechanism does not function. Accordingly, even if the claw and the female member are disengaged when the slider is at the unlocked position, it is possible to prevent the occurrence of a situation in which a drug solution leaks to the outside from the opening, on the tip side, of the flow channel.

Preferably, the above-described connector is configured such that the slider cannot move with respect to the connector main body in the longitudinal direction of the male member when the claw is not engaged with the female member. Even by applying a compression force for causing the claw to engage with the female member to the connector main body instead of the slider, the slider does not move with respect to the connector main body. Accordingly, the operation of mounting the connector to the female member can be performed efficiently. Furthermore, it is possible to prevent an erroneous operation in which the slider and the connector main body are separated from each other by mistake.

Preferably, the above-described connector is configured such that the slider can move with respect to the connector main body in the longitudinal direction of the male member when the claw is engaged with the female member. Accordingly, it is possible to move the female member engaged with the claw toward the connector main body and to insert the male member into the female member. Furthermore, in the state in which the male member is inserted into the female member, it is possible to move the female member engaged with the claw in a direction away from the connector main body, and to draw the male member from the female member.

In the above-described connector, the slider may include: an abutting protrusion that abuts against an upper edge of the female member when the claw is engaged with the female member; and a slide restricting arm on which the abutting protrusion is formed and that can elastically bend and deform outwardly (that is, in a direction away from the male member). Accordingly, it is possible to hold the female member, using the claw and the abutting protrusion. Furthermore, since the abutting protrusion is formed on the bendable and deformable slide restricting arm, an acceptable range for the size of the female member to which the connector can be mounted increases.

Preferably, when the claw is not engaged with the female member, the slide restricting arm collides with the connector main body, so as to restrict the slider from moving with respect to the connector main body in the longitudinal direction of the male member. Furthermore, preferably, when the claw is engaged with the female member, the slide restricting arm elastically bends and deforms to a position at which the slide restricting arm does not collide with the connector main body, so as to enable the slider to move with respect to the connector main body in the longitudinal direction of the male member. Accordingly, when the claw is not engaged with the female member, a compression force toward the female member can be applied to the connector main body so that the claw can engage with the female member. Once the claw is engaged with the female member, a compression force toward the female member can be applied to the connector main body so that the male member is inserted into the female member. Accordingly, by only applying a compression force toward the female member to the connector main body, the state in which the claw is not engaged with the female member can continuously shift to the state in which the male member is inserted into the female member. Moreover, this can be realized with a simple configuration.

Preferably, the edge of the abutting protrusion that is to abut against the female member is inclined with respect to the longitudinal direction of the male member. Accordingly, an acceptable range for the size of the female member to which the connector can be mounted increases.

The female member may be a vial bottle. Furthermore, the male member may be a puncture needle that is provided with a sharp tip capable of puncturing the plug that seals the mouth of the vial bottle. The vial bottle may contain a medicine that is dangerous if it leaks to the outside. According to the connector, it is possible to reduce the leakage of a drug solution to the outside, and the above-described preferred configuration can significantly achieve the effects of present invention.

The slit may be a linear incision. The connector may further include a pair of side walls that are opposite to each other in a direction orthogonal to the longitudinal direction of the slit. In this case, preferably, the pair of side walls compress the deformable region so as to bring a pair of edges forming the slit into intimate contact with each other. Accordingly, the sealing property of the slit is improved, and thus the likelihood of a drug solution stored in the closed space leaking to the outside via the slit is reduced. As a result, it is possible to further reduce the amount of a drug solution that is attached to the surface of the cover after the connector and the female member are separated from each other.

The side walls may be elastically bendable and deformable so that the distance between the pair of side walls increases. Accordingly, it is possible to prevent the side walls and the cover from being damaged when the male member penetrates the slit. Furthermore, it is possible to suppress an increase, due to the provision of the side walls, in resistance when the male member penetrates the slit.

The above-described connector may further include a holder for holding the hold portion of the cover. In this case, the hold portion and the holder may respectively have engaging shapes that engage with each other so as to define a position of the cover in a direction of rotation about the male member. Accordingly, it is easy to perform the operation of mounting the cover to the holder so that the longitudinal direction of the slit is orthogonal to the direction in which the pair of side walls are opposite to each other.

Hereinafter, the present invention will be described in detail with reference to preferred embodiments. Note that the present invention is of course not limited to the embodiments below. For convenience of description, the drawings that are referenced in the description below show, of the members constituting the embodiments of the present invention, only essential members that are necessary for the description of the present invention in a simplified manner. Accordingly, the present invention may include arbitrary members that are not shown in the drawings below.

Embodiment 1

1. Connector Configuration

FIG. 1 is an exploded perspective view of a drug container connector (hereinafter, referred to simply as "connector") 1 according to Embodiment 1 of the present invention. The connector 1 is constituted by a connector main body 10, a slider 50, and a cover (or shield) 90. A long dash-dotted line 1a is a central axis of the connector 1. For convenience of description below, an XYZ orthogonal coordinate system in which an axis parallel to the central axis 1a is set as the Z axis. The "vertical direction" refers to the Z axis direction, and the "upper" side refers to the side to which the Z-axis arrow is oriented, and the "lower" side refers to the side opposite thereto. The "horizontal direction" refers to the direction parallel to the plane orthogonal to the Z axis. The "front" side refers to the side to which the Y-axis arrow is oriented, and the "rear" side refers to the side opposite thereto. The "radial direction" or "diameter direction" refers to the direction along the straight line orthogonal to the central axis 1a, and the "circumferential direction" refers to the direction of rotation about the central axis 1a. In the radial direction, the "outer" side refers to the side away from the central axis 1a, and the "inner" side refers to the side toward the central axis 1a.

The connector 1 can be replaced by a "second connector 200" (see FIGS. 11 to 14 of Patent Document 1) of the above-described Patent Document 1 to which a vial bottle is to be connected, and can constitute a closed system device that functions similar to the device of Patent Document 1. In the present description, the portion of the connector 1 that is relevant to the connection to the vial bottle is mainly described, and description of the remaining portion is omitted.

1.1. Connector Main Body

Figure 2A:
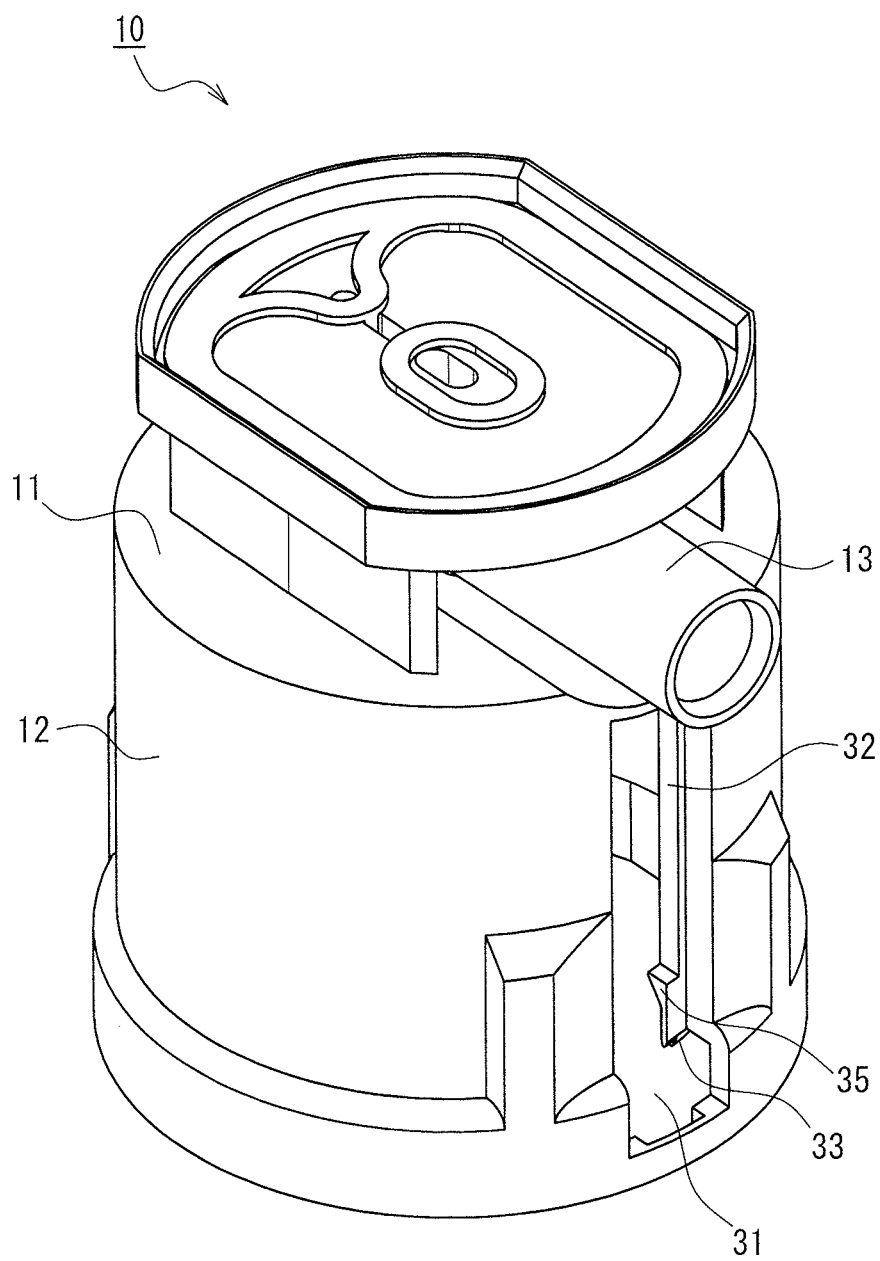
FIG. 2A is a perspective view of a connector main body that constitutes the connector according to Embodiment 1 of the present invention, the connector main body being seen from the front upper side.
Figure 2B:
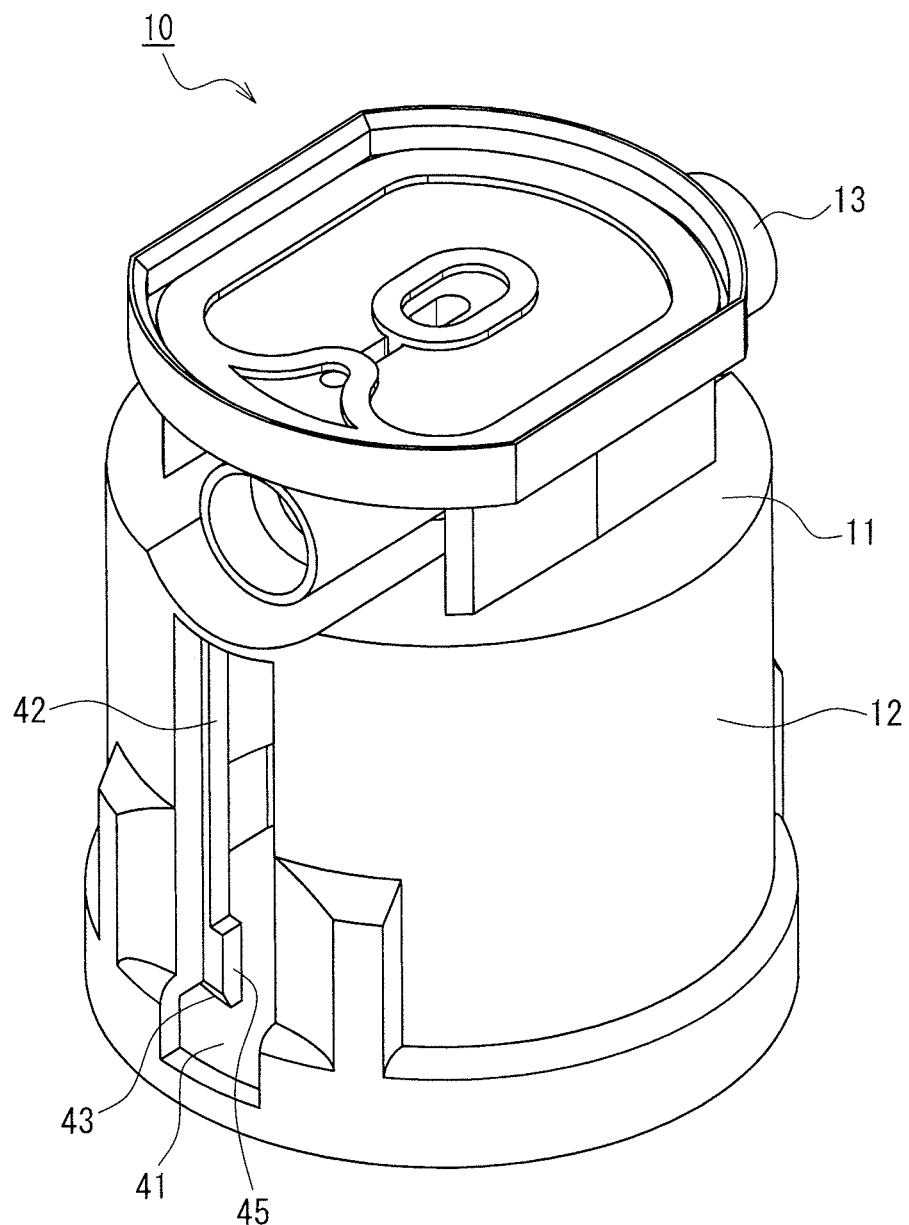
FIG. 2B is a perspective view of the connector main body that constitutes the connector according to Embodiment 1 of the present invention, the connector main body being seen from the rear upper side.
Figure 3A:
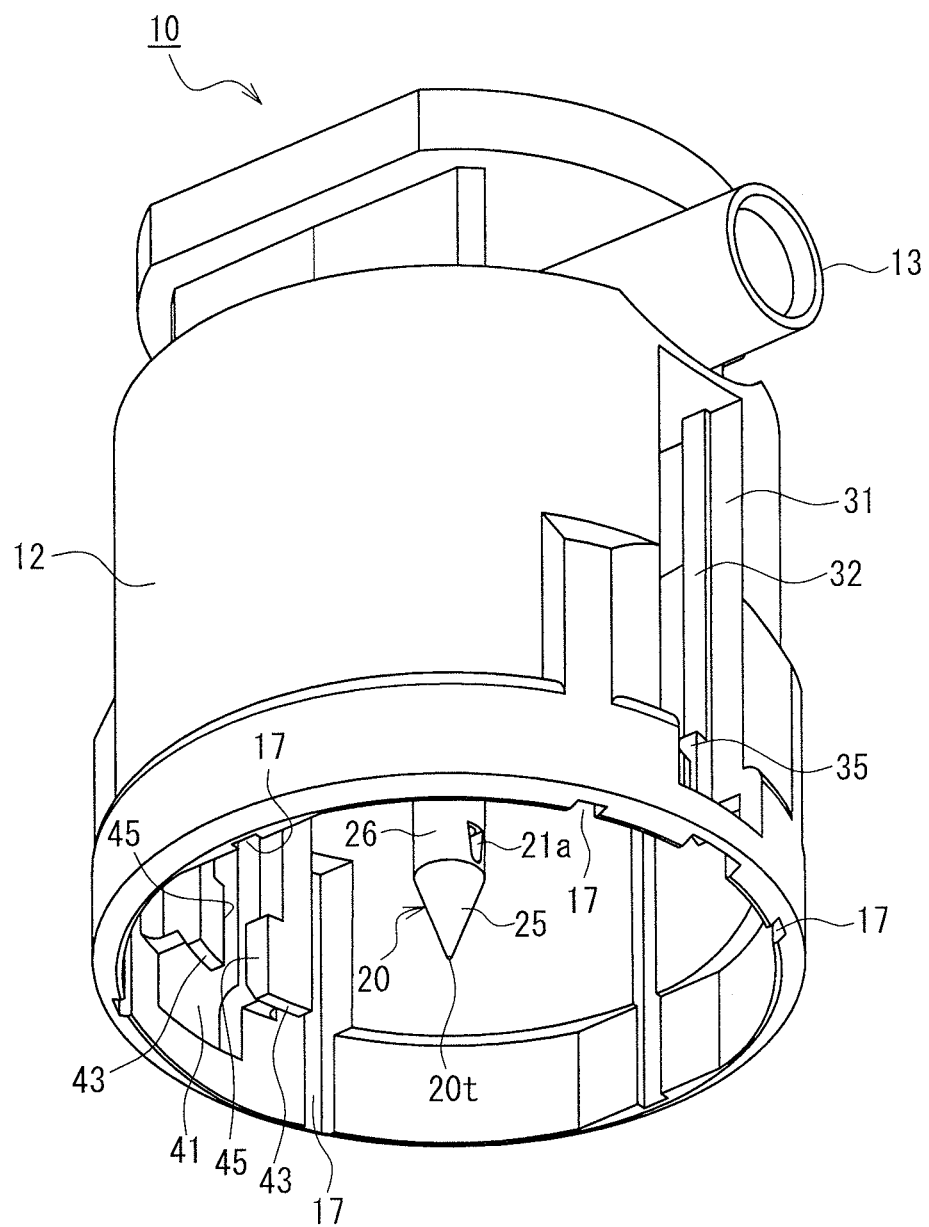
FIG. 3A is a perspective view of the connector main body that constitutes the connector according to Embodiment 1 of the present invention, the connector main body being seen from the front lower side.
Figure 3B:
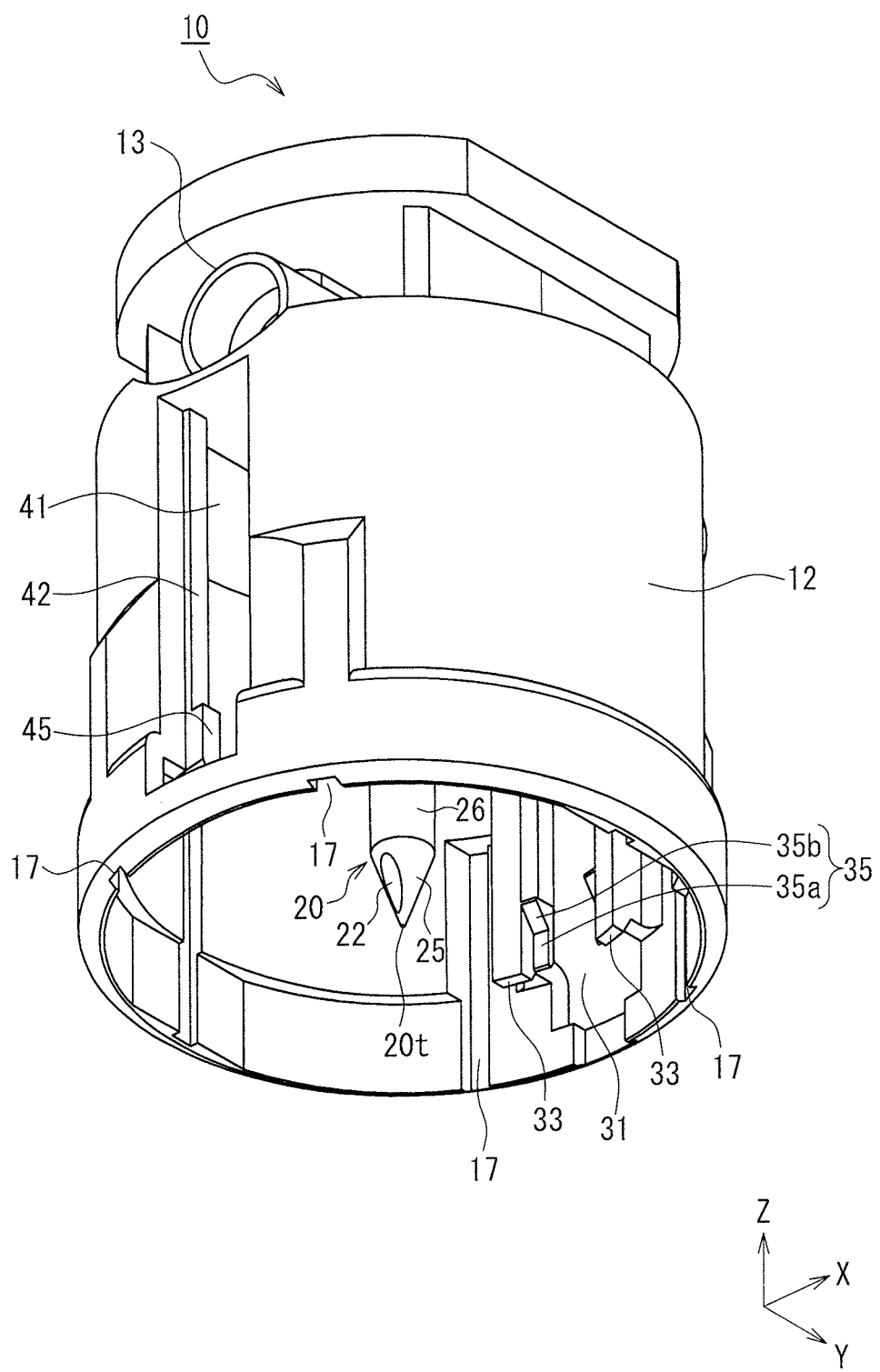
FIG. 3B is a perspective view of the connector main body that constitutes the connector according to Embodiment 1 of the present invention, the connector main body being seen from the on the rear lower side.
Figure 4A:
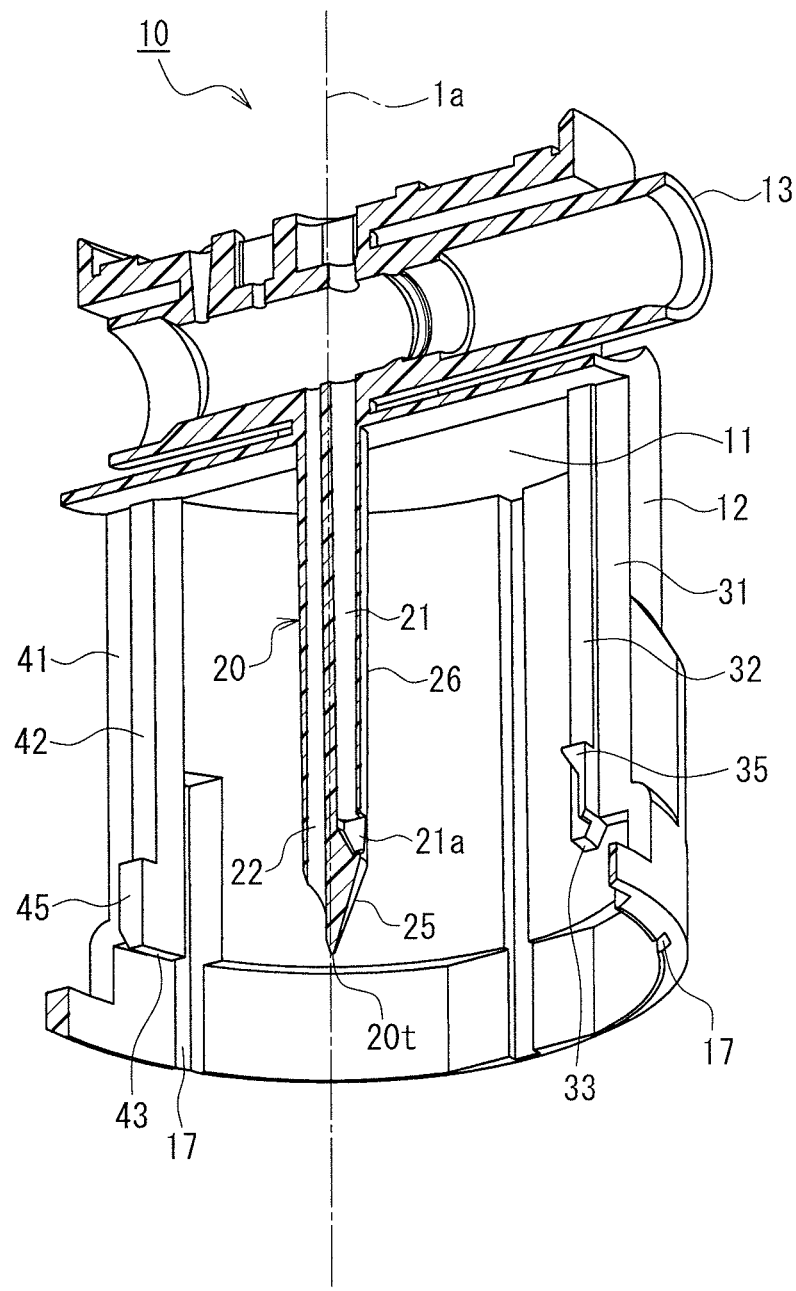
FIG. 4A is a cross-sectional perspective view of the connector main body that constitutes the connector according to Embodiment 1 of the present invention, the connector main body being seen from the front lower side.
Figure 4B:
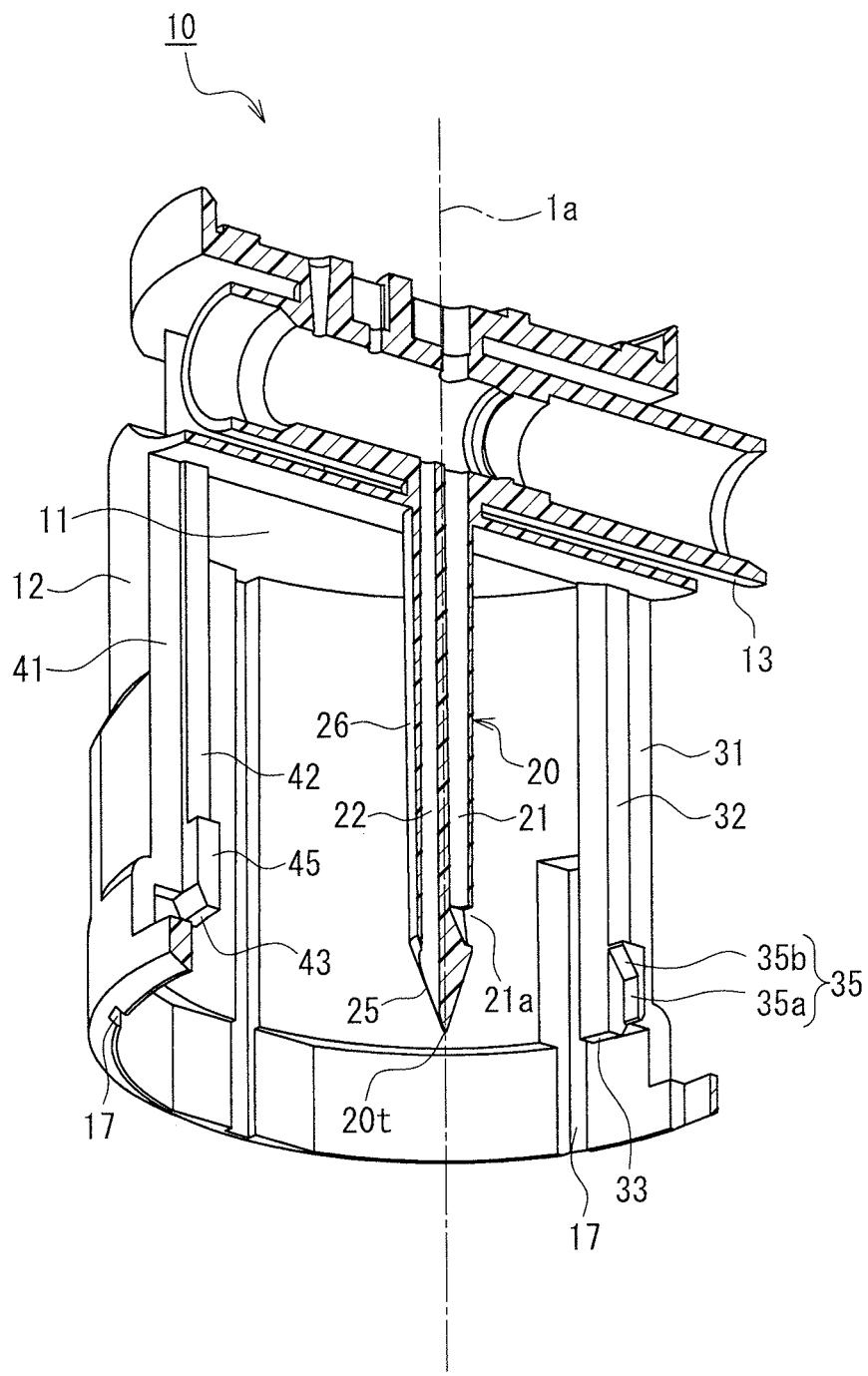
FIG. 4B is a cross-sectional perspective view of the connector main body that constitutes the connector according to Embodiment 1 of the present invention, the connector main body being seen from the rear lower side.
Figure 4B:
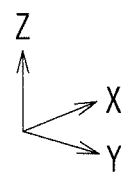
Figure 5:
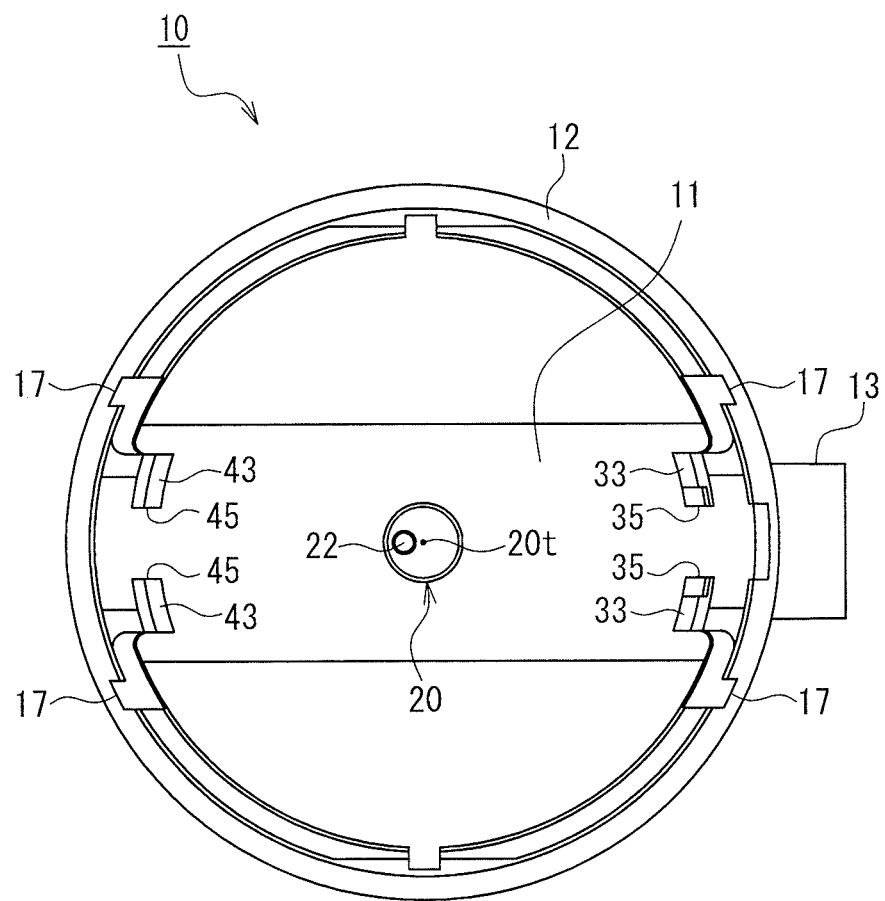
FIG. 5 is a bottom view of the connector main body that constitutes the connector according to Embodiment 1 of the present invention.

FIG. 2A is a perspective view of the connector main body 10 that is seen from the front upper side, and FIG. 2B is a perspective view thereof that is seen from the rear upper side. FIG. 3A is a perspective view of the connector main body 10 that is seen from the front lower side, and FIG. 3B is a perspective view thereof that is seen from the rear lower side. FIG. 4A is a cross-sectional perspective view of the connector main body 10 that is seen from the front lower side, and FIG. 4B is a cross-sectional perspective view thereof that is seen from the rear lower side. FIG. 5 is a bottom view of the connector main body 10. The cross sections of FIGS. 4A and 4B include the central axis 1a and the Y axis.

As shown in FIGS. 3A, 3B, 4A, and 4B, the connector main body 10 is provided with a puncture needle (sometimes referred to also as "bottle needle") 20 that is to puncture a plug 186 (see FIGS. 17 and 18, which will be described later) of a vial bottle (container) 180. The puncture needle 20 extends downward from the center of a top board 11 that has a substantially circular shape when seen in a plan view. The puncture needle 20 is arranged coaxially with the central axis 1a.

The puncture needle 20 is a rod-shaped member, and is provided with a conical portion 25 that has a substantially conical outer surface (tapered surface) in order to form a sharp tip 20t, and a columnar portion 26 that links the conical portion 25 to the top board 11. In Embodiment 1, the outer circumferential surface of the columnar portion 26 is a cylindrical surface whose outer diameter is constant in the vertical direction. However, the outer shape of the puncture needle 20 is not limited to this. For example, the columnar portion 26 may have a tapered surface whose outer diameter is slightly smaller toward the conical portion 25. Alternatively, the conical portion 25 and the columnar portion 26 do not need to be distinguished clearly, and the outer circumferential surface of the puncture needle 20 may be configured by a curved surface whose outer diameter smoothly changes from the tip 20t toward the top board 11, for example.

As shown in FIGS. 4A and 4B, the puncture needle 20 has, inside thereof, two flow channels 21 and 22 that are substantially parallel to the longitudinal direction (vertical direction) of the puncture needle 20, and are formed independently from each other. The flow channel 21 is a liquid flow channel through which liquid flows, and the flow channel 22 is a gas flow channel through which gas flows. On the tip 20t side, the liquid flow channel 21 is in communication with a lateral hole 21a. The lateral hole 21a extends to the front side along the radial direction, and opens in the outer circumferential surface of the columnar portion 26. The opening of the lateral hole 21a in the columnar portion 26 constitutes an opening, on the tip 20t side, of the liquid flow channel 21. The gas flow channel 22 opens, on the tip 20t side, in the outer circumferential surface of the conical portion 25. The liquid flow channel 21 and the gas flow channel 22 extend upward beyond the top board 11, and reach a tubular portion 13 that is provided above the top board 11 and has an inner circumferential surface that has a cylindrical surface shape.

An outer tube 12 extends downward from the top board 11 so as to surround the puncture needle 20. The outer tube 12 has a hollow and substantially cylindrical shape, and is coaxial with the puncture needle 20. The outer tube 12 has a pair of openings 31 and 41 that extend in the vertical direction. The opening 31 and the opening 41 are arranged at positions that are symmetrical with respect to the puncture needle 20.

As shown in FIGS. 2A, 4A, and 4B, a pair of guide protrusions 32 protrude, toward the inside of the front-side opening 31, from two side edges in the vertical direction of the opening 31. The guide protrusions 32 extend in the vertical direction, and the lower ends thereof end with stop ends 33. The guide protrusions 32 are located at positions that are slightly closer to the puncture needle 20 than the outer circumferential surface of the outer tube 12.

At positions slightly above the stop ends 33, a pair of stop protrusions 35 protrude from the pair of guide protrusions 32 toward the inside of the opening 31. The thickness (size), in the radial direction, of each stop protrusion 35 is relatively smaller in a lower portion 35a of the stop protrusion 35. The stop protrusion 35 has, on the inner surface (surface opposite to the puncture needle 20), an inclined surface 35b that is formed on the upper side of the thin-walled lower portion 35a, and is inclined so as to be closer to the puncture needle 20 toward the upper side as the thickness of this stop protrusion 35 changes.

As shown in FIGS. 2B, 4A, and 4B, a pair of guide protrusions 42 also protrude, to the inside of the rear-side opening 41, from two side edges in the vertical direction of the opening 41. The guide protrusions 42 extend in the vertical direction. The guide protrusions 42 are located at positions that are slightly closer to the puncture needle 20 than the outer circumferential surface of the outer tube 12.

A pair of stop protrusions 45 protrude from the pair of guide protrusions 42 toward the inside of the opening 41. The positions of the lower end of the guide protrusion 42 and the lower end of the stop protrusion 45 match in the vertical direction, and together form a stop end 43. Different from the stop protrusions 35, the thickness (size), in the radial direction, of the stop protrusions 45 is constant in the vertical direction. The stop protrusions 45 do not have, on the inner surface (surface opposite to the puncture needle 20) thereof, an inclined surface that is similar to the inclined surface 35b of the stop protrusion 35.

The inner circumferential surface of the outer tube 12 has four grooves 17 that extend upward from the lower end of the outer tube 12. Two grooves 17 are arranged so as to sandwich the opening 31 in the circumferential direction, and the remaining two grooves 17 are arranged so as to sandwich the opening 41 in the circumferential direction.

The connector main body 10 is preferably made of a hard material. Specifically, it is possible to use a resin material such as polyacetal, polycarbonate, polystyrene, polyamide, polypropylene, or rigid polyvinyl chloride. The connector main body 10 may be integrally molded, using such a resin material, as a single piece by injection molding, for example.

1.2. Slider

Figure 6A:
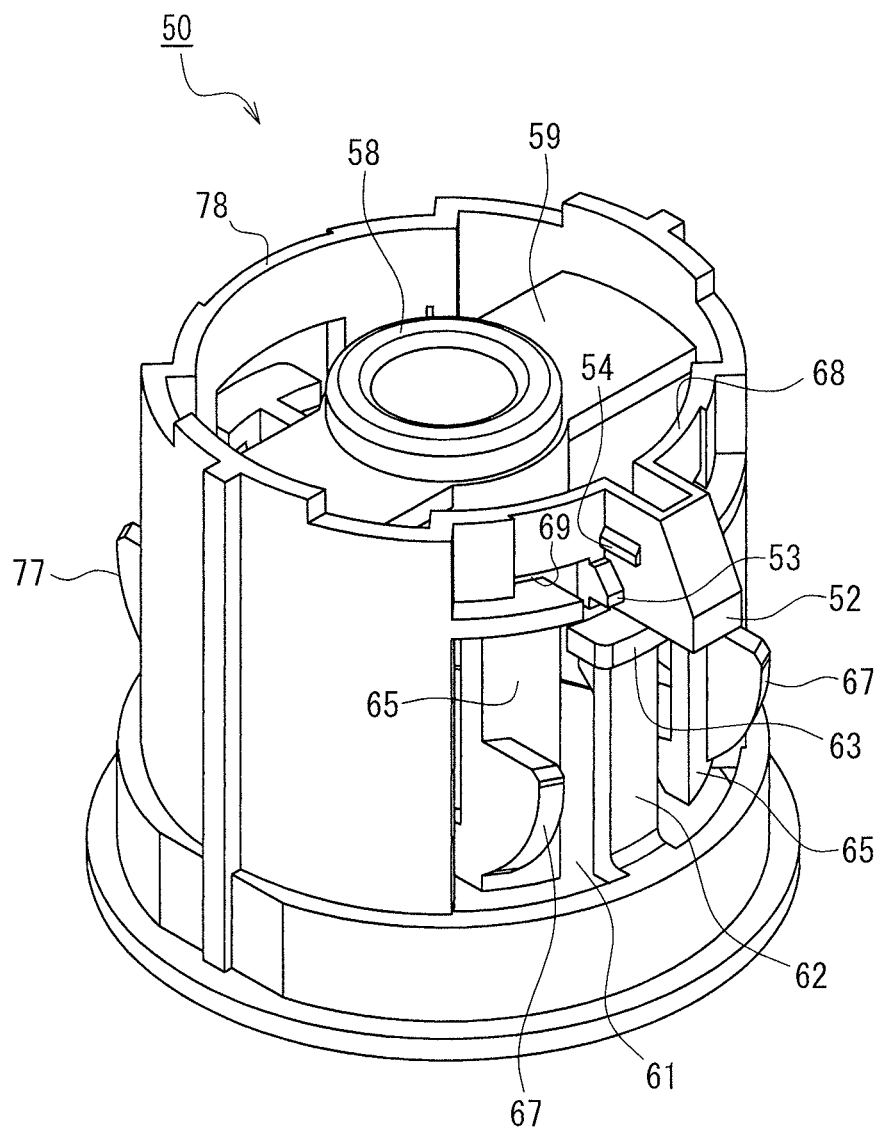
FIG. 6A is a perspective view of a slider that constitutes the connector according to Embodiment 1 of the present invention, the slider being seen from the front upper side.
Figure 6B:
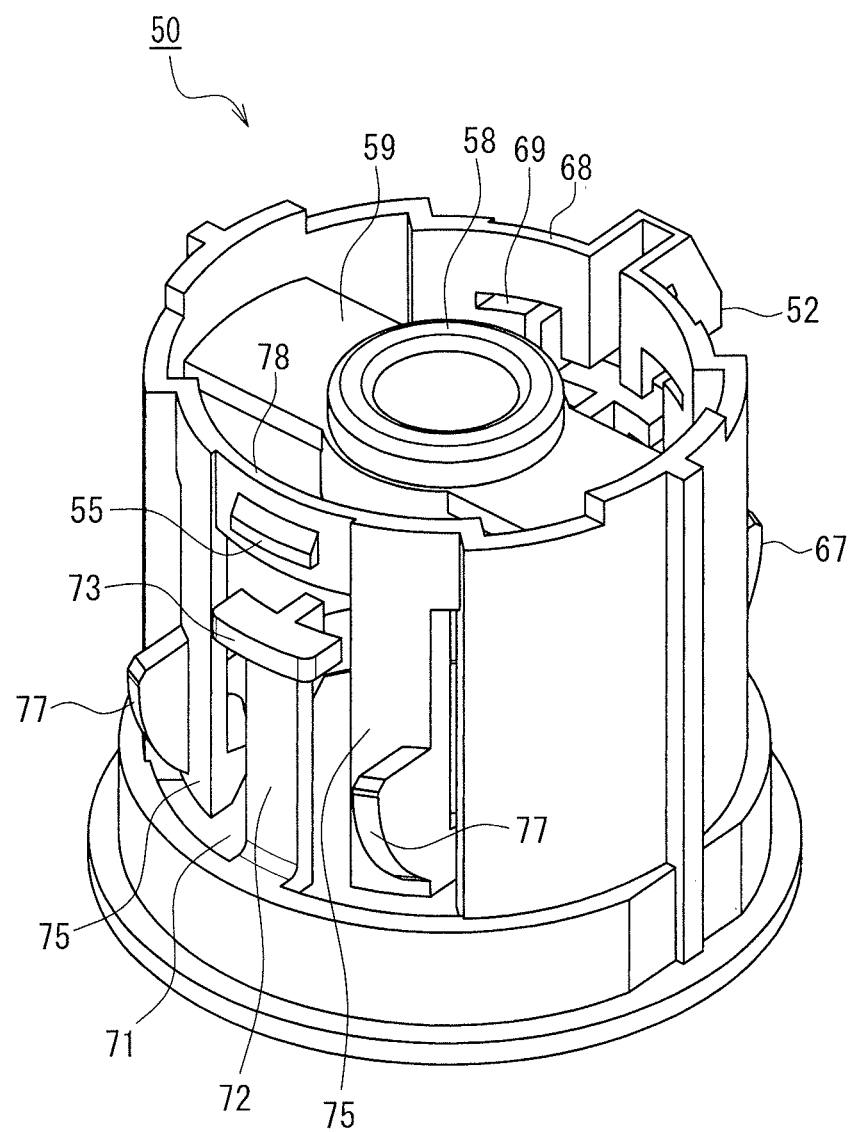
FIG. 6B is a perspective view of the slider that constitutes the connector according to Embodiment 1 of the present invention, the slider being seen from the rear upper side.
Figure 7A:
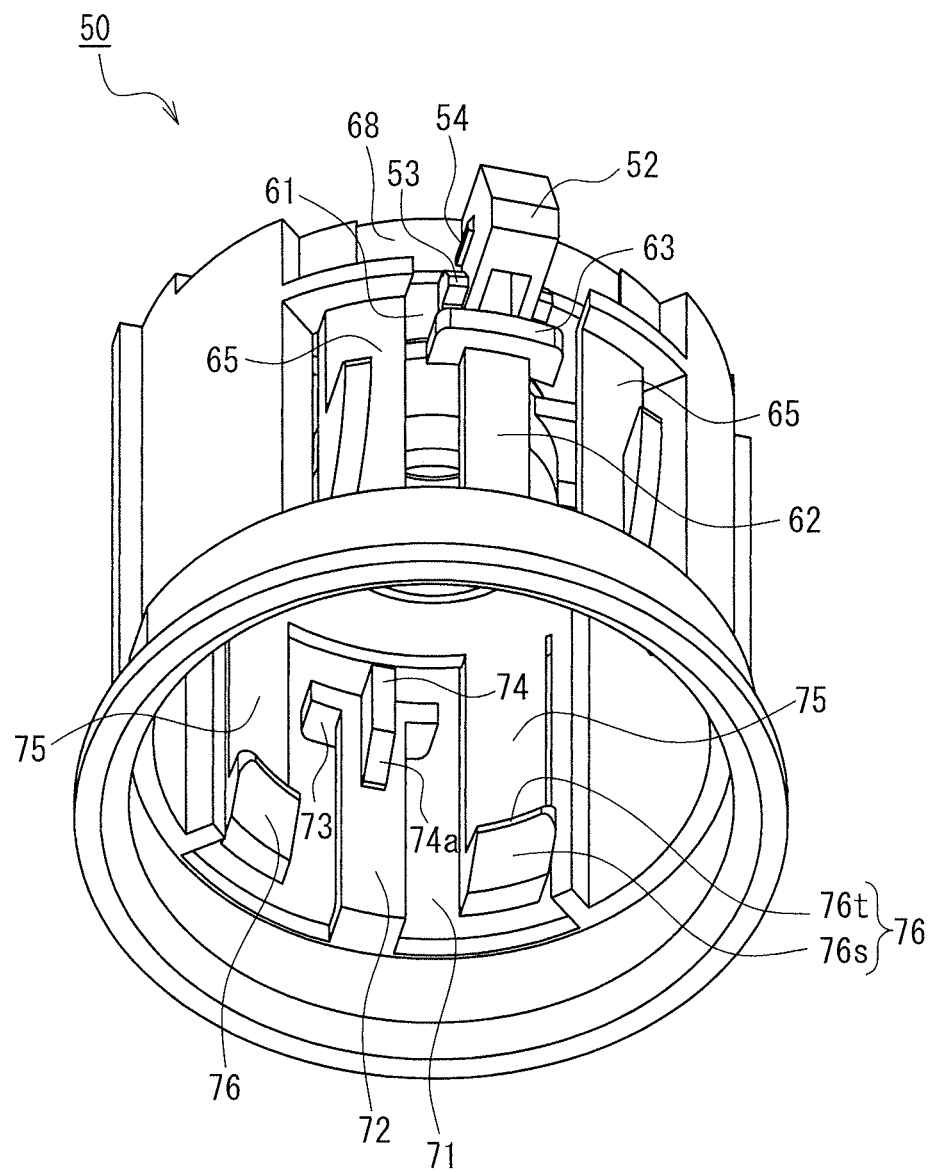
FIG. 7A is a perspective view of the slider that constitutes the connector according to Embodiment 1 of the present invention, the slider being seen from the front lower side.
Figure 7B:
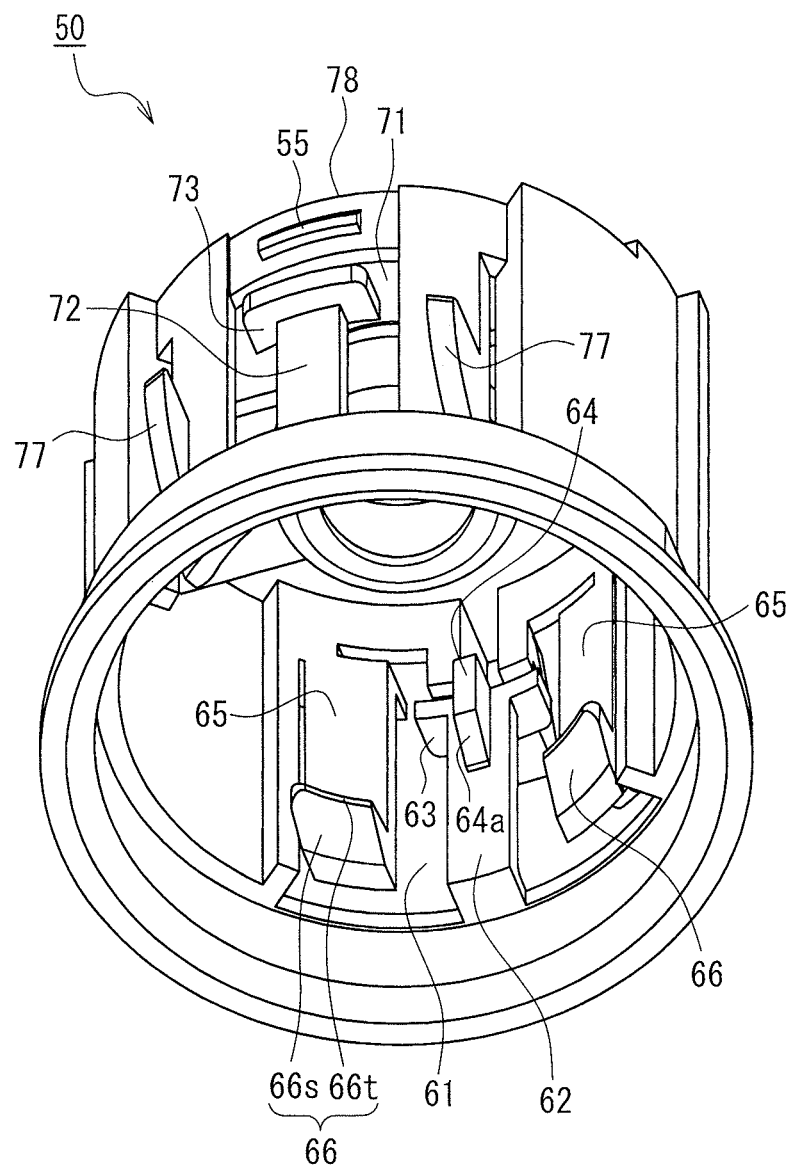
FIG. 7B is a perspective view of the slider that constitutes the connector according to Embodiment 1 of the present invention, the slider being seen from the rear lower side.
Figure 8A:
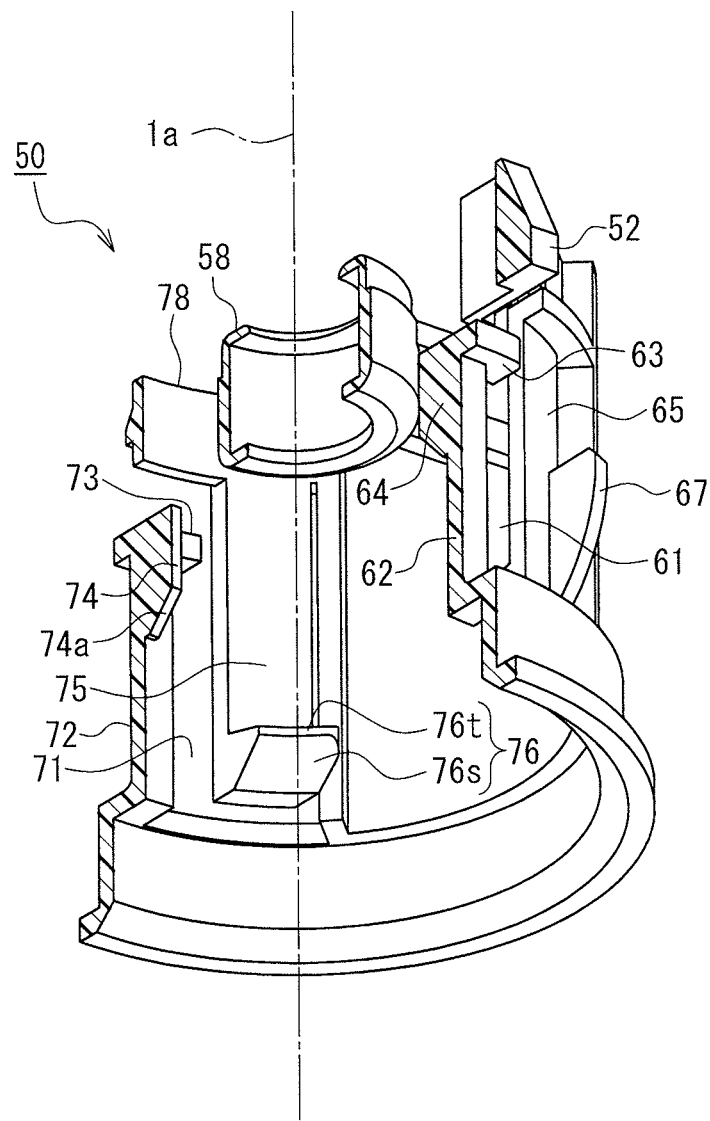
FIG. 8A is a cross-sectional perspective view of the slider that constitutes the connector according to Embodiment 1 of the present invention, the slider being seen from the front lower side.
Figure 8B:
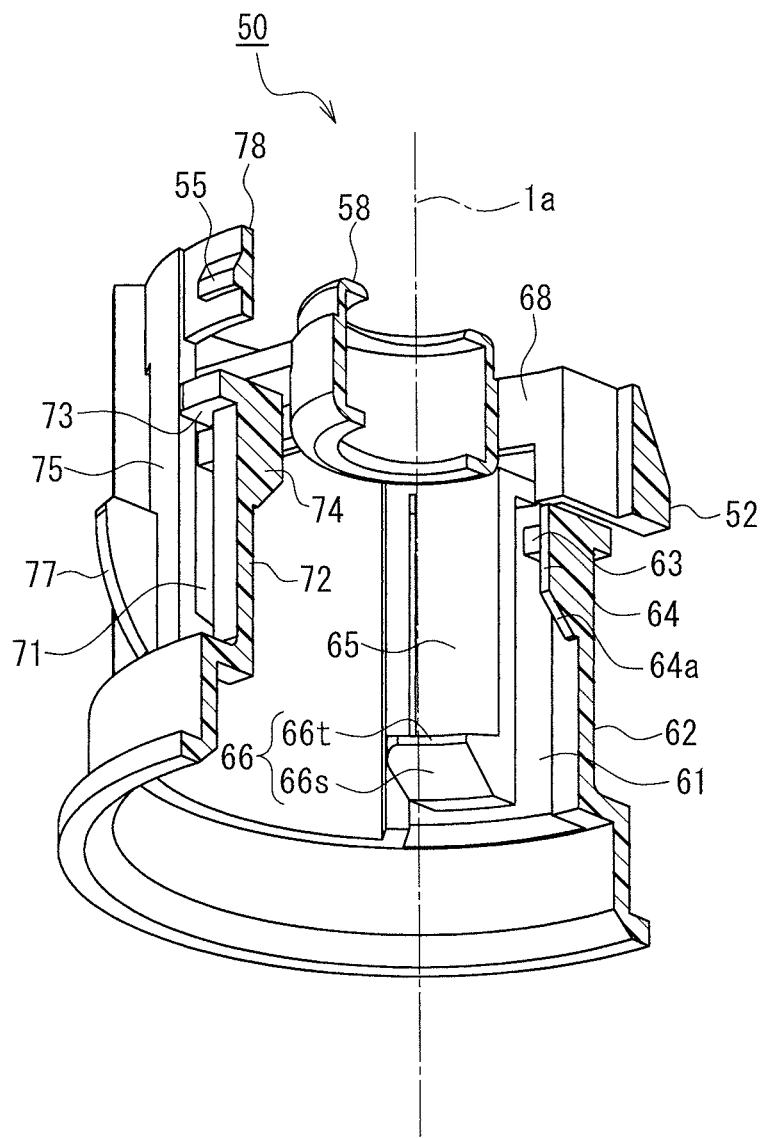
FIG. 8B is a cross-sectional perspective view of the slider that constitutes the connector according to Embodiment 1 of the present invention, the slider being seen from the rear lower side.
Figure 9:
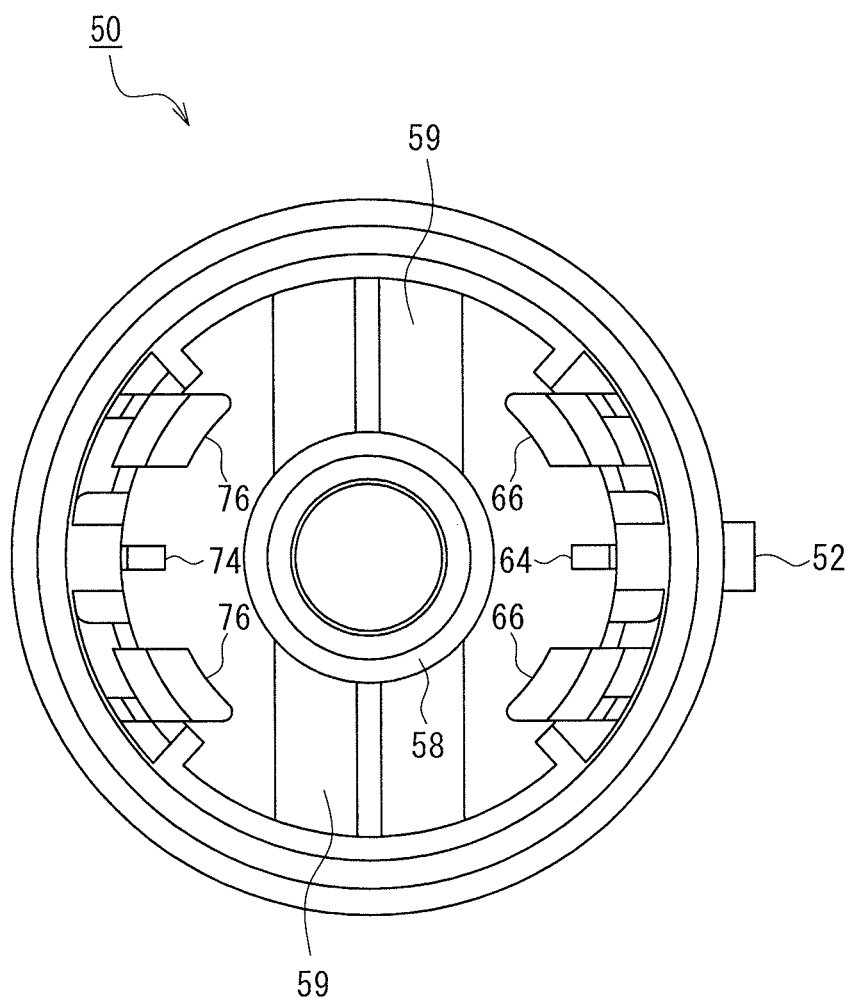
FIG. 9 is a bottom view of the slider that constitutes the connector according to Embodiment 1 of the present invention.
Figure 9:
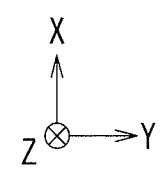

FIG. 6A is a perspective view of the slider 50 that is seen from the front upper side, and FIG. 6B is a cross-sectional perspective view thereof that is seen from the rear upper side. FIG. 7A is a perspective view of the slider 50 that is seen from the front lower side, and FIG. 7B is a perspective view thereof that is seen from the rear lower side. FIG. 8A is a cross-sectional perspective view of the slider 50 that is seen from the front lower side, and FIG. 8B is a cross-sectional perspective view thereof that is seen from the rear lower side. FIG. 9 is a bottom view of the slider 50. The cross sections of FIGS. 8A and 8B include the central axis 1a and the Y axis.

As shown in FIGS. 6A, 6B, 7A, 7B, 8A, and 8B, the slider 50 has, as a whole, a hollow and substantially cylindrical shape that is coaxial with the central axis 1a and opens in the vertical direction. The slider 50 has, in the inside thereof, a holder 58 that has a substantially cylindrical shape and opens in the vertical direction, the holder 58 being coaxial with the central axis 1a. The holder 58 is fixed, at positions in the vicinity of the upper end of the slider 50, to the inner circumferential surface of the slider 50 via a holding bar 59 that extends parallel to the X axis direction.

The slider 50 has, on its side surface that has a substantially cylindrical surface shape, a pair of openings 61 and 71. The opening 61 and the opening 71 are arranged at positions that are symmetrical with respect to the central axis 1a. The opening 61 is arranged on the front side, and the opening 71 is arranged on the rear side.

In the openings 61 and 71, slide restricting arms (hereinafter, referred to simply as "restricting arms") 62 and 72 respectively extend upward from the lower edges of the openings 61 and 71. The restricting arms 62 and 72 have a cantilever support structure in which head portions 63 and 73 on the upper ends thereof are free ends. The restricting arms 62 and 72 are elastically bendable and deformable so that the head portions 63 and 73 are displaced outwardly in the radial direction. The restricting arms 62 and 72 have a substantially "T" shape such that the head portions 63 and 73 thereof protrude to both sides in the circumferential direction. As shown in FIGS. 7A, 7B, 8A, and 8B, abutting protrusions 64 and 74 protrude toward the central axis 1a from respective positions in the vicinity of the upper ends on the inner surfaces (opposite to the central axis 1a) of the restricting arms 62 and 72. The abutting protrusions 64 and 74 are respectively provided with edges 64a and 74a that are inclined with respect to the central axis 1a so as to be further distanced away from the central axis 1a toward the lower side.

A pair of grip arms 65 extend downward from the vicinity of the upper edge of the opening 61 so as to sandwich the restricting arm 62 in the circumferential direction. Similarly, a pair of grip arms 75 extend downward from the upper edge of the opening 71 so as to sandwich the restricting arm 72 in the circumferential direction. The grip arms 65 and 75 have a cantilever support structure in which the lower ends thereof are free ends. The grip arms 65 and 75 are elastically bendable and deformable so that the lower ends (free ends) thereof are displaced outwardly in the radial direction. Lock protrusions 67 and 77 protrude outwardly, substantially in the radial direction, from positions in the vicinity of the lower ends on the outer surfaces (surfaces that face away from the central axis 1a) of the grip arms 65 and 75. As shown in FIGS. 7A, 7B, 8A, and 8B, claws 66 and 76 protrude toward the central axis 1a from positions in the vicinity of the lower ends on the inner surfaces (surfaces opposite to the central axis 1a) of the grip arms 65 and 75. The claws 66 and 76 respectively have, on the lower sides of their tips 66t and 76t (that are formed at positions closest to the central axis 1a), inclined surfaces 66s and 76s that are inclined so as to be further distanced away from the central axis 1a moving downward from the tips 66t and 76t toward the lower side.

As shown in FIG. 6A, a release button 52 protrudes outwardly in the radial direction from a substantially central position, in the circumferential direction, of a front upper frame 68 that constitutes the upper edge of the front-side opening 61. The release button 52 has, on each of the side surfaces (surfaces substantially parallel to the radial direction) thereof, an intermediate stopper 53 and a retaining protrusion 54. The retaining protrusion 54 extends in horizontal direction and substantially in the radial direction. The intermediate stopper 53 is located below the retaining protrusion 54. The size (thickness), in the radial direction, of the front upper frame 68 is relatively small. Accordingly, the front upper frame 68 can elastically deform so that the release button 52 becomes closer to the central axis 1a by being pressed inwardly in the radial direction (toward the central axis 1a). The front upper frame 68 and the upper ends (fixed ends) of the grip arms 65 are distanced via a slit 69 so that deformation of one of the front upper frame 68 and the grip arms 65 does not move the other one (see FIGS. 6A and 6B).

As shown in FIG. 6B, a retaining protrusion 55 protrudes outwardly from a substantially central position, in the circumferential direction, of a rear upper frame 78 that constitutes the upper edge of the rear-side opening 71. The retaining 55 extends in the circumferential direction.

The slider 50 is preferably made of a hard material. Specifically, it is possible to use a resin material such as polyacetal, polycarbonate, polystyrene, polyamide, polypropylene, or rigid polyvinyl chloride. The slider 50 may be integrally molded, using such a resin material, as a single piece by injection molding, for example.

1.3. Cover

Figure 10A:
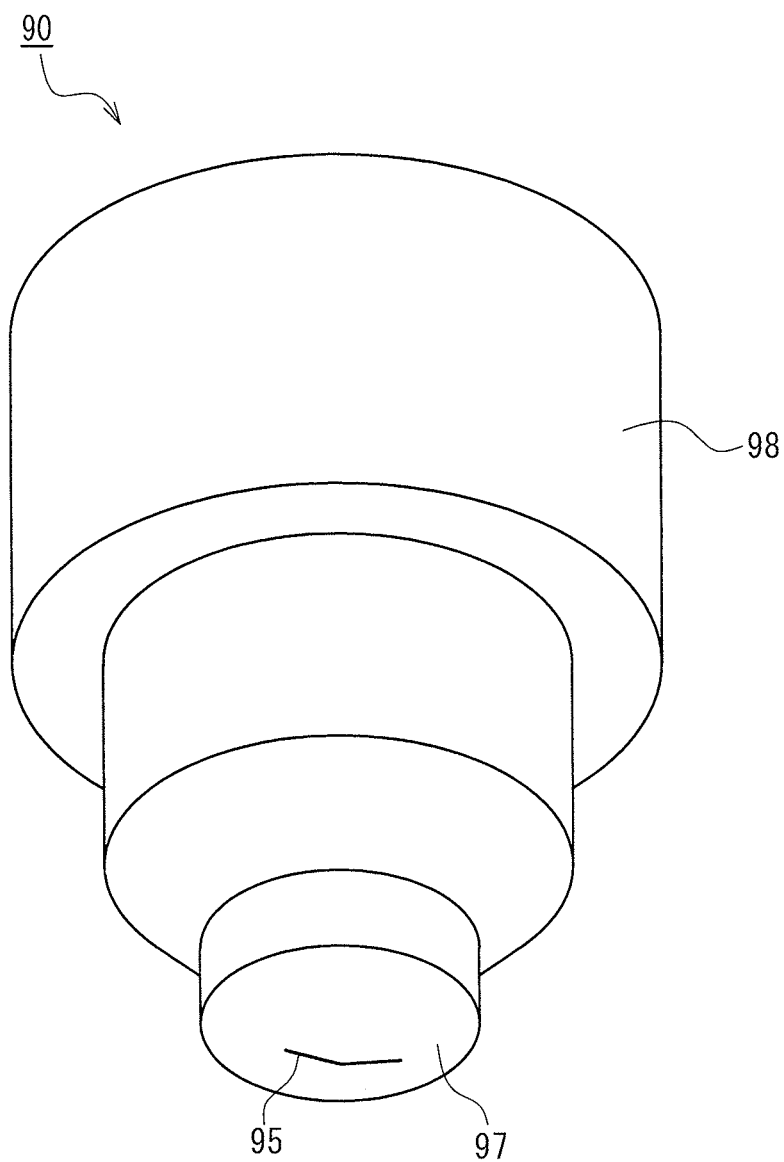
FIG. 10A is a perspective view of a cover that constitutes the connector according to Embodiment 1 of the present invention, the cover being seen from the bottom thereof.
Figure 10B:
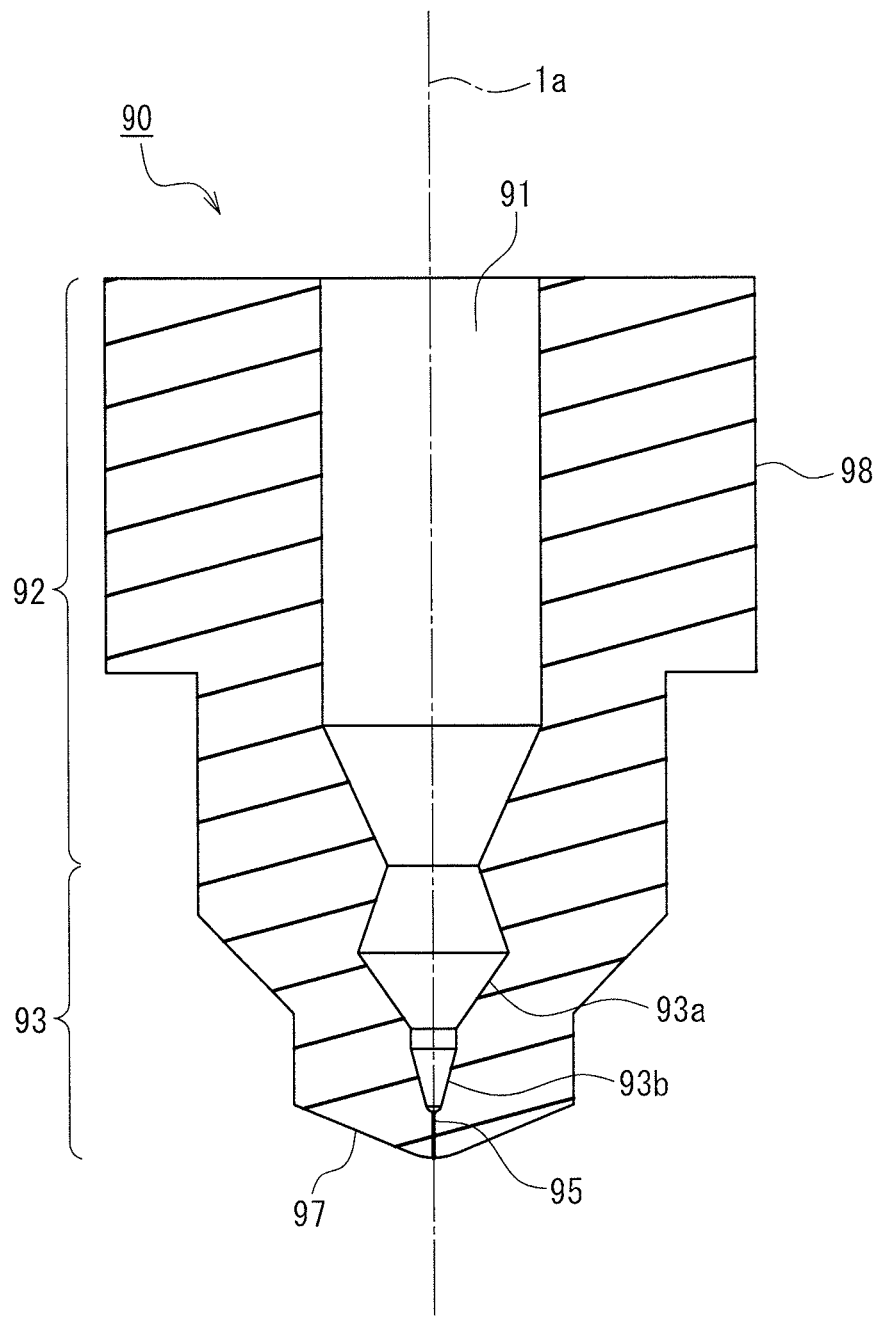
FIG. 10B is a cross-sectional view of the cover that constitutes the connector according to Embodiment 1 of the present invention.

FIG. 10A is a perspective view of the cover 90 that is seen from below, and FIG. 10B is a cross-sectional view of the cover 90. The cover 90 is symmetrical with respect to the central axis 1a at an arbitrary rotational angle (so-called rotational isotropy) (however, a slit 95 is excluded).

The cover 90 is flexible (pliable), and is made of a rubber-like elastic material (so-called elastomer) configured to deform upon the application of an external force and immediately revert to the initial shape upon the removal of the external force. Specifically, it is possible to use a rubber such as natural rubber, isoprene rubber, or silicone rubber; or a thermoplastic elastomer such as styrene elastomer, olefin elastomer, or polyurethane elastomer. The cover 90 is integrally molded, using such a material, as a single piece.

As shown in FIG. 10B, the cover 90 has an inner cavity 91 that is formed along the central axis 1a. The inner cavity 91 opens in the upper end surface of the cover 90. The cover 90 is provided with a seal region 92 on the upper side (base end side), and a deformable region 93 on the lower side (tip side), the seal region 92 and the deformable region 93 being adjacent to each other.

In an initial state (see FIGS. 13 and 14, which will be described later), the puncture needle 20 is inserted into the seal region 92. The inner circumferential surface of the inner cavity 91 in the seal region 92 is formed conforming to the shape of the outer circumferential surface of the puncture needle 20. The inner diameter of the seal region 92 is preferably set to be slightly smaller than the outer diameter of the puncture needle 20 so that the inner circumferential surface of the inner cavity 91 in the seal region 92 is liquid-tightly and air-tightly in intimate contact with the outer circumferential surface (particularly, a region in the vicinity of the lateral hole 21*a*) of the puncture needle 20.

The deformable region 93 may include a movable portion 93*a* whose inner circumferential surface has a substantially rhomboidal cross-sectional shape such that the inner diameter increases and then decreases along the central axis 1*a*. In Embodiment 1, only one movable portion 93*a* is provided, but a plurality of movable portions 93*a* that have the same substantially rhomboidal cross section may be arranged along the central axis 1*a*. The deformable region 93 includes, adjacently to the movable portion 93*a* and on the lower side thereof, a guide portion 93*b* that has a substantially conical surface shape such that the inner diameter is smaller on the lower side. Note that the guide portion 93*b* may be omitted.

The outer circumferential surface of the cover 90 has, as a whole, a shape such that the outer diameter is smaller toward the lower side. The outer diameter is approximately smaller in the deformable region 93 than in the seal region 92. Furthermore, the deformable region 93 is provided with the movable portion 93*a* having an inner circumferential surface shape that is substantially similar to an accordion. Due to the above, the mechanical strength of the cover 90 is approximately lower in the deformable region 93 than in the seal region 92. Accordingly, the deformable region 93 can relatively easily be subjected to compression deformation and stretching deformation in the vertical direction, as compared to the seal region 92.

A lower end surface 97 of the deformable region 93 is a projection surface that projects downward. The projection surface 97 may have any shape, and may be suitably set as a conical surface, a spherical surface, a non-spherical surface that is dome-like and smooth, or the like.

The slit 95 penetrates the tip of the cover 90 in the vertical direction. As shown in FIG. 10A, the slit 95 is a linear incision that has a shape of "–" (minus) when seen from below. In the initial state in which the puncture needle 20 does not penetrate the slit 95, it is preferable that opposing edges (lips) that form the slit 95 are in contact with each other. The slit 95 passes through the crownpiece of the projection surface 97, and the deepest portion of the inner cavity 91 (that is, the deepest portion of the guide portion 93*b*).

A hold portion 98 of the cover 90 that has the largest outer diameter is fitted to the holder 58 of the slider 50 (see FIGS. 13 and 14, which will be described later). The hold portion 98 is provided in the seal region 92.

1.4. Connector in Initial State

Figure 11A:
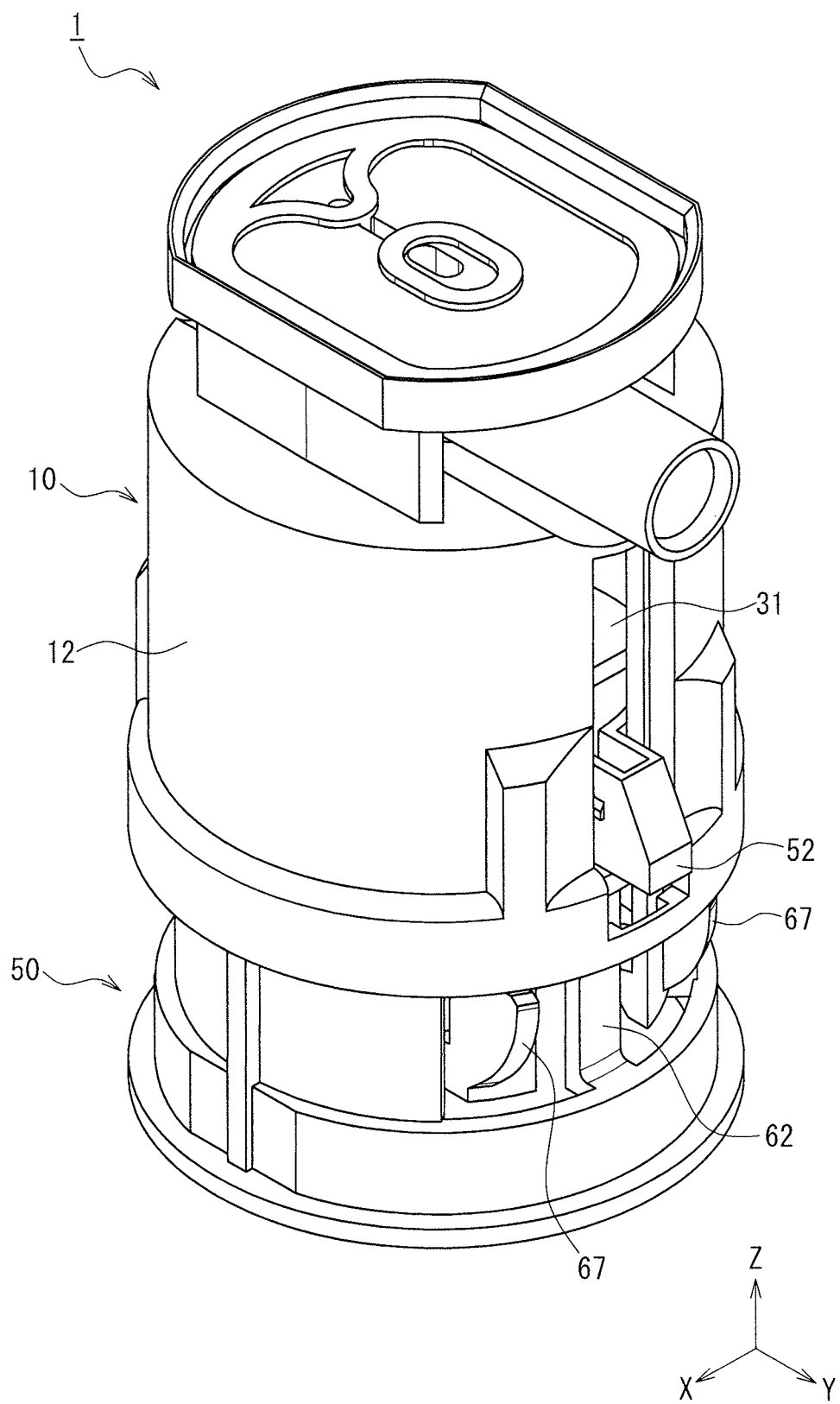
FIG. 11A is a perspective view of the connector according to Embodiment 1 of the present invention in an initial state, the connector being seen from the front upper side.
Figure 11B:
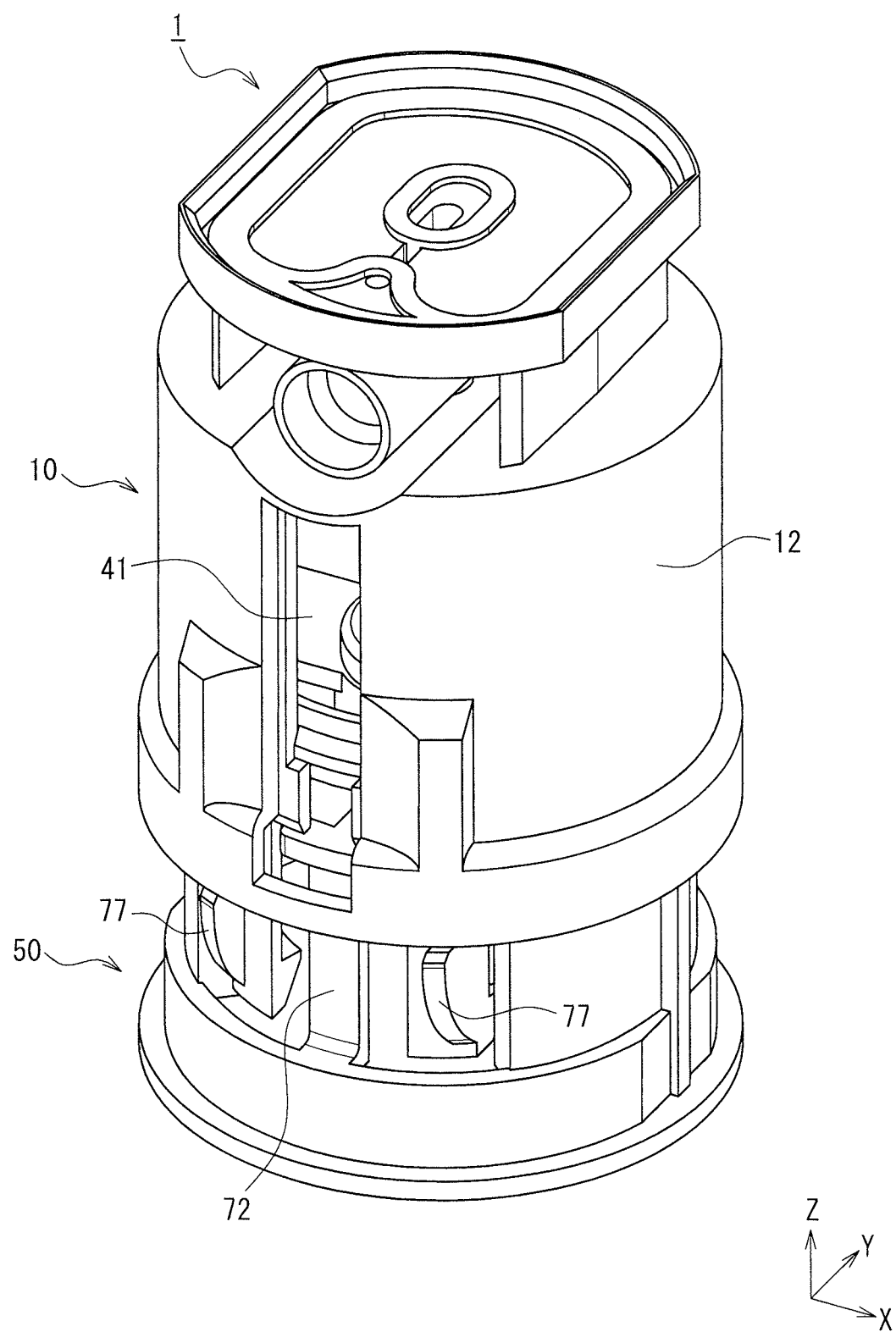
FIG. 11B is a perspective view of the connector according to Embodiment 1 of the present invention in the initial state, the connector being seen from the rear upper side.
Figure 12A:
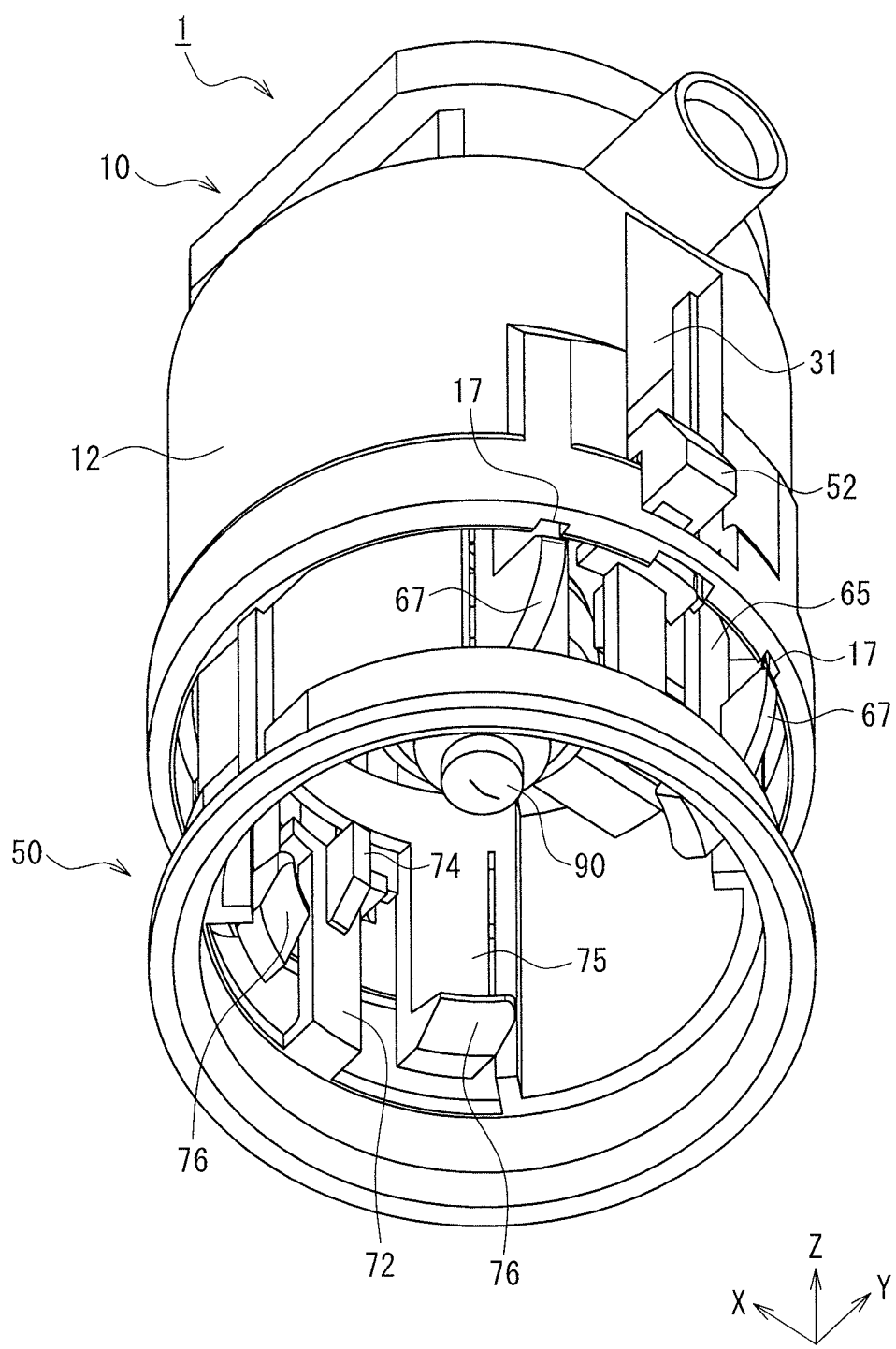
FIG. 12A is a perspective view of the connector according to Embodiment 1 of the present invention in the initial state, the connector being seen from the front lower side.
Figure 12B:
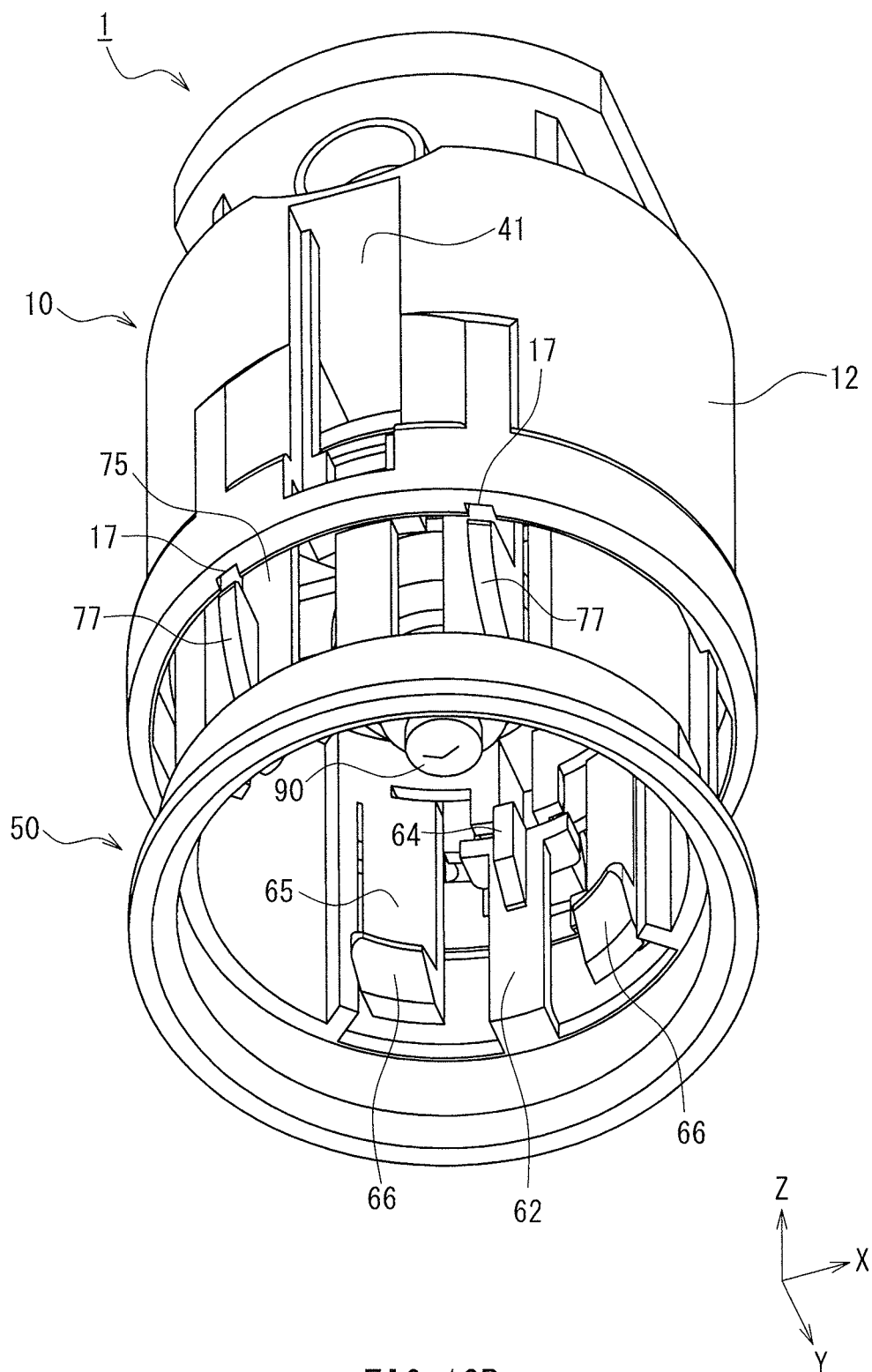
FIG. 12B is a perspective view of the connector according to Embodiment 1 of the present invention in the initial state, the connector being seen from the rear lower side.

FIG. 11A is a perspective view of the connector 1 that is seen from the front upper side, and FIG. 11B is a perspective view of the connector 1 that is seen from the rear upper side. FIG. 12A is a perspective view of the connector 1 that is seen from the front lower side, and FIG. 12B is a perspective view of the connector 1 that is seen from the rear lower side. FIG. 13 is a cross-sectional perspective view taken along the surface of the connector 1 that includes the central axis 1*a*.

Figure 13:
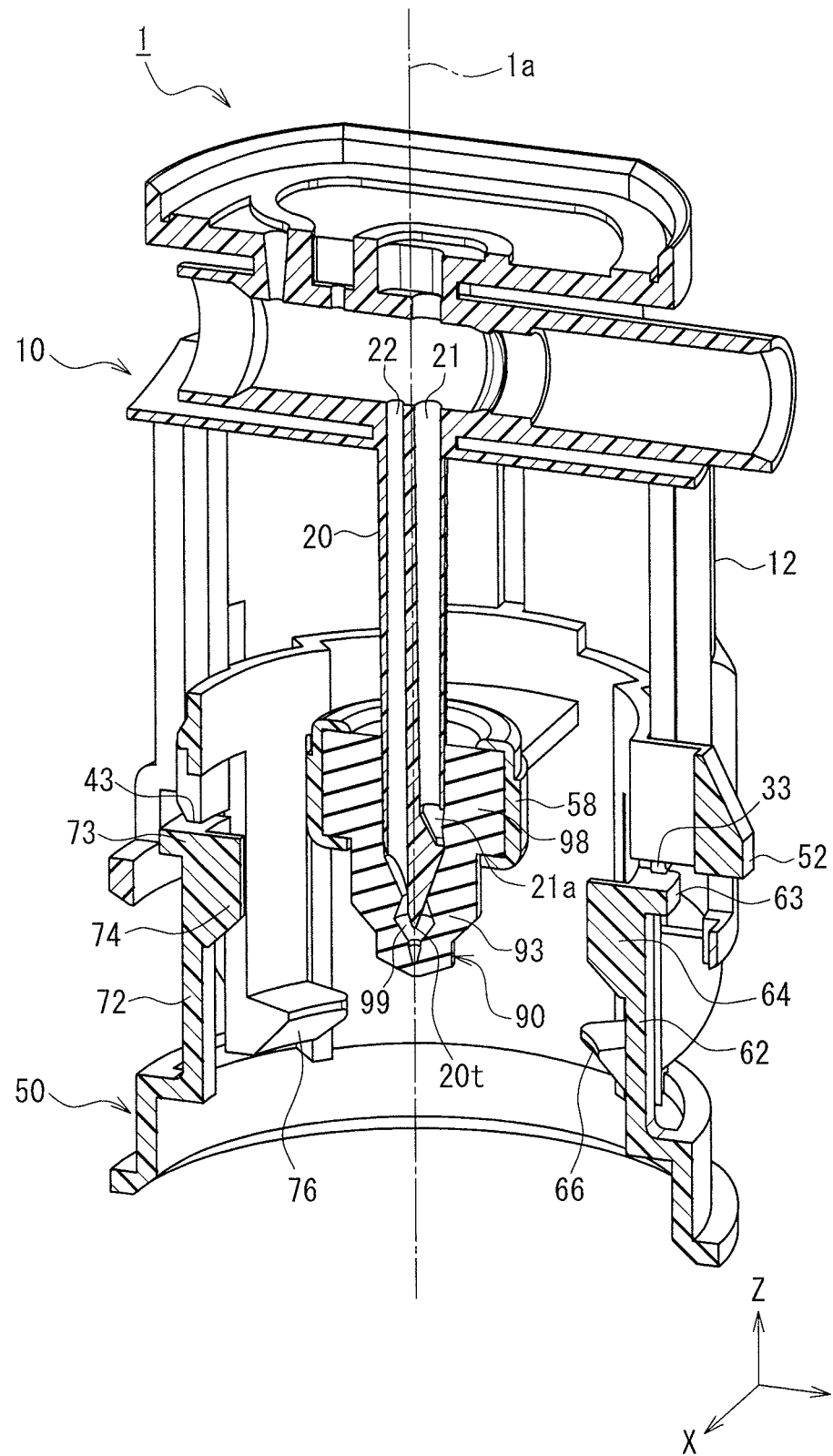
FIG. 13 is a cross-sectional perspective view of the connector according to Embodiment 1 of the present invention in the initial state.
Figure 14:
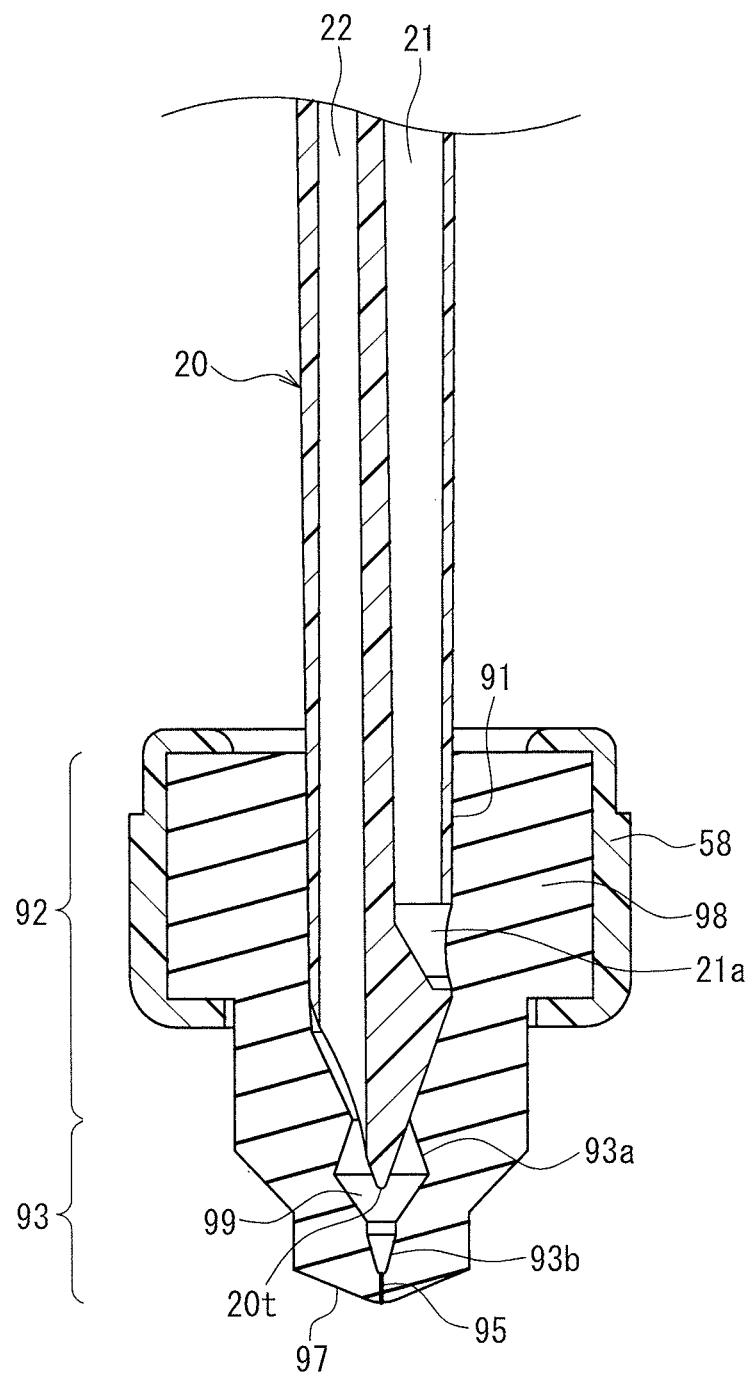
FIG. 14 is an enlarged cross-sectional view of the tip of a puncture needle of the connector according to Embodiment 1 of the present invention in the initial state, and a cover thereof that covers the puncture needle.

As shown in FIG. 13, the cover 90 is held by the slider 50 by the hold portion 98 of the cover 90 being fitted to the holder 58. The slider 50 is inserted into the outer tube 12 of the connector main body 10 from below. Thus, the connector 1 according to Embodiment 1 is assembled. The connector 1 that is shown in FIGS. 11A, 11B, 12A, 12B, and 13 is not yet mounted to a vial bottle. This state of the connector his referred to as "initial state". In the connector bin the initial state, the "initial position" refers to the position of the slider 50 with respect to the connector main body 10.

As shown in FIG. 13, the portion of the puncture needle 20 that includes the tip 20*t* is covered by the cover 90. FIG. 14 is an enlarged view of this portion. The puncture needle 20 is inserted into the inner cavity 91 in the seal region 92 of the cover 90. The inner circumferential surface of the inner cavity 91 of the cover 90 is in intimate contact with the outer circumferential surface of the puncture needle 20. Accordingly, in the seal region 92, a liquid-tight and air-tight seal is formed between the inner circumferential surface of the inner cavity 91 and the outer circumferential surface of the puncture needle 20. Furthermore, in the seal region 92, the inner circumferential surface of the inner cavity 91 is in intimate contact with the outer circumferential surface of the puncture needle 20 so as to liquid-tightly and air-tightly close the opening of the lateral hole 21*a* that is in communication with the liquid flow channel 21 (and preferably also the opening of the gas flow channel 22).

The tip 20*t* of the puncture needle 20 does not reach the deepest portion of the inner cavity 91 of the cover 90. The puncture needle 20 is not substantially inserted into the deformable region 93. Accordingly, a space 99 is formed in the inner cavity 91 in the deformable region 93. As described above, in the seal region 92, the inner circumferential surface of the inner cavity 91 is in intimate contact with the outer circumferential surface of the puncture needle 20. Furthermore, the opposing edges (lips) that form the slit 95 are in contact with each other and are closed. Accordingly, the space 99 is a closed space that is preferably liquid-tightly and air-tightly sealed. The closed space 99 can function as a space for accumulating a drug solution.

Figure 15:
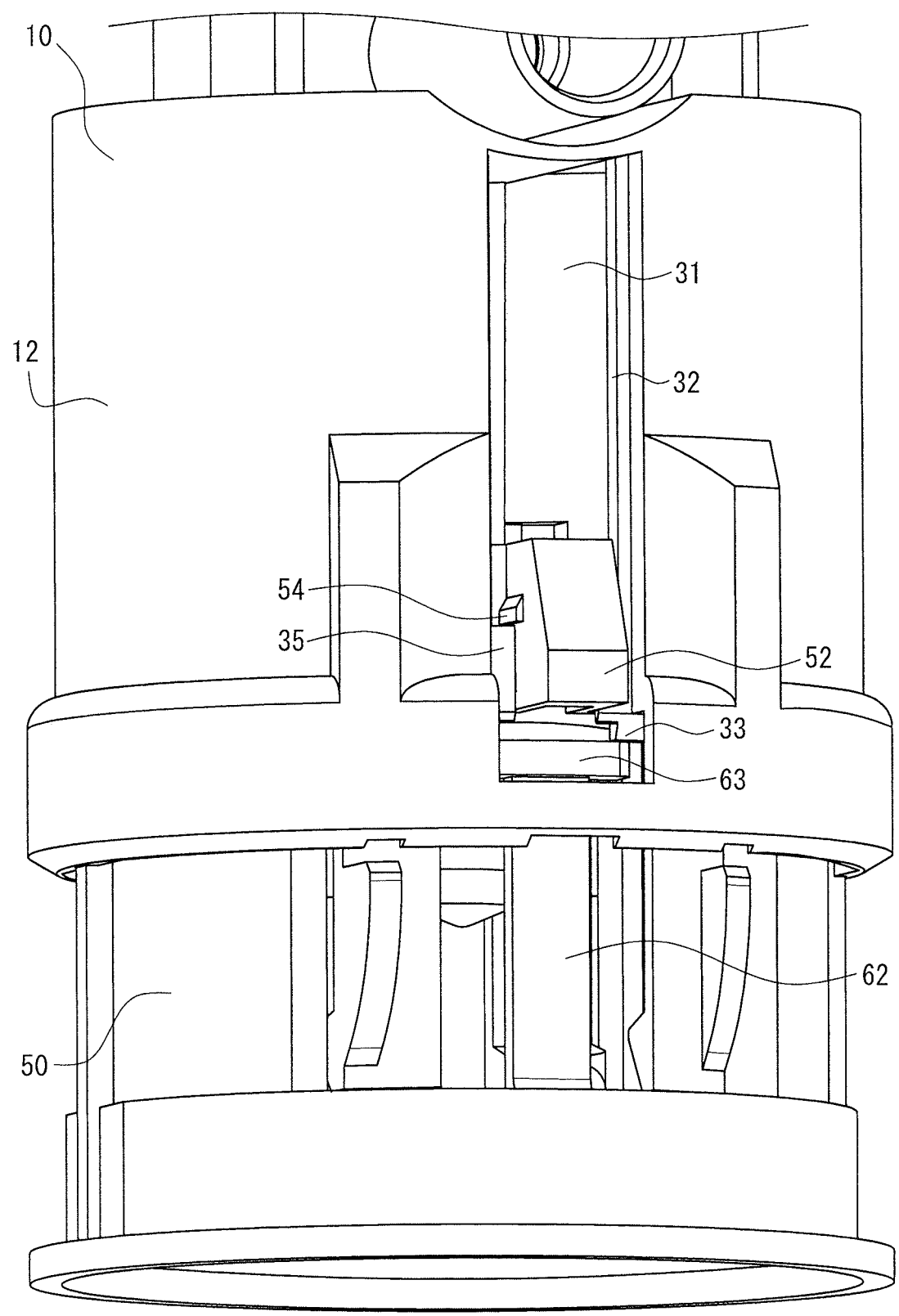
FIG. 15 is an enlarged perspective view of a front-side opening of the connector main body of the connector according to Embodiment 1 of the present invention in the initial state.

FIG. 15 is an enlarged perspective view of the front-side opening 31 of the connector main body 10. The release button 52 of the slider 50 is fitted to the opening 31, and the tip thereof protrudes slightly outward from the outer circumferential surface of the outer tube 12 of the connector main body 10.

The head portion 63, at the upper end, of the front-side restricting arm 62 of the slider 50 is seen in the opening 31. The head portion 634 abuts, in the vertical direction, against the stop ends 33, at the lower end, of the guide protrusions 32 of the connector main body 10 that protrude into the opening 31.

The retaining protrusions 54 protruding from the side surfaces of the release button 52 of the slider 50 are located above the stop protrusions 35 protruding to the inside of the opening 31.

Although not shown, the intermediate stoppers 53 (see FIG. 6A) that protrude from the release button 52 of the slider 50 are opposite to the inner surfaces (surfaces that face the puncture needle 20) of the thin-walled portions 35*a* (see FIG. 4B) of the stop protrusions 35.

Figure 16:
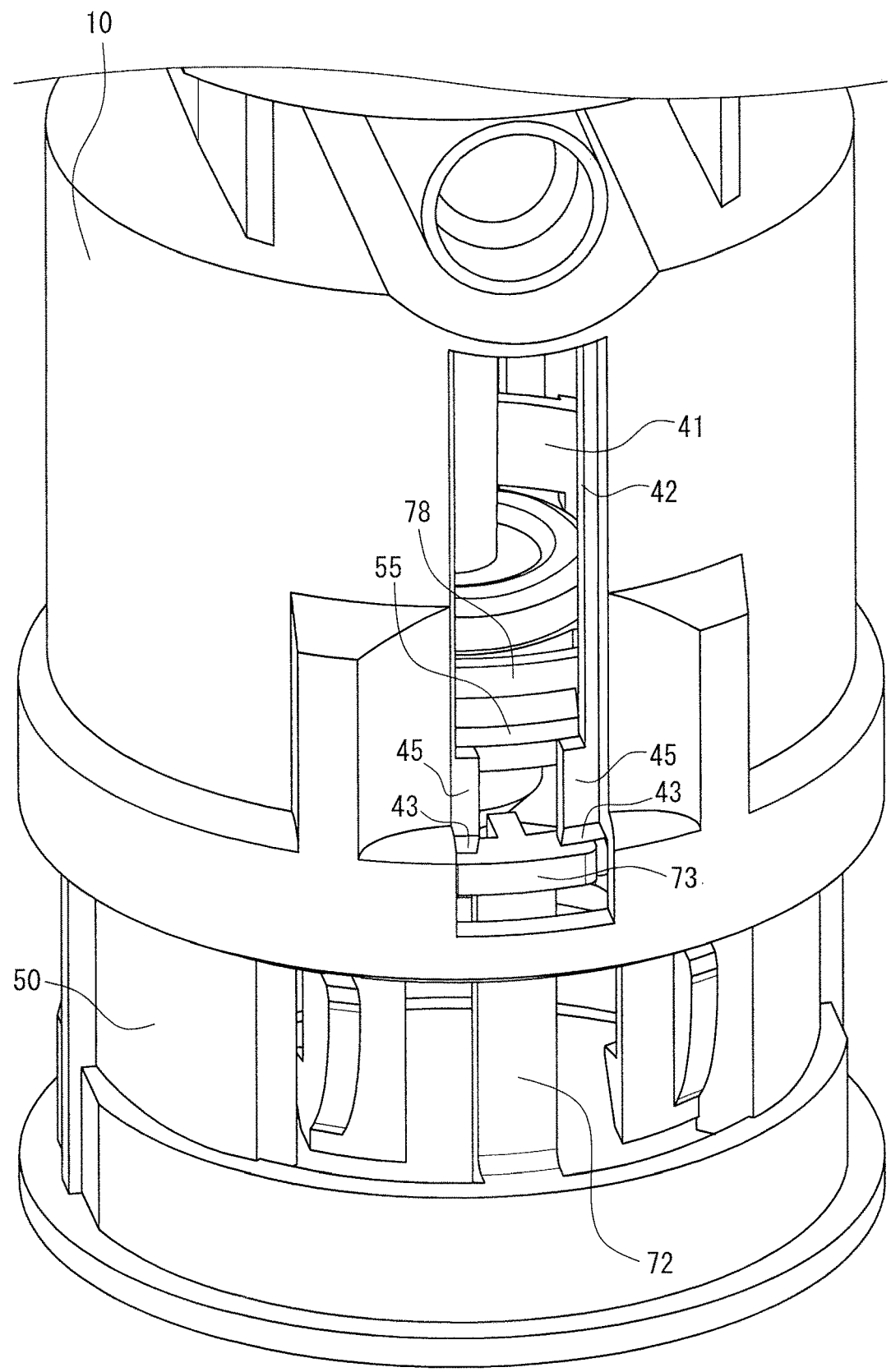
FIG. 16 is an enlarged perspective view of a rear-side opening of the connector main body of the connector according to Embodiment 1 of the present invention in the initial state.

FIG. 16 is an enlarged perspective view of the rear-side opening 41 of the connector main body 10. Similar to FIG. 15, the head portion 73, at the upper end, of the rear-side restricting arm 72 of the slider 50 is seen in the opening 41. The head portion 73 abuts, in the vertical direction, against the stop ends 43 that are each shared by the lower ends of the guide protrusion 42 and the stop protrusion 45 of the connector main body 10 that protrude into the opening 41.

The retaining protrusion 55 protruding from the rear upper frame 78 of the slider 50 is located above the stop protrusions 45 protruding to the inside of the opening 41.

As is understandable from FIGS. 15 and 16, the upper surfaces of the head portions 63 and 73 of the restricting arms 62 and 72 of the slider 50 abut, in the vertical direction, on the stop ends 33 and 43 of the connector main body 10. Accordingly, even if a compression force in the vertical direction is applied to the slider 50 and the connector main body 10 in this initial state, the head portions 63 and 73 of the restricting arms 62 and 72 will collide with the stop ends 33 and 43, thus making it impossible to insert the slider 50 into the connector main body 10.

Furthermore, the stop protrusions 35 and 45 of the connector main body 10 are arranged below the retaining protrusions 54 and 55 of the slider 50. Accordingly, even if a pulling force in the vertical direction is applied to the slider 50 and the connector main body 10 in this initial state, the retaining protrusions 54 and 55 will collide with the stop protrusions 35 and 45, thus making it impossible to drawn the slider 50 out of the connector main body 10. This prevents an erroneous operation in which the slider 50 and the connector main body 10 are separated from each other by mistake.

Accordingly, in the initial state in which the slider 50 is not mounted to a vial bottle 180, the slider 50 cannot move either upward or downward in the vertical direction (longitudinal direction of the puncture needle 20) with respect to the connector main body 10.

As shown in FIGS. 12A and 12B, the lock protrusions 67 and 77 that protrude outwardly from the outer surfaces of the grip arms 65 and 75 of the slider 50 are located below the lower end of the outer tube 12 of the connector main body 10.

2. Usage of Connector

Figure 17:
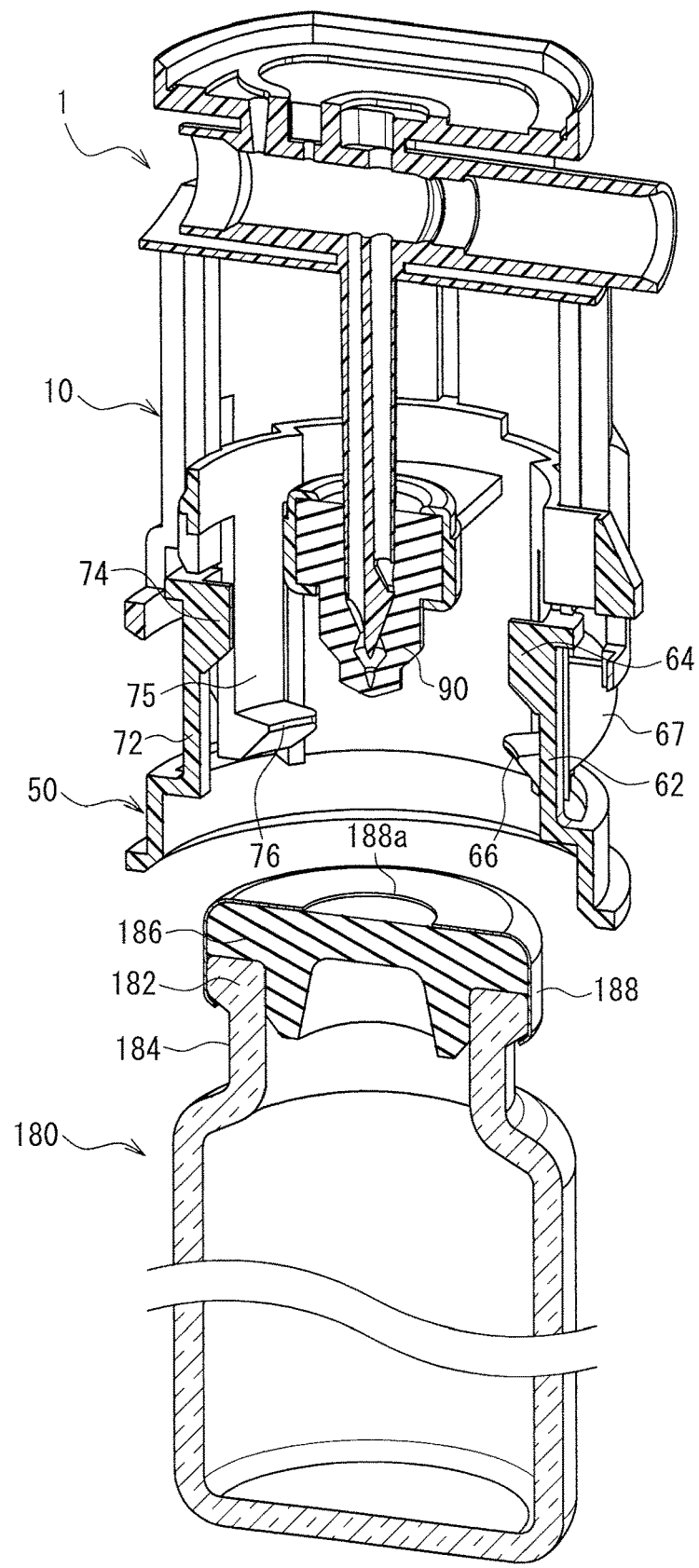
FIG. 17 is a perspective cross-sectional view illustrating a state immediately before the connector according to Embodiment 1 of the present invention is mounted to a vial bottle.

As shown in FIG. 17, the connector 1 of Embodiment 1 is mounted to the vial bottle 180, which serves as a drug container, and is used.

2.1. Vial bottle Configuration

Figure 18:
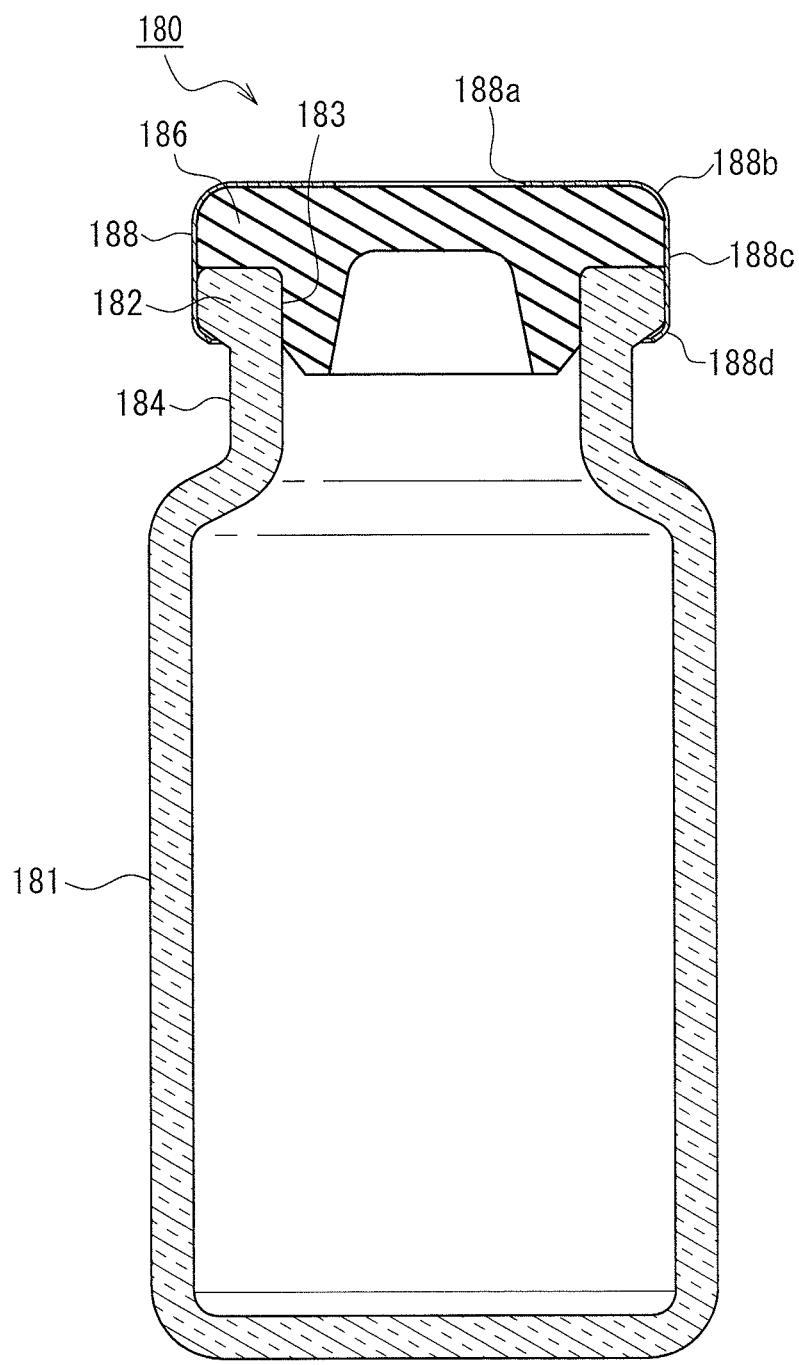
FIG. 18 is a cross-sectional view of the vial bottle to which the connector according to Embodiment 1 of the present invention is to be mounted.

FIG. 18 is a cross-sectional view of an example of the vial bottle 180. The vial bottle 180 is an closed container in which the plug (rubber plug) 186 is fitted to a mouth (opening) 183 enclosed by a flange 182 at the upper end of a bottle main body 181 so as to air-tightly and liquid-tightly seal the mouth 183, the plug 186 having almost the same outer diameter as that of the flange 182. The outer circumferential surface of the flange 182 is a substantially cylindrical surface that has a larger outer diameter than that of a portion (narrowed portion) 184 directly beneath the flange 182. Accordingly, an unevenness based on a difference in the outer diameter between the flange 182 and the narrowed portion 184 is formed between the flange 182 and the narrowed portion 184.

A cap 188 is mounted on the plug 186 and the flange 182, in order to prevent the plug 186 from falling out from the mouth 183 of the bottle main body 181. The cap 188 is made of a sheet of metal (for example, aluminum), a resin, or the like, and is in intimate contact with the plug 186 and the flange 182. The lower end of the cap 188 reaches below the outer circumferential surface of the flange 182 that is a substantially cylindrical surface. The upper end of the cap 188 even reaches the upper surface of the plug 186. A central region of the upper surface of the plug 186 is exposed to the outside via a circular opening 188a provided in the cap 188 (see FIG. 17).

The outer circumferential surfaces of the plug 186 and the flange 182 are cylindrical surfaces that have substantially the same diameter. Accordingly, also an outer circumferential surface 188c of the cap 188 that is mounted on them is a substantially cylindrical surface. The upper end of the outer circumferential surface 188c of the cap 188 is referred to as "upper edge 188b", and the lower end of the outer circumferential surface 188c is referred to as "lower edge 188d".

The vial bottle 180 does not need to be provided with the cap 188. In this case, the upper edge 188b, the lower edge 188d, and the outer circumferential surface 188c mean the corresponding portions of the plug 186 or the flange 182.

The vial bottle 180 contains a powdered medicine (not shown).

2.2. Mounting of Connector

The connector 1 is mounted to the vial bottle 180 in a manner that will be described below.

As shown in FIG. 17, the connector 1 in the initial state is opposite to the plug 186 of the vial bottle 180. Then, the cap 188 is inserted into the slider 50 of the connector 1, and the connector 1 is pressed against the vial bottle 180. The inscribed circle passing through the tips 66t and 76t (see FIGS. 7A, 7B, 8A, and 8B) of the claws 66 and 76 that protrude from the grip arms 65 and 75 of the slider 50 has a diameter that is smaller than the outer diameter of the cap 188 of the vial bottle 180. Accordingly, the inclined surfaces 66s and 76s (see FIGS. 7A, 7B, 8A, and 8B) of the claws 66 and 76 collide with the upper edge 188b (see FIG. 18) of the cap 188. The grip arms 65 and 75 elastically bend and deform so that the claws 66 and 76 are displaced outwardly as the connector 1 is pressed against the vial bottle 180. Since the lock protrusions 67 and 77 protruding from the outer surfaces of the grip arms 65 and 75 are located below the lower end of the outer tube 12 of the connector main body 10, the lock protrusions 67 and 77 do not collide with the connector main body 10 even if the grip arms 65 and 75 elastically bend and deform outwardly. The tips 66t and 76t of the claws 66 and 76 pass by the upper edge 188b of the cap 188, and then slide on the outer circumferential surface 188c (see FIG. 18) of the cap 188. When the tips 66t and 76t of the claws 66 and 76 pass beyond the lower edge 188d (see FIG. 18) of the cap 188, the grip arms 65 and 75 elastically recover, and the claws 66 and 76 are fitted to the narrowed portion 184, and engage with the flange 182. Accordingly, the connector 1 can be mounted to the vial bottle 180.

Since the claws 66 and 76 can be elastically displaced outwardly, and the claws 66 and 76 are provided with the inclined surfaces 66s and 76s, only by pressing the connector 1 against the vial bottle 180 in the above-described manner, it is possible to engage the claws 66 and 76 with the flange 182, and to mount the connector 1 to the vial bottle 180. Accordingly, the operability in mounting the connector 1 to the vial bottle 180 is favorable.

As described above, in the initial state, the relative movement of the slider 50 and the connector main body 10 in the longitudinal direction of the puncture needle 20 is restricted. Accordingly, even by applying a downward compression force for causing the claws 66 and 76 to engage with the flange 182 to the connector main body 10 instead of the slider 50, the slider 50 cannot move with respect to the connector main body 10. Also in this respect, the operability in mounting the connector 1 to the vial bottle 180 is favorable.

Figure 19:
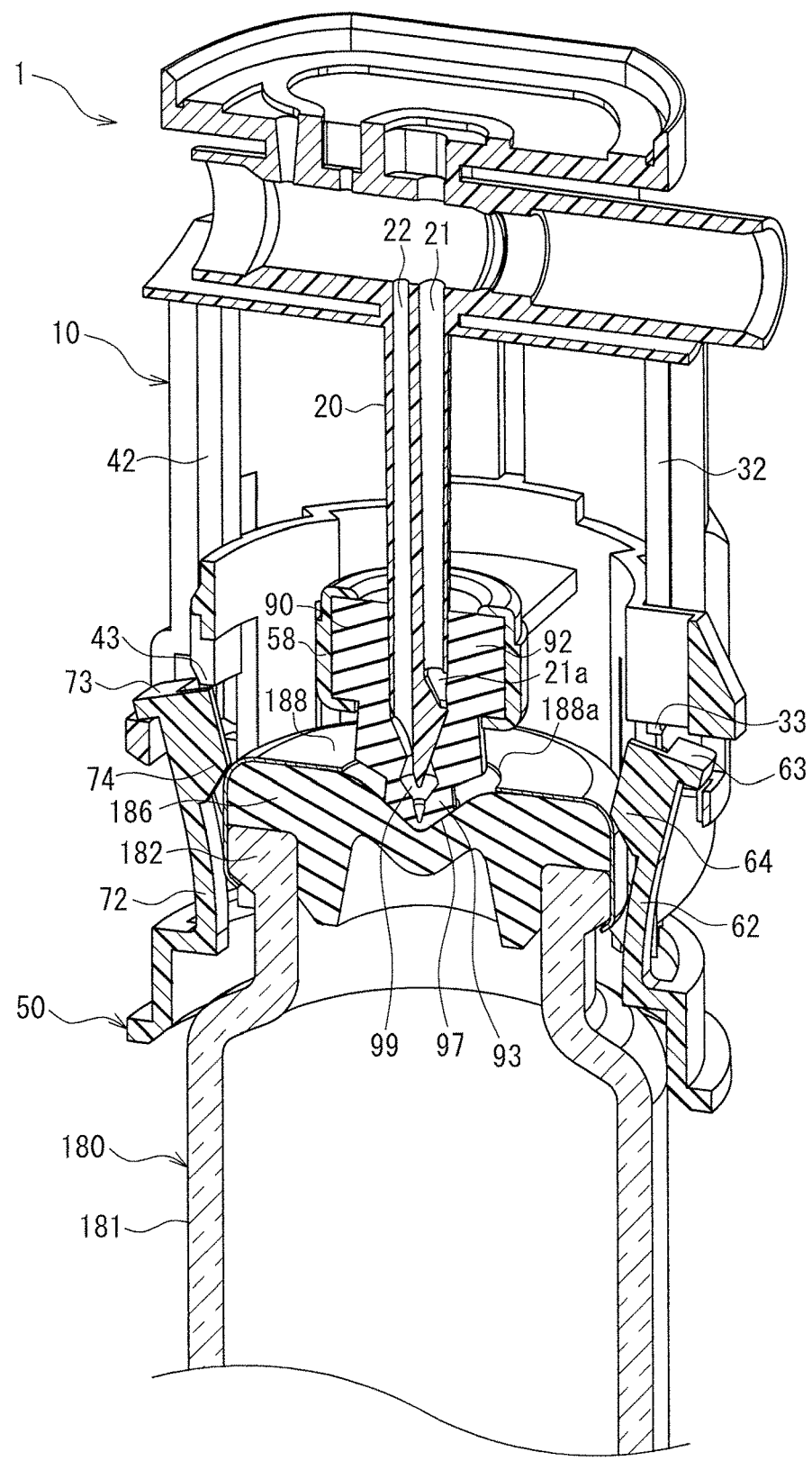
FIG. 19 is a perspective cross-sectional view illustrating a state immediately after claws of the connector according to Embodiment 1 of the present invention have engaged with a flange of the vial bottle.

FIG. 19 is a perspective cross-sectional view illustrating a state in which the claws 66 and 76 (not shown in FIG. 19) are engaged with the flange 182 of the vial bottle 180.

The projection surface 97 at the lower end (tip) of the cover 90 held by the slider 50 abuts against the upper surface of the plug 186 that is exposed via the opening 188a of the cap 188. The plug 186 is deformed slightly downward by a pressing force applied downward from the projection surface 97. The puncture needle 20 has not yet penetrated the cover 90 and the plug 186. In FIG. 19, the cover 90 is not substantially deformed, but the deformable region 93 (see FIGS. 10B and 14) of the cover 90 may be elastically compressed and deformed in the vertical direction.

Due to a variation in the size of the outer shapes of plugs 186, flanges 182, and caps 188, the position (height), in the vertical direction, of the upper surface of the plug 186 may be different between vial bottles 180. In this case, in addition to the amount of deformation of the plug 186, the amount of compression deformation in the vertical direction of the deformable region 93 of the cover 90 may change appropriately. Accordingly, it is possible to favorably bring the projection surface 97 of the cover 90 into intimate contact with the upper surfaces of the plugs 186 of vial bottles 180 having different sizes.

As is understandable from FIG. 17, the edges 64a and 74a (see FIGS. 7A, 7B, 8A, and 8B) of the abutting protrusions 64 and 74 of the restricting arms 62 and 72 of the slider 50 will collide with the upper edge 188b (see FIG. 18) of the cap 188 immediately before the claws 66 and 76 engage with the flange 182. Accordingly, when the claws 66 and 76 are engaged with the flange 182 as shown in FIG. 19, the restricting arms 62 and 72 are elastically bent and deformed so that the abutting protrusions 64 and 74 are displaced outwardly. The claws 66 and 76 of the slider 50, and the abutting protrusions 64 and 74 hold the cap 188 in the vertical direction. Accordingly, the slider 50 is positioned with respect to the vial bottle 180.

The edges 64a and 74a (see FIGS. 7A, 7B, 8A, and 8B) of the abutting protrusions 64 and 74 that abut against the cap 188 are inclined with respect to the vertical direction. Accordingly, even if, due to, for example, a variation in the outer size of plugs 186 or flanges 182, the distance between the upper edge 188b and the lower edge 188d of the cap 188, or the outer diameter of the outer circumferential surface 188c is different between vial bottles 180, the positions on the edges 64a and 74a against which the upper edge 188b abuts, or the amount of bending deformation of the restricting arms 62 and 72 will change according to the variation. Accordingly, an acceptable range for the size of the cap 188 to which the connector 1 can be mounted is broad.

Figure 20:
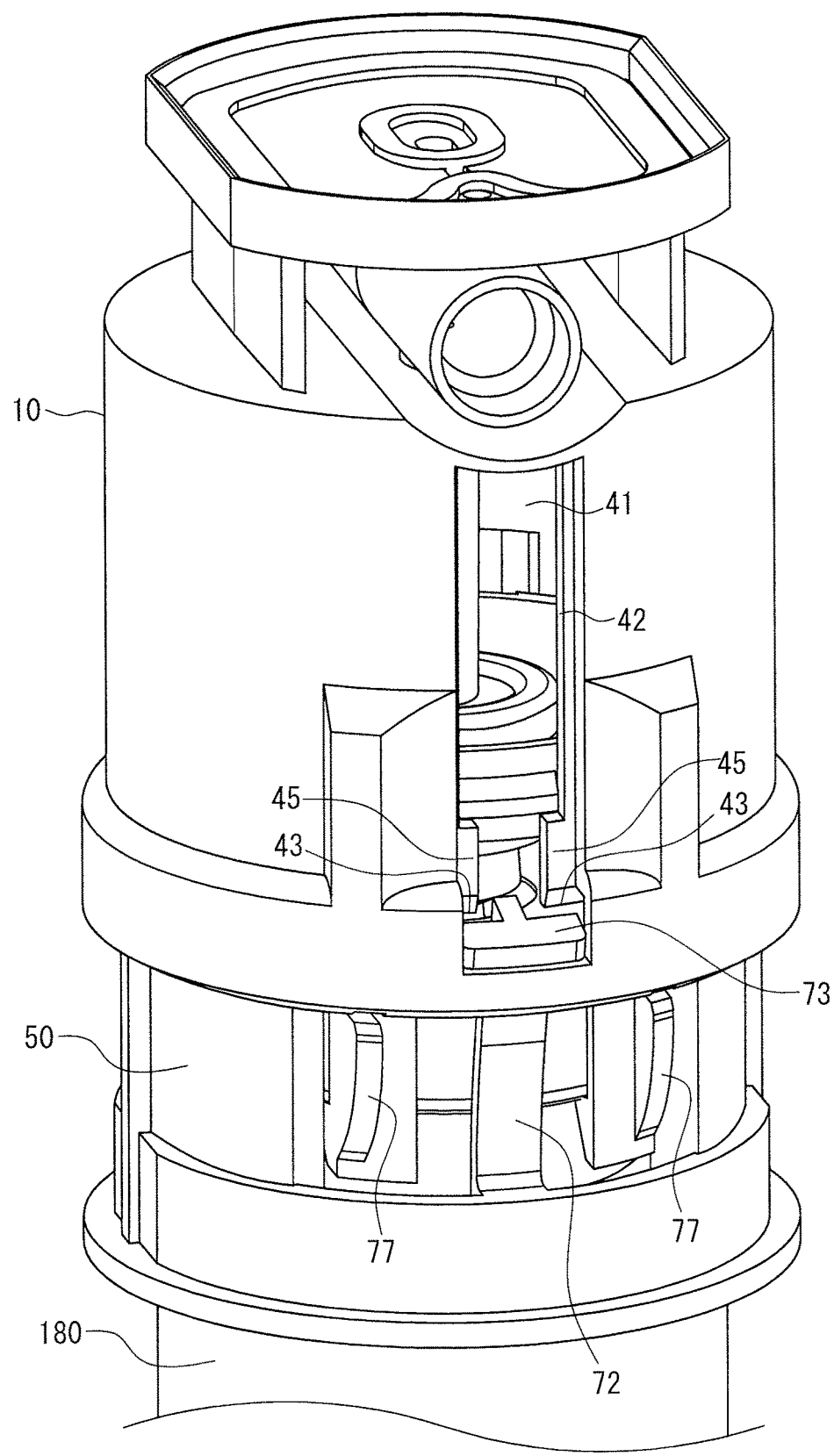
FIG. 20 is an enlarged perspective view of the rear-side opening of the connector main body in the state immediately after the claws of the connector according to Embodiment 1 of the present invention have engaged with the flange of the vial bottle.

FIG. 20 is an enlarged perspective view of the rear-side opening 41 of the connector main body 10 of the connector 1 in the state of FIG. 19. The head portion 73, at the upper end, of the rear-side restricting arm 72 of the slider 50 is seen in the opening 41. Since the restricting arm 72 is elastically bent and deformed, the head portion 73 is displaced outwardly. As is understandable from the comparison with FIG. 16, the head portion 73 is located further outward than the stop ends 43 at the lower ends of the guide protrusions 42 of the connector main body 10.

Although the illustration is omitted, also in the front-side opening 31 of the connector main body 10 (see FIG. 15), the restricting arm 62 is elastically bent and deformed, and as a result thereof, the head portion 63 of the restricting arm 62 is located further outward than the stop ends 33 at the lower ends of the guide protrusions 32 of the connector main body 10.

Accordingly, when the claws 66 and 76 of the slider 50 are engaged with the flange 182 of the vial bottle 180, the restricting arms 62 and 72 are elastically bent and deformed, and the collision between the head portions 63 and 73 at the upper ends thereof and the stop ends 33 and 43 of the connector main body 10 is released. Accordingly, in this state, by applying a compression force in the vertical direction to the connector main body 10 and the vial bottle 180 so that they approach each other, it is possible for the slider 50 and the vial bottle 180 to enter the connector main body 10 while keeping the relative positional relationship between the vial bottle 180 and the slider 50 constant.

2.3. Puncture of Puncture Needle

In the state shown in FIG. 19, the connector main body 10 is pressed against the vial bottle 180. The slider 50 that is holding the vial bottle 180 moves with respect to the connector main body 10 so as to be stored in the connector main body 10.

The abutting protrusions 64 and 74 of the restricting arms 62 and 72 of the slider 50 collide with the upper edge 188b of the cap 188. Accordingly, even by applying a compression force in the vertical direction to the connector main body 10 and the vial bottle 180, the relative positional relationship between the vial bottle 180 and the slider 50 does not substantially change, and the slider 50 moves with respect to the connector main body 10.

Before the slider 50 moves with respect to the connector main body 10, the intermediate stoppers 53 (see FIG. 6A) that protrude from the side surfaces of the release button 52 of the slider 50 are opposite to the inner surfaces of the thin-walled portions 35a (see FIG. 4B) of the stop protrusions 35 of the connector main body 10. After the slider 50 starts moving with respect to the connector main body 10, the intermediate stoppers 53 of the slider 50 slide on the inclined surfaces 35b (see FIG. 4B) of the stop protrusions 35 of the connector main body 10. At this time, the front upper frame 68 slightly and elastically bends and deforms so that the release button 52 moves inwardly. When the intermediate stoppers 53 pass by the upper ends of the inclined surfaces 35b, and move beyond the stop protrusions 35, the front upper frame 68 elastically recovers, and the release button 52 is slightly displaced outwardly and reverts to the initial position.

When the slider 50 moves with respect to the connector main body 10, the intermediate stoppers 53 (see FIG. 6A) that protrude from both side surfaces of the release button 52 of the slider 50 slide on the tip surfaces of the pair of guide protrusions 32 protruding to the inside of the opening 31 of the connector main body 10 (surfaces of the guide protrusions 32 that are opposite to the counterpart guide protrusion 32). The head portions 63 and 73 protruding in the circumferential direction of the restricting arms 62 and 72 of the slider 50 slide on the outer side surfaces of the guide protrusions 32 and 42 (see FIGS. 4A and 4B) protruding to the inside of the openings 31 and 41 of the connector main body 10. Furthermore, the lock protrusions 67 and 77 protruding outwardly from the outer surfaces of the grip arms 65 and 75 of the slider 50 are stored in the grooves 17 formed in the inner circumferential surface of the connector main body 10 (see FIGS. 12A and 12B).

When, in the state of FIG. 19, the slider 50 enters the connector main body 10, the puncture needle 20 provided on the connector main body 10 relatively moves downward to the cover 90 and the vial bottle 180 that are held by the slider 50. The puncture needle 20 reaches the slit 95 at the tip of the cover 90, and penetrates. Then, the puncture needle 20 punctures the plug 186 of the vial bottle 180 and penetrates. The guide portion 93b (see FIG. 10B) provided in the inner cavity 91 of the cover 90 functions to guide the tip 20t of the puncture needle 20 to the slit 95.

Figure 21:
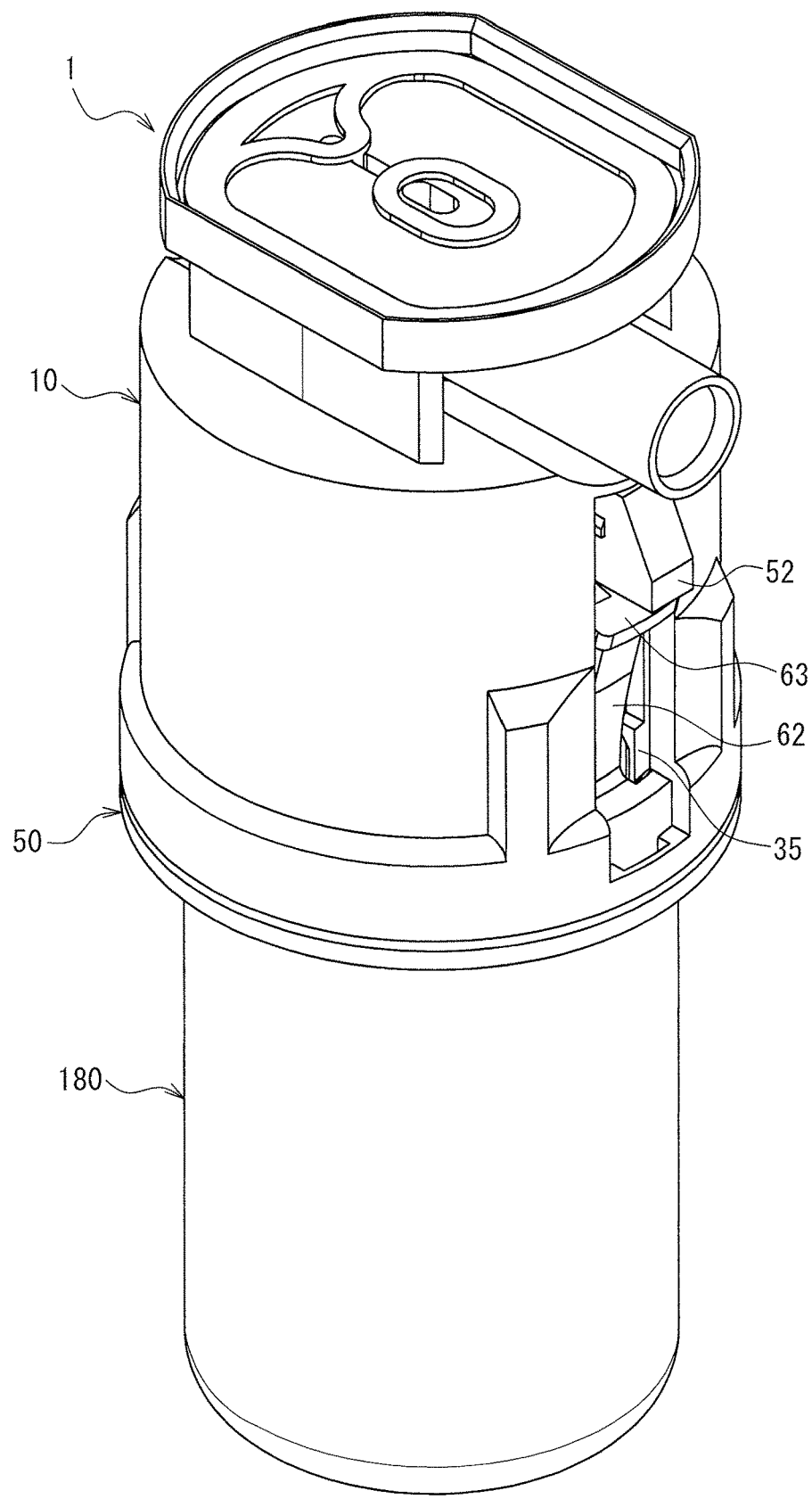
FIG. 21 is a perspective view illustrating a state in which the puncture needle of the connector according to Embodiment 1 of the present invention has punctured a plug of the vial bottle.
Figure 22:
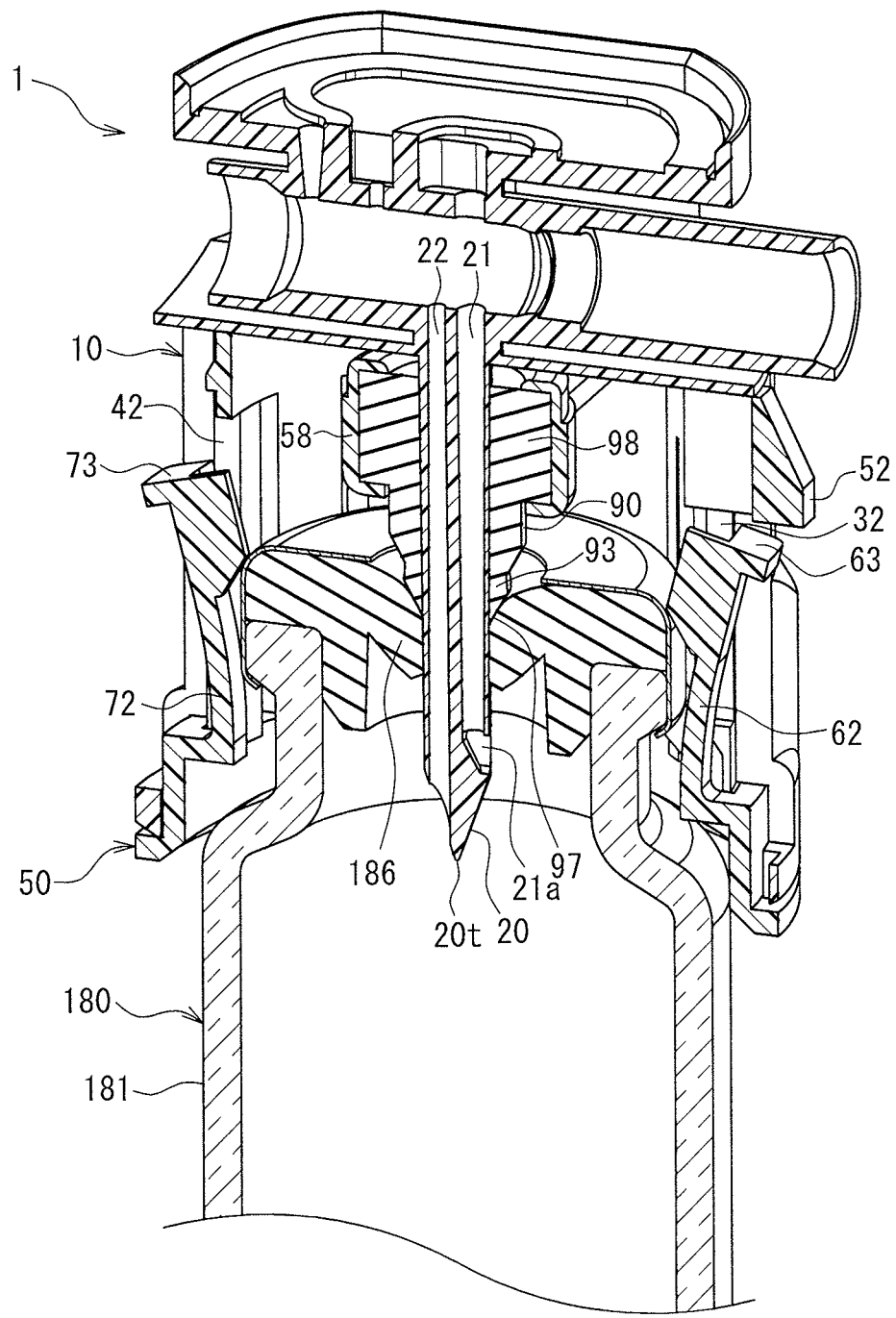
FIG. 22 is a perspective cross-sectional view illustrating the state in which the puncture needle of the connector according to Embodiment 1 of the present invention has punctured the plug of the vial bottle.

FIG. 21 is a perspective view illustrating a state in which the slider 50 has entered the deepest portion of the connector main body 10, and FIG. 22 is a perspective cross-sectional view thereof.

As shown in FIG. 22, the puncture needle 20 penetrates the slit 95 formed at the tip (lower end) of the cover 90, and further penetrates the plug 186. When the puncture needle 20 penetrates the cover 90 and the plug 186, the cover 90 and the plug 186 are subjected to a downward force from the puncture needle 20. Accordingly, the plug 186 largely deforms to the bottle main body 181 side due to being penetrated by the puncture needle 20. Also the cover 90 is largely deformed downward while keeping the state in which the projection surface 97 is in intimate contact with the plug 186, so that the initial shape (see FIGS. 10A, 10B, and 14) is not recognized. Since the hold portion 98 of the cover 90 is held by the holder 58 of the slider 50, the distance, in the vertical direction, from the hold portion 98 to the vial bottle 180 is substantially the same between before (FIG. 19) and after (FIG. 22) the puncturing by the puncture needle 20. Accordingly, the deformable region 93 (see FIGS. 10A and 14) of the cover 90 is extended downward conforming to the deformation of the plug 186. The closed space 99 (see FIG. 14) that was formed in the deformable region 93 has disappeared almost completely.

The openings, on the tip 20*t* side, that are respectively in communication with the liquid flow channel 21 and the gas flow channel 22 of the puncture needle 20 are exposed to the inside of the vial bottle 180. In this state, via the liquid flow channel 21 and the lateral hole 21*a*, it is possible to let liquid (for example, a dissolving solution) flow into the vial bottle 180 and to let liquid (for example, a drug solution obtained by dissolving a medicine) in the vial bottle 180 flow out of the vial bottle 180. When liquid flows into and out of the vial bottle 180, air flows into and out of the vial bottle 180 via the gas flow channel 22. This reduces a change in atmospheric pressure in the vial bottle 180, and makes it easy for liquid to be taken in and out.

In the present invention, the "punctured state" refers to the state shown in FIGS. 21 and 22 in which the puncture needle 20 has punctured the plug 186. The "punctured position" refers to the position of the slider 50 with respect to the connector main body 10 in the punctured state.

2.4. Drawing of Puncture Needle

After liquid has been taken in and out of the vial bottle 180 via the puncture needle 20, the puncture needle 20 is drawn from the plug 186. That is, in the punctured state shown in FIGS. 21 and 22, the connector main body 10 and the vial bottle 180 are drawn in the vertical direction so as to be separated from each other.

The claws 66 and 76 of the slider 50 are engaged with the flange 182 of the vial bottle 180. Accordingly, by drawing the vial bottle 180 downward, the slider 50, together with the vial bottle 180, is drawn out of the connector main body 10. In this process, since the relative positional relationship between the slider 50 and the vial bottle 180 does not substantially change, also the relative positional relationship between the cover 90 and the vial bottle 180 does not substantially change.

The lock protrusions 67 and 77 protrude from the surfaces of the grip arms 65 and 75 of the slider 50 that face away from the claws 66 and 76. The lock protrusions 67 and 77 are stored in the grooves 17 formed in the inner circumferential surface of the connector main body 10. Since the lock protrusions 67 and 77 collide with the bottom surfaces of the grooves 17, the grip arms 65 and 75 cannot elastically bend and deform so that the claws 66 and 76 are displaced outwardly. Accordingly, the claws 66, 76 and the flange 182 are not disengaged even if the vial bottle 180 is drawn to separate from the connector main body 10.

In such a state in which the slider 50 is stored in the connector main body 10, the connector main body 10 collides with the grip arms 65 and 75 including the lock protrusions 67 and 77, thus preventing the grip arms 65 and 75 from bending and deforming outwardly. In other words, the elastically bendable and deformable grip arms 65 and 75 on which the claws 66 and 76 are formed, and the connector main body 10 that restricts the bending deformation of the grip arms 65 and 75 constitute a "lock mechanism" for preventing disengagement between the claws 66, 76 and the flange 182. As a result of the connector 1 being provided with the lock mechanism, it is possible to stably perform the operation of drawing of the puncture needle 20 by the application of a pulling force to the connector main body 10 and the vial bottle 180 in the punctured state. No erroneous operation in which the claws 66, 76 and the flange 182 are disengaged will occur during the drawing operation. Note that in Embodiment 1, the lock protrusions 67 and 77 protrude from the outer side surfaces of the grip arms 65 and 75, but even without the lock protrusions 67 and 77, a lock mechanism for preventing disengagement of the claws 66, 76 and the flange 182 can be configured by the connector main body 10 restricting the grip arms 65 and 75 from bending and deforming.

Figure 23:
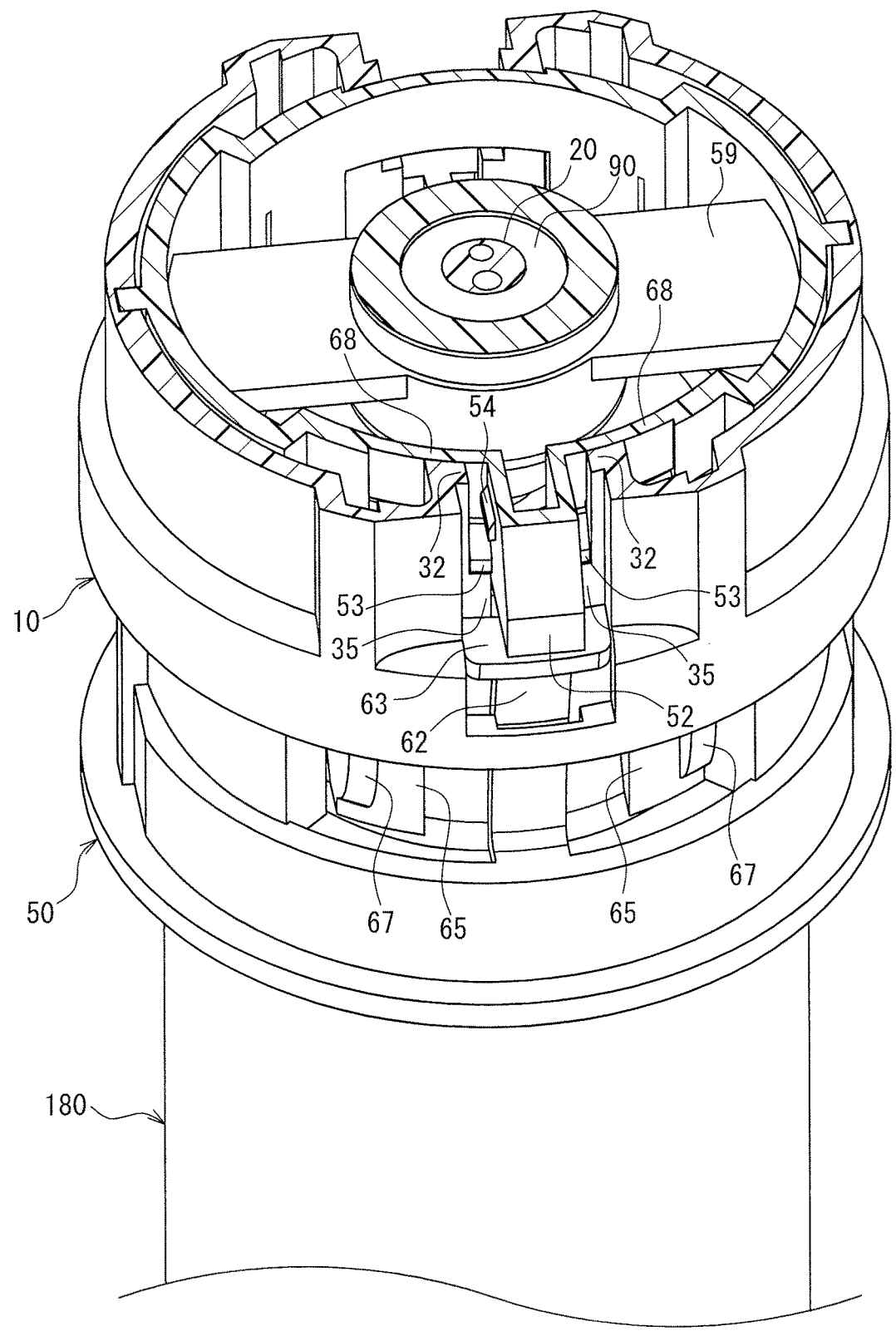
FIG. 23 is an enlarged perspective cross-sectional view of the connector according to Embodiment 1 of the present invention in which the slider is located at an intermediate stop position.

As shown in FIG. 23, in the process in which the slider 50 is drawn out of the connector main body 10, the intermediate stoppers 53 that protrude from both side surfaces of the release button 52 of the slider 50 collide with the upper ends of the stop protrusions 35 that protrude to the inside of the front-side opening 31 of the connector main body 10. When the intermediate stoppers 53 have collided with the stop protrusions 35, it is impossible to move the slider 50 further downward with respect to the connector main body 10. In the process in which the slider 50 is drawn out of the connector main body 10, the "intermediate stop position" refers to the position of the slider 50 with respect to the connector main body 10 at which the slider 50 cannot be further drawn out of the connector main body 10.

Figure 24:
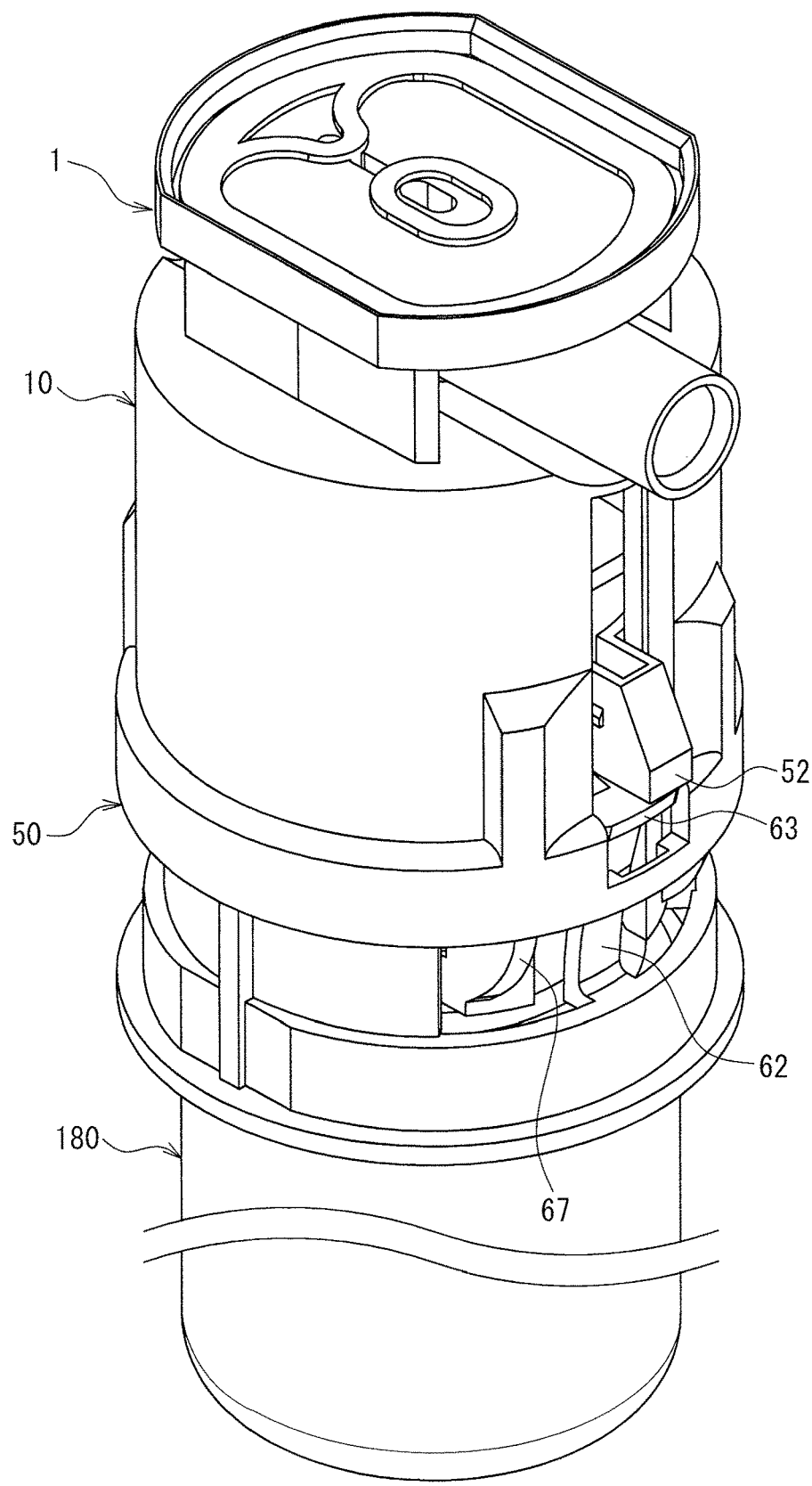
FIG. 24 is a perspective view of the connector according to Embodiment 1 of the present invention in which the slider is located at the intermediate stop position.
Figure 25:
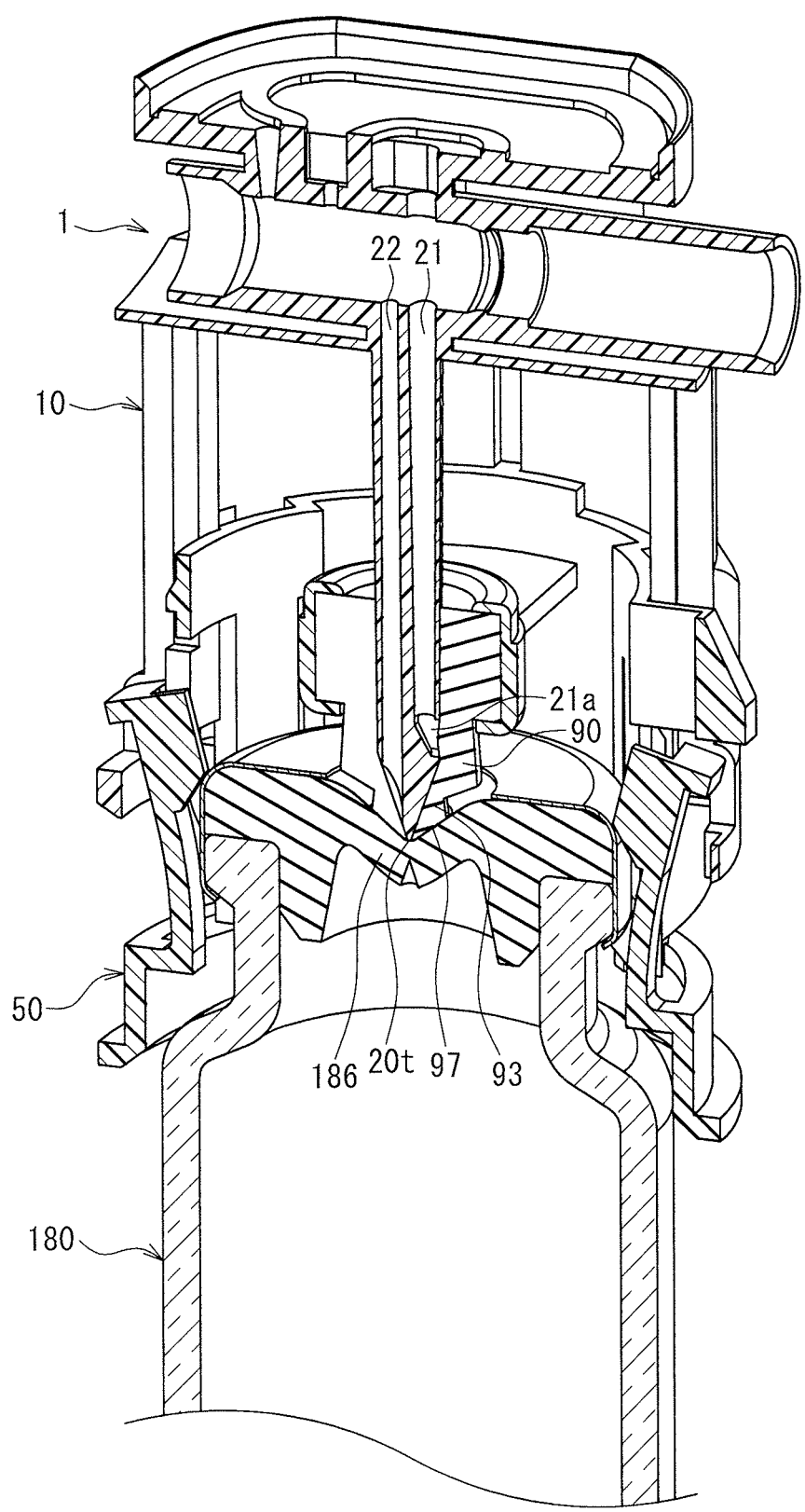
FIG. 25 is a perspective cross-sectional view of the connector according to Embodiment 1 of the present invention in which the slider is located at the intermediate stop position.

FIG. 24 is a perspective view of the connector 1 in which the slider 50 is at the intermediate stop position, and FIG. 25 is a perspective cross-sectional view thereof.

As shown in FIG. 24, when the slider 50 is at the intermediate stop position, the lock protrusions 67 (see FIG. 6A) that protrude outwardly from the outer surface of the grip arms 65 of the slider 50 are still stored in the grooves 17 formed in the inner circumferential surface of the connector main body 10. Similarly, also the lock protrusions 77 (see FIG. 6B), although the illustration thereof is omitted, that protrude from the rear-side grip arms 75 are still stored in the grooves 17 of the connector main body 10. Accordingly, the above-described lock mechanism functions also at the intermediate stop position.

As shown in FIG. 25, the puncture needle 20 is almost drawn out of the plug 186. The tip 20*t* of the puncture needle 20 is positioned in the slit 95 (see FIG. 10B) of the cover 90. The projection surface 97 at the lower end of the cover 90 is in intimate contact with the upper surface of the plug 186, and is pressing the plug 186 downward. The plug 186 is subjected to the pressing force from the projection surface 97 of the cover 90, and the portion of the plug 186 that has been punctured by the puncture needle 20 is deformed downward. The deformable region 93 of the cover 90 is extended slightly downward as compared to the case of the initial state (see FIG. 14). The closed space 99 (see FIG. 14) that was formed in the deformable region 93 can still hardly be recognized.

Figure 26:
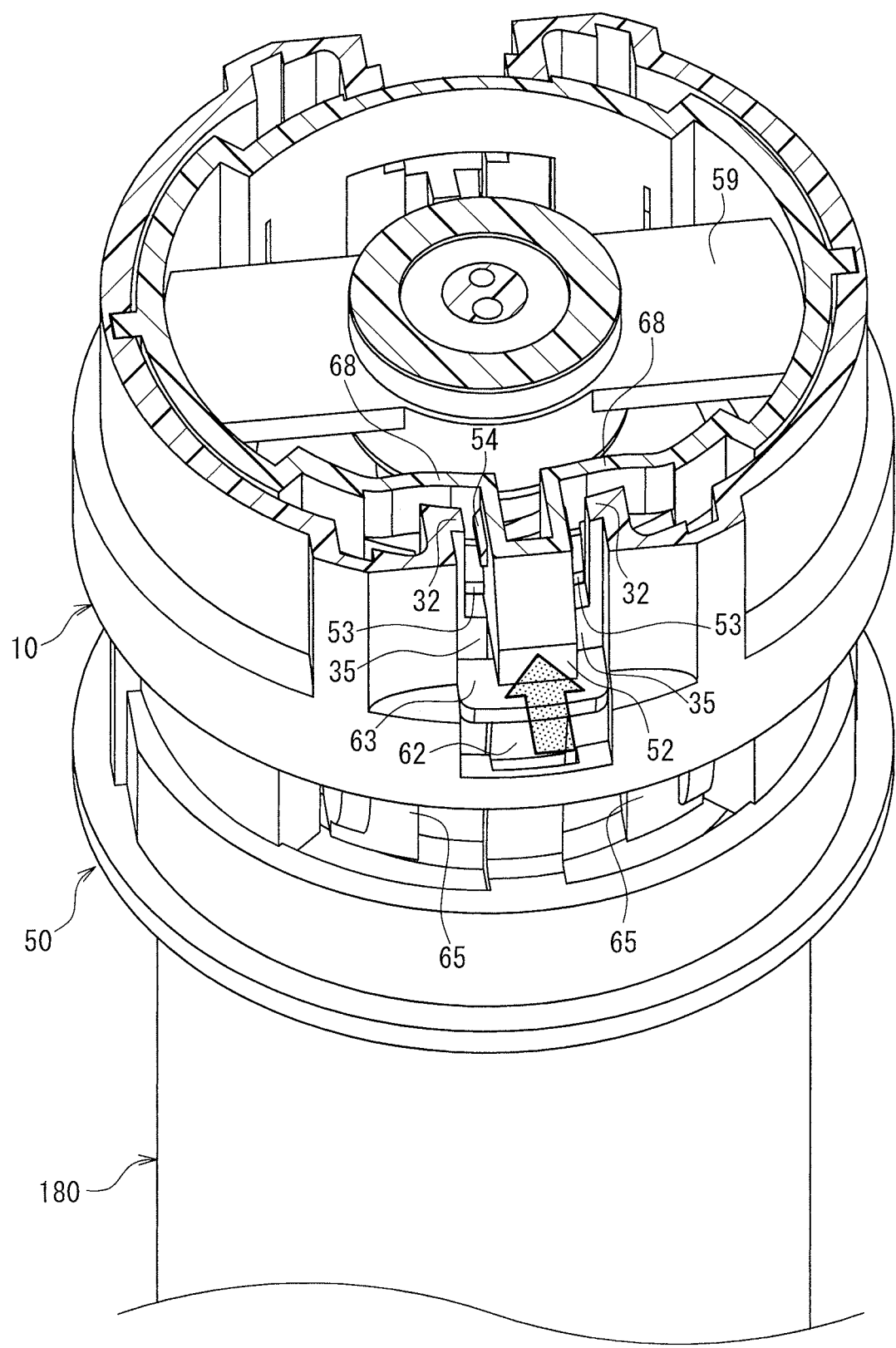
FIG. 26 is an enlarged perspective cross-sectional view illustrating a state in which pressing a release button releases collision between intermediate stoppers and stop protrusions when the slider is located at the intermediate stop position.

In the state in which the slider 50 is at the intermediate stop position (FIGS. 23 to 25), the release button 52 is pressed inwardly as shown in FIG. 26. As is easily understandable from the comparison between FIG. 26 and FIG.

23, when the release button 52 is pressed, the front upper frame 68 that holds the release button 52 elastically deforms, and the release button 52 and the intermediate stoppers 53 on both side surfaces thereof are displaced inwardly. Accordingly, the collision between the intermediate stoppers 53 and the stop protrusions 35 is released. As a result, the slider 50 becomes movable further downward with respect to the connector main body 10.

By drawing the vial bottle 180 further downward with respect to the connector main body 10 while pressing the release button 52, it is possible to further drawn the vial bottle 180 and the slider 50 mounted thereto out of the connector main body 10. It is possible to drawn the vial bottle 180 and the slider 50 until the retaining protrusions 54 and 55 (see FIGS. 6A and 6B) of the slider 50 collide with the stop protrusions 35 and 45 (see FIGS. 2A and 2B) of the connector main body 10.

Figure 27:
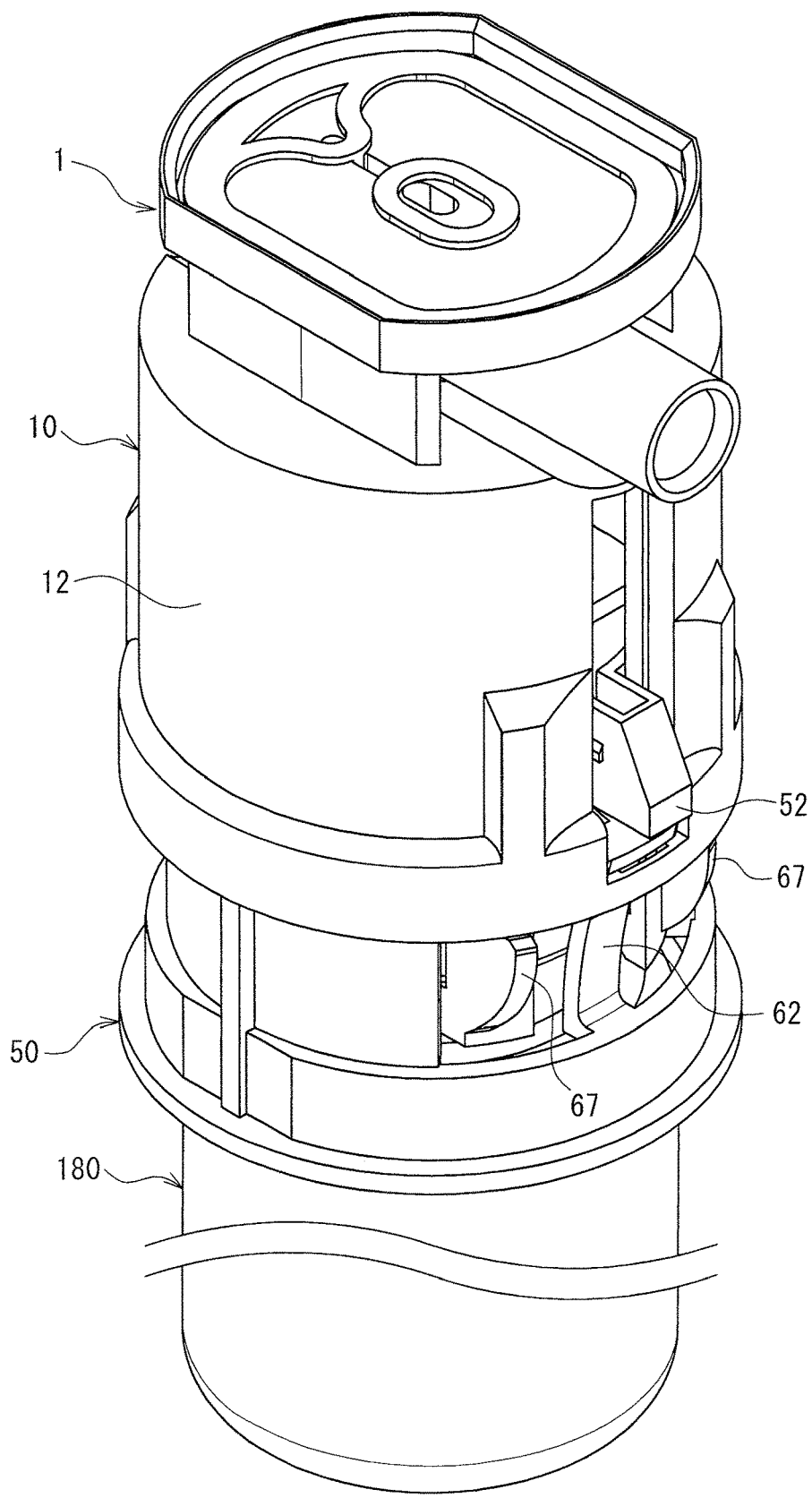
FIG. 27 is a perspective view of the connector according to Embodiment 1 of the present invention in which the slider is drawn, to the maximum, from the connector main body.
Figure 28:
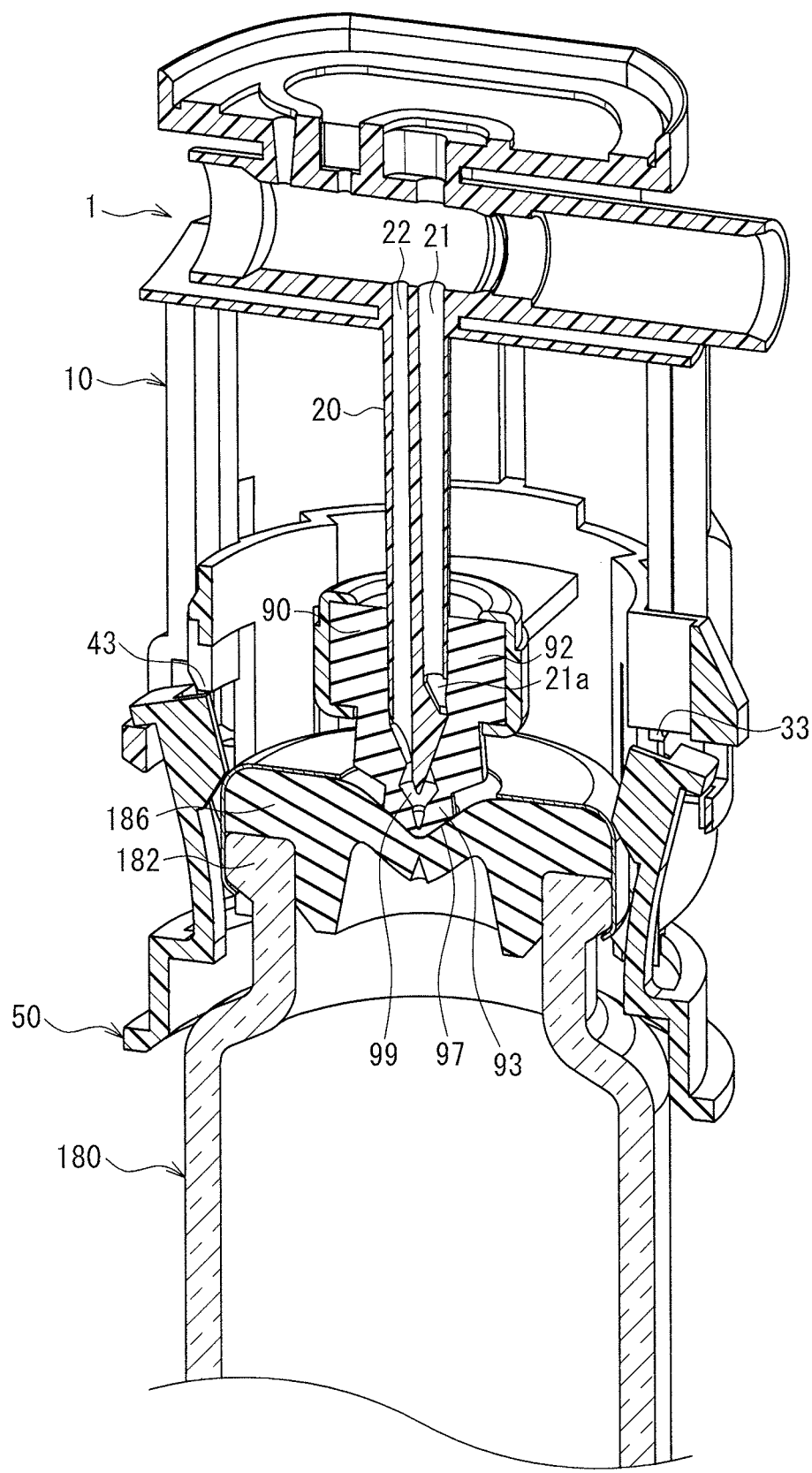
FIG. 28 is a perspective cross-sectional view of the connector according to Embodiment 1 of the present invention in which the slider is drawn, to the maximum, from the connector main body.

FIG. 27 is a perspective view illustrating the state in which the vial bottle 180 and the slider 50 are drawn, to the maximum, out of the connector main body 10, and FIG. 28 is a perspective cross-sectional view thereof. The relative positional relationship of the vial bottle 180 and the slider 50 to the connector main body 10 is the same as that in the state immediately after the connector 1 is mounted to the vial bottle 180 (FIG. 19).

As is understandable from FIG. 27, the lock protrusions 67 and 77 (in FIG. 27, the lock protrusions 77 cannot be seen) that protrude from the outer surfaces of the grip arms 65 and 75 of the slider 50 are located below the lower end of the outer tube 12 of the connector main body 10. Accordingly, the grip arms 65 and 75 can elastically bend and deform outwardly. In other words, the "lock mechanism" for preventing disengagement between the claws 66, 76 and the flange 182 does not function. The "unlocked position" refers to the position of the slider 50 with respect to the connector main body 10 at which the lock mechanism does not function, the "unlocked position" being shown in FIGS. 27 and 28.

As shown in FIG. 28, the puncture needle 20 is stored in the seal region 92 of the cover 90. The opening of the lateral hole 21a of the puncture needle 20 (and preferably also the opening of the gas flow channel 22) is closed by the inner circumferential surface of the inner cavity 91 (see FIG. 10B) of the cover 90. The shapes of the cover 90 and the plug 186 are substantially the same as those in FIG. 19. The projection surface 97 at the lower end (tip) of the cover 90 abuts against the plug 186. The plug 186 is subjected to the downward pressing force from the projection surface 97, and is slightly deformed downward. The closed space 99 has reverted in the deformable region 93 of the cover 90. In FIG. 28, the cover 90 is not substantially deformed, but the deformable region 93 of the cover 90 may be elastically compressed and deformed in the vertical direction. Furthermore, due to the compression deformation of the deformable region 93, the closed space 99 is also compressed, and its volume may be reduced to be smaller than that in the initial state (see FIGS. 13 and 14).

2.5. Separation of Connector and Vial Bottle

In the state in which the slider 50 is at the unlocked position (FIGS. 27 and 28), the vial bottle 180 is drawn downward from the connector 1. The claws 66 and 76 of the slider 50 are engaged with the flange 182 of the vial bottle 180. The lock protrusions 67 and 77 that protrude from the outer surfaces of the grip arms 65 and 75 at which the claws 66 and 76 are formed are located below the lower end of the outer tube 12. Accordingly, the grip arms 65 and 75 can elastically bend and deform outwardly. Due to the vial bottle 180 being drawn, the claws 66 and 76 move outwardly along an inclined conical surface below the flange 182.

Figure 29:
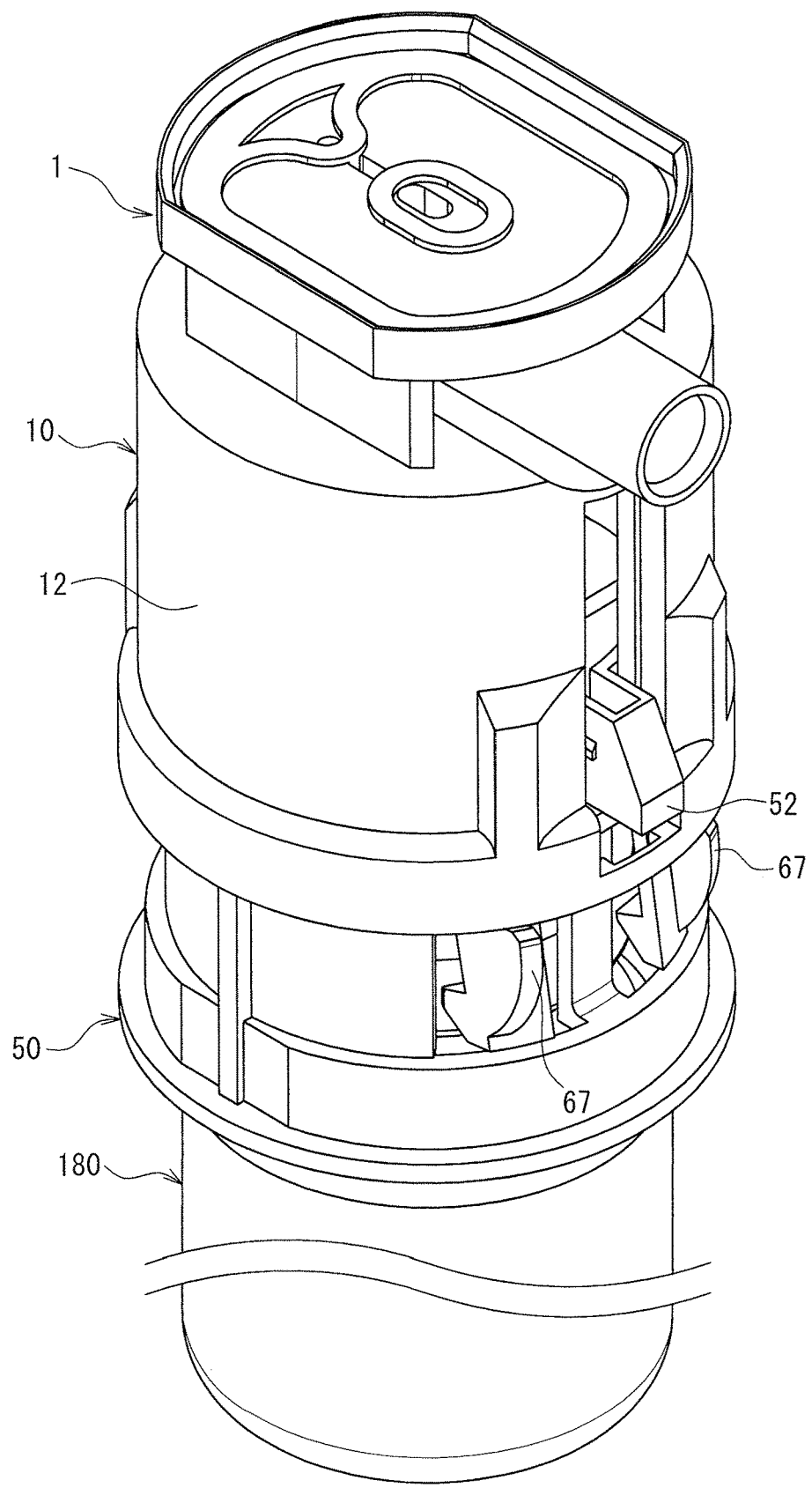
FIG. 29 is a perspective view illustrating a state in which, according to Embodiment 1 of the present invention, the claws of the slider slide on the outer circumferential surface of a cap mounted on the vial bottle.
Figure 30:
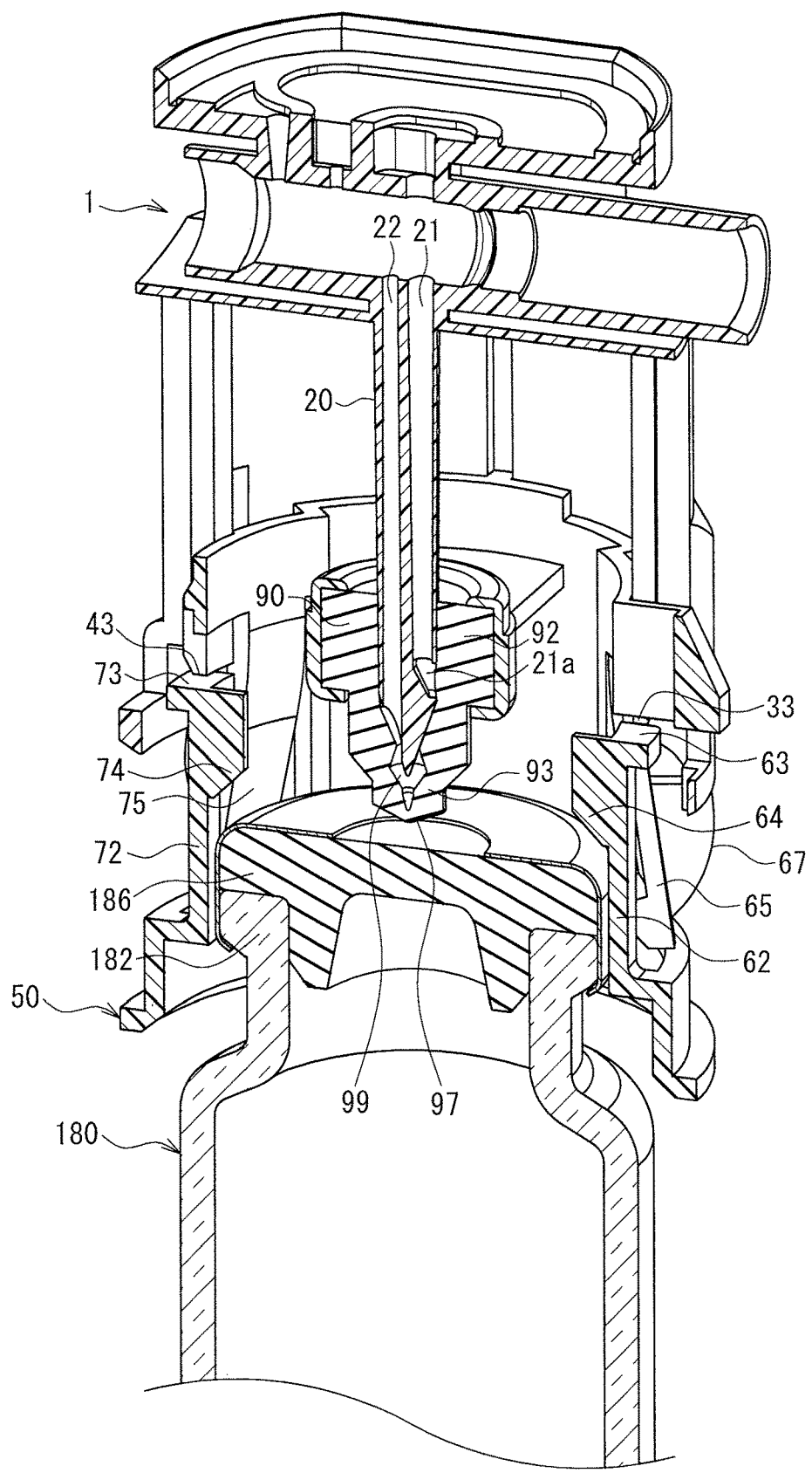
FIG. 30 is a perspective cross-sectional view illustrating the state shown in FIG. 29.

FIG. 29 is a perspective view illustrating a state in which the claws 66 and 76 have passed beyond the lower edge 188d of the cap 188 of the vial bottle 180, and slide on the outer circumferential surface 188c (see FIG. 18) of the cap 188. FIG. 30 is a perspective cross-sectional view of the state of FIG. 29. As shown in FIG. 30, the cover 90 is separated from the plug 186 of the vial bottle 180. Both the cover 90 and the plug 186 have reverted to the initial state (see FIGS. 13 and 17). The abutting protrusions 64 and 74 of the restricting arms 62 and 72 of the slider 50 are distanced from the cap 188. Therefore, the restricting arms 62 and 72 have moved inwardly and have reverted to the positions in the initial state. As a result, similar to the initial state shown in FIGS. 15 and 16, the head portions 63 and 73 of the restricting arms 62 and 72 collide with the stop ends 33 and 43 in the vertical direction.

As described above, when the slider 50 reaches the unlocked position (see FIGS. 27 and 28) with respect to the connector main body 10, the retaining protrusions 54 and 55 (see FIGS. 6A and 6B) of the slider 50 collide with the stop protrusions 35 and 45 (see FIGS. 2A and 2B) of the connector main body 10. Accordingly, in the operation of separating the connector 1 from the vial bottle 180 that is shown in FIGS. 29 and 30, even by applying a pulling force to the connector main body 10 instead of the slider 50, it is possible to separate the connector 1 from the vial bottle 180 while keeping the relative positional relationship between the connector main body 10 and the slider 50 substantially constant.

As a result, it is possible to separate the vial bottle 180 from the connector 1. A new vial bottle 180 is connected to the connector 1, and the above-described operation is repeated, if the need arises. Then, the used connector 1 that was in touch with a dangerous medicine will be discarded.

3. Functions

As described above, the connector 1 of Embodiment 1 is provided with the cover 90 for covering the openings on the tip 20t side that are respectively in communication with the flow channels 21 and 22 of the puncture needle 20. The puncture needle 20 is provided on the connector main body 10, and the cover 90 is held by the slider 50. The slider 50 is a member separate from the connector main body 10, and is movable with respect to the connector main body 10 in the longitudinal direction of the puncture needle 20. The slider 50 is provided with the claws 66 and 76 for engaging with the flange 182 of the vial bottle 180. Accordingly, once the claws 66 and 76 of the slider 50 are engaged with the flange 182 of the vial bottle 180, the relative positional relationship between the cover 90 and the vial bottle 180 is substantially constant until the claws 66, 76 and the flange 182 are disengaged. The puncture needle 20 moves with respect to the above-described cover 90 and vial bottle 180.

The cover of above-described Patent Document 2 is fixed to the base substrate that holds the male member. Accordingly, the cover and the male member are displaced together. A case in which such a cover is applied to a puncture needle that punctures a plug of a vial bottle is considered. In this case, when the puncture needle is drawn from the plug, the cover is separated from the plug at the same time. Since the cover moves together with the puncture needle, a situation may occur in which the cover cannot immediately revert to the initial shape if, for example, the puncture needle is quickly drawn from the plug. In this case, a drug solution may leak to the outside from an opening, on the tip side, of a flow channel of the puncture needle by the time the opening of the flow channel is covered by the cover.

In contrast thereto, in the connector 1 according to the present embodiment, the position of the cover 90 is substantially fixed with respect to the plug 186, as long as the claws 66 and 76 are engaged with the flange 182 of the vial bottle 180. Accordingly, when the puncture needle 20 is drawn from the plug 186, the cover 90 reliably moves with respect to the puncture needle 20. As a result, the opening (that is, the opening of the lateral hole 21a), on the tip 20t side, of the liquid flow channel 21 of the puncture needle 20 drawn from the plug 186 can be stored in the cover 90 without being exposed to the outside. This will reduce the likelihood of the occurrence of a situation in which a drug solution leaks from the opening, on the tip 20t side, of the liquid flow channel 21 due to the puncture needle 20 drawn from the plug 186 not being covered by the cover 90. Thus, according to the connector 1 of the present invention, it is possible to reduce the likelihood of a drug solution leaking to the outside after the connector 1 and the vial bottle 180 are separated from each other.

The tip of the cover of above-described Patent Document 2 has an engaging shape capable of engaging with a female member. The engaging shape is provided so that the male member is drawn from the female member and stored in the cover, and then the cover is separated from the female member. In contrast thereto, in the present embodiment, the position of the cover 90 is substantially fixed with respect to the plug 186 when the puncture needle 20 is drawn from the plug 186, as described above. Accordingly, the cover 90 of the present embodiment does not need to have an engaging shape capable of engaging with the vial bottle 180 that is similar to the engaging shape of the cover of Patent Document 2. The vial bottle 180 does not originally have a structure with which the engaging shape of the cover of Patent Document 2 can engage. In Patent Document 2, in order for the engaging shape to engage with a plurality of female members having different specifications, it is necessary to prepare a plurality of covers having different engaging shapes that correspond to the specifications of female members. In the preferred embodiment of the present invention, the cover 90 does not need to have such an engaging shape, and thus it is not necessary to prepare a plurality of types of covers 90 that correspond to the specifications of female members. According to the connector 1 of the present embodiment, it is possible to reduce the likelihood of a drug solution leaking to the outside also from a vial bottle 180 that does not have a shape with which the engaging shape engages.

The preferred embodiment of the present invention has a configuration in which, in the state in which the claws 66 and 76 are engaged with the flange 182, the projection surface 97 at the tip of the cover 90 abuts against the upper surface of the plug 186. Accordingly, the projection surface 97 of the cover 90 continues to abut against the plug 186 even after the puncture needle 20 has been drawn from the plug 186, as long as the claws 66 and 76 are engaged with the flange 182. Accordingly, the opening, on the tip 20t side, of the liquid flow channel 21 of the puncture needle 20 drawn from the plug 186 can be reliably stored in the cover 90 without being exposed to the outside. Accordingly, it is possible to further reduce the likelihood of a drug solution leaking to the outside after the connector 1 and the vial bottle 180 are separated from each other.

There are cases where a hole of the plug 186 that was made by the puncture of the puncture needle 20 is not yet completely closed immediately after the puncture needle 20 is drawn. In such cases, a situation may occur in which a drug solution leaks to the outside via the hole. However, in the preferred embodiment of the present invention, the projection surface 97 of the cover 90 continues to be in intimate contact with the plug 186 even after the puncture needle 20 is drawn from the plug 186, as long as the claws 66 and 76 are engaged with the flange 182. The hole of the plug 186 that was made by the puncture of the puncture needle 20 is closed by the projection surface 97 being in intimate contact with the hole for a while until the hole is closed by the self-recovering force of the plug 186. Accordingly, thereafter, even when the cover 90 is separated from the plug 186, it is possible to reduce the likelihood of a drug solution leaking from the plug 186.

In the preferred embodiment of the present invention, the "lock mechanism" for preventing disengagement between the claws 66, 76 and the flange 182 is provided. In the "locked state" in which the lock mechanism functions, the flange 182 of the vial bottle 180 and the claws 66 and 76 cannot be disengaged. In the "unlocked state" in which the lock mechanism does not function, the claws 66 and 76 can engage with the flange 182 of the vial bottle 180, and the flange 182 and the claws 66, 76 can disengage from each other.

The locked state and the unlocked state are switched based on the position, in the longitudinal direction of the puncture needle 20, of the slider 50 with respect to the connector main body 10. Accordingly, in the process in which the puncture needle 20 punctures the plug 186, a configuration is possible in which the lock mechanism automatically switches from the unlocked state to the locked state at the same time as when the slider 50 and the vial bottle 180 are advanced into the connector main body 10. In this case, no effort is needed for manually switching to the locked state. The switching of the lock mechanism from the unlocked state to the locked state is reliably performed without being forgotten. For example, in the punctured state (see FIG. 22), if the lock mechanism is not switched to the locked state, an erroneous operation may occur in which the claws 66, 76 and the flange 182 are disengaged and the vial bottle 180 is separated from the connector 1. In this case, a drug solution will leak to the outside from the opening, on the tip 20t side, of the liquid flow channel 21 of the puncture needle 20. In contrast, in the preferred embodiment of the present invention, since the locked state and the unlocked state are switched based on the position of the slider 50 with respect to the connector main body 10, the above-described erroneous operation that is caused due to the lock mechanism not being switched to the locked state is not likely to occur. Accordingly, safety is improved.

The "unlocked position" refers to the position of the slider 50 with respect to the connector main body 10 at which the lock mechanism is in the unlocked state. In the preferred embodiment of the present invention, the unlocked position corresponds to the position of the slider 50 in the state in which the slider 50 is drawn, to the maximum, out of the connector main body 10, that is, (1) the "initial state" (FIGS. 11A, 11B, 12A, 12B, and 13), (2) the state immediately after the claws 66 and 76 are engaged with the vial bottle 180 (FIG. 19), and (3) the state in which the slider 50 is drawn out of the connector main body 10 beyond the intermediate stop position (FIGS. 27 and 28). Since switching is performed from the locked state to the unlocked state by drawing the slider 50, to the maximum, out of the connector main body 10, only moving the vial bottle 180 in the punctured state (FIGS. 21 and 22) away from the connector main body 10 leads to the state in which the connector 1 and the vial bottle 180 can be separated from each other. Accordingly, the operation of separating the connector 1 from the vial bottle 180 is simplified, and it is easy for a non-skilled person to understand the separating operation.

In the preferred embodiment of the present invention, when the slider 50 is at the unlocked position, the opening, on the tip 20t side, of the liquid flow channel 21 of the puncture needle 20 is covered by the cover 90. Accordingly, even if the claws 66, 76 and the flange 182 are disengaged when the slider 50 is at the unlocked position, it is possible to prevent the occurrence of a situation in which a drug solution leaks to the outside from the opening, on the tip 20t side, of the liquid flow channel 21.

In the preferred embodiment of the present invention, in the process of drawing the slider 50 in the punctured state (FIGS. 21 and 22) from the connector main body 10 toward the unlocked position (FIGS. 27 and 28), the "intermediate stop position" is provided at a position prior to the unlocked position (FIGS. 23 to 25). At the intermediate stop position, the movement of the slider 50 with respect to the connector main body 10 is restricted in order for the slider 50 to be prevented from being further drawn from the connector main body 10. When the slider has reached the intermediate stop position, an operator needs to press the release button 52 to release the restriction of the movement of the slider 50 with respect to the connector main body 10 (see FIG. 26). With this measure, the slider 50 can be moved further to the unlocked position. When the claws 66, 76 and the flange 182 are disengaged from each other at the unlocked position, the cover 90 and the plug 186 are separated from each other.

In such a preferred embodiment, the operation of separating the connector 1 from the vial bottle 180 is temporarily stopped at the intermediate stop position. At the intermediate stop position, the puncture needle 20 is substantially drawn out of the plug 186, but the cover 90 and the plug 186 are in intimate contact with each other (see FIG. 25). The hole of the plug 186 that was made by the puncture of the puncture needle 20 is closed by the self-recovering force of the plug 186, by a time at which the release button 52 is pressed at the intermediate stop position and the separating operation is restarted. That is, by providing the intermediate stop position, the length of time in which the hole of the plug 186 that the puncture needle 20 has punctured closes is reliably ensured. Accordingly, thereafter, when the cover 90 is separated from the plug 186, it is possible to reduce the likelihood of a drug solution leaking from the plug 186.

In the preferred embodiment of the present invention, the cover 90 includes, on the tip side relative to the seal region 92, the deformable region 93 that can deform relatively easily. In the initial state (FIGS. 13 and 14), the closed space 99 is formed in the deformable region 93. The closed space 99 is reduced (preferably has disappeared) in the punctured state (FIG. 22) in which the puncture needle 20 has punctures the plug 186, but then starts reverting when the slider 50 reaches the unlocked position (FIG. 28), and reverts to the initial state (FIG. 30) when the cover 90 is separated from the plug 186. In the process in which the closed space 99 reverts from the state of having been reduced or having substantially disappeared to the initial state in this way, negative pressure is generated in the closed space 99. In the seal region 92 on the upper side relative to the closed space 99, the inner circumferential surface of the inner cavity 91 of the cover 90 is liquid-tightly and air-tightly in intimate contact with the outer circumferential surface of the puncture needle 20. Accordingly, a drug solution between the projection surface 97 of the cover 90 and the plug 186 is suctioned, with the negative pressure in the closed space 99, into the closed space 99 via the slit 95. For example, when the puncture needle 20 that has punctured the plug 186 is drawn from the plug 186, a drug solution in the vial bottle 180 may be attached to the outer circumferential surface of the puncture needle 20, and may leak out of the plug 186. Furthermore, immediately after the puncture needle 20 is drawn out of the plug 186, the drug solution may leak out of the plug 186 through the hole made by the puncture of the puncture needle 20. Even if a drug solution passes through the plug 186 and leaks to the space between the plug 186 and the projection surface 97 of the cover 90 in this way, the drug solution is suctioned into the closed space 99 with negative pressure generated in the closed space 99. Accordingly, it is possible to reduce the amount of a drug solution that is attached to the projection surface 97 of the cover 90 or the outer surface of the plug 186 after the cover 90 and the plug 186 are separated from each other. Note that in the punctured state (FIG. 22), the closed space 99 does not need to completely disappear. In the punctured state (FIG. 22), even if the closed space 99 is only reduced, negative pressure is then generated in the closed space 99 in the process in which the closed space 99 reverts to the shape of the initial state, and thus the same effects as those described above are achieved.

The deformable region 93 of the cover 90 is relatively easily compressed/stretched in the vertical direction compared to the seal region 92. Accordingly, even if the slider 50 is at any position such as the initial position, the punctured position, the intermediate stop position, and the unlocked position, the deformable region 93 will deform conforming to the deformation of the plug 186. Accordingly, the state in which the projection surface 97 of the cover 90 and the plug 186 are in intimate contact with each other reliably continues to be kept, as long as the claws 66 and 76 are engaged with the flange 182. Accordingly, the negative pressure generated in the closed space 99 does not return to normal pressure unless intended. Moreover, the projection surface 97 of the cover 90 prevents a drug solution from leaking to the outside through the hole of the plug 186 that was made by the puncture of the puncture needle 20. Accordingly, the fact that the deformable region 93 is relatively easily compressed/stretched is advantageous for reducing the amount of a drug solution that is attached to the projection surface 97 of the cover 90 and the outer surface of the plug 186 after the cover 90 and the plug 186 are separated from each other.

Due to, for example, a variation in the size in the vertical direction of plugs 186 or flanges 182, the height of the upper surface of the plug 186 when the connector 1 is mounted to the vial bottle 180 may be different between vial bottles 180. The amount of compression/stretching of the deformable region 93 may change appropriately according to the difference in the height of the upper surface of the plug 186. Accordingly, the projection surface 97 of the cover 90 is always brought into intimate contact with plugs 186 of vial bottles 180 even if they have different sizes, and the negative pressure can reliably be generated in the closed space 99. Accordingly, the fact that the deformable region 93 is relatively easily compressed/stretched is advantageous for reducing the amount of a drug solution leaking to the outside, for vial bottles 180 having different sizes.

In the preferred embodiment of the present invention, the hold portion 98 that is held by the slider 50 is provided in the seal region 92. The cover 90 does not substantially have a compressible/stretchable region between the hold portion 98 and the seal region 92. Therefore, the position, in the vertical direction, of the seal region 92 with respect to the hold portion 98 is substantially fixed regardless of the position of the slider 50 with respect to the connector main body 10. Accordingly, when the puncture needle 20 is drawn from the plug 186, the seal region 92 of the cover 90, together with the slider 50 and the vial bottle 180, moves relative to the puncture needle 20. As a result, the opening, on the tip 20t side, of the liquid flow channel 21 of the puncture needle 20 drawn from the plug 186 can be stored in the cover 90 without being exposed to the outside, and the opening of the liquid flow channel 21 can be closed by the seal region 92. Accordingly, it is possible to further reduce the likelihood of a drug solution leaking after the connector 1 and the vial bottle 180 are separated from each other.

Furthermore, since the hold portion 98 is provided in the seal region 92, in the state in which the claws 66 and 76 are engaged with the flange 182, the deformable region 93, which is arranged on the tip side relative to the seal region 92, selectively deforms and the projection surface 97 of the cover 90 and the plug 186 get in intimate contact with each other. Therefore, it is possible to reduce the amount of a drug solution that is attached to the projection surface 97 of the cover 90 and the outer surface of the plug 186 after the cover 90 and the plug 186 are separated from each other.

The hold portion 98 of the cover 90 may be compressed by the holder 58 in the diameter direction. In the preferred embodiment of the present invention, the hold portion 98 is provided on the outer circumferential surface of the seal region 92, and thus a compression force in the diameter direction improves intimate contact between the cover 90 and the puncture needle 20 in the seal region 92. This is advantageous for generation of negative pressure in the closed space 99. Accordingly, it is possible to further reduce the amount of a drug solution that is attached to the projection surface 97 of the cover 90 and the outer surface of the plug 186 after the cover 90 and the plug 186 are separated from each other. Furthermore, this is advantageous for improving sealing of the opening, on the tip 20t side, of the liquid flow channel 21. Accordingly, it is possible to further reduce the leakage of a drug solution to the outside.

4. Various Modified Embodiments

Foregoing Embodiment 1 is merely an example. The present invention is not limited to foregoing Embodiment 1, and may be modified appropriately.

For example, the shape of the puncture needle 20 is not limited to the above-described shape, and may be modified appropriately. The lateral hole 21a does not need to extend perpendicularly to the central axis 1a (that is, in the radial direction), and may extend along the straight line that is inclined with respect to the central axis 1a. The gas flow channel 22 may have a lateral hole similar to the lateral hole 21a. A configuration is also possible in which the lateral hole 21a is omitted, and the liquid flow channel 21 extends along the central axis 1a and opens in the outer circumferential surface of the conical portion 25, as with the gas flow channel 22. Also in this case, in the initial state, the shape of the inner circumferential surface of the inner cavity 91 is preferably set so that the opening of the liquid flow channel 21 is closed by the inner circumferential surface of the inner cavity 91 in the seal region 92 of the cover 90.

Also the rear upper frame 78 of the slider 50 may be provided with a release button 52. That is, it is possible to make the configuration of the front-side openings 31 and 61 and the vicinity thereof and the configuration of the rear-side openings 41 and 61 and the vicinity thereof substantially the same. In this case, by simultaneously pressing the front and rear release buttons when the slider 50 is at the intermediate stop position, it is possible to further move the slider 50 to the unlocked position.

In the connector main body 10, the rear-side opening 41 may be omitted. In this case, the rear-side restricting arm 72 of the slider 50 can be omitted.

The number of claws that are to engage with the flange 182 is not limited to four as in Embodiment 1. A larger or smaller number of claws may be provided.

A configuration is also possible in which the intermediate stop position of the slider 50 is omitted, and the slider 50 may be movable relative to the connector main body 10 from the punctured position to the unlocked position without the movement of the slider 50 being stopped along the way.

The lock mechanism may be omitted. For example, by appropriately setting the bending strengths of the grip arms 65 and 75, it is possible to reduce the likelihood of the claws 66, 76 and the flange 182 of the vial bottle 180 unintentionally disengaging, even without the lock mechanism.

The shape of the cover 90 may be changed appropriately. The movable portion 93a that is formed in the deformable region 93 may have any shape. The deformable region 93 may have an accordion shape such that the outer diameter and the inner diameter thereof periodically change in the vertical direction, so as to be easily compressed/stretched. The hold portion 98 does not need to have the largest outer diameter of the cover 90, and may have any shape that can be held stably by the slider 50. The deformable region 93 does not need to be adjacent to the seal region 92. For example, there may exist, between the deformable region 93 and the seal region 92, a region (intermediate region) that is relatively difficult to be made subject to compression deformation and stretching deformation compared to the deformable region 93, and that is not brought into intimate contact with the outer circumferential surface of the puncture needle 20 in the initial state (see FIG. 14).

The connector 1 of foregoing Embodiment 1 may be replaced by the "second connector 200" of Patent Document 1 (see FIGS. 11 and 14 of Patent Document 1), and may constitute the closed system device of Patent Document 1. Note that the connector of the present invention is applicable to devices other than the closed system device of Patent Document 1. The configuration of the portion on the upper side relative to the top board 11 of the connector main body 10 may be changed suitably.

Embodiment 2

A connector 2 according to Embodiment 2 differs from the connector 1 of Embodiment 1 mainly in a cover and a holder for holding it. Hereinafter, the connector 2 of Embodiment 2 will be described based mainly on the differences from Embodiment 1. In the drawings illustrating the connector 2 of Embodiment 2, the same reference numerals are given to members or elements that correspond to members or elements that constitute the connector 1 of Embodiment 1, and descriptions thereof are omitted.

Figure 31A:
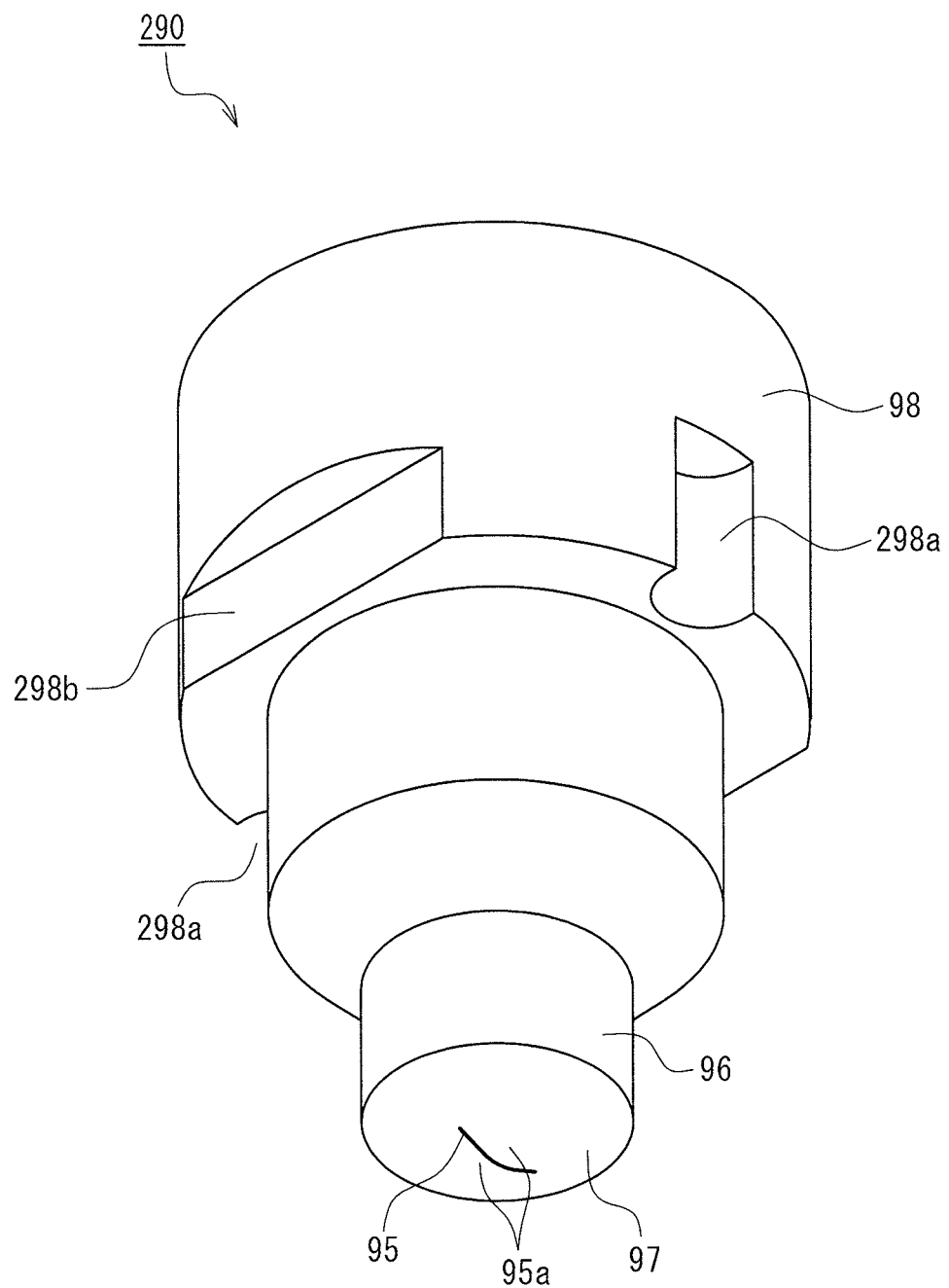
FIG. 31A is a perspective view of a male member cover according to Embodiment 2 of the present invention, the male member cover being seen from below.
Figure 31B:
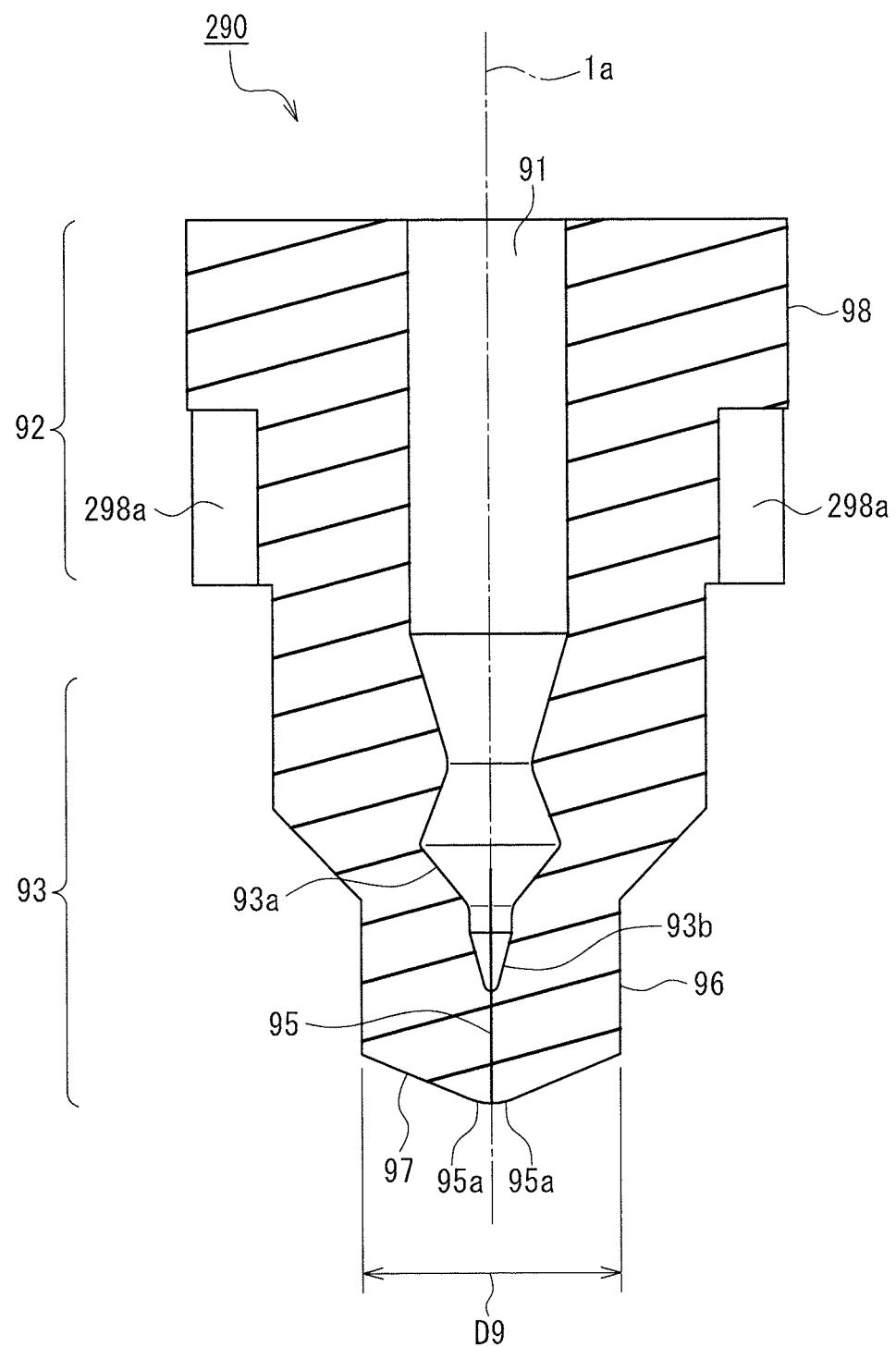
FIG. 31B is a cross-sectional view of the male member cover according to Embodiment 2 of the present invention.

FIG. 31A is a perspective view of a male member cover 290 according to Embodiment 2 of the present invention (hereinafter, referred to simply as "cover") that is seen from below, and FIG. 31B is a cross-sectional view of the cover 290.

Similar to the cover 90 of Embodiment 1, a cover 290 of Embodiment 2 is provided with the seal region 92 on the upper side (base end side), and a deformable region 93 on the lower side (tip side). A hold portion 98 for use for the cover 290 to be held is provided in the seal region 92.

In contrast to the cover 90 of Embodiment 1, the hold portion 98 of the cover 290 has, on the outer circumferential surface thereof, a pair of first recess portions 298a and a pair of second recess portions 298b. When seen from below, the pair of first recess portions 298a are opposite to each other in a direction in which a pair of edges (lips) 95a forming a linear slit 95 are opposite to each other, and the pair of second recess portions 298b are opposite to each other in a direction orthogonal to the direction in which the pair of edges 95a are opposite to each other. All of the first recess portions 298a and the second recess portions 298b are cutouts extending upward from the lower end on the outer circumferential surface of the hold portion 98 by a predetermined length. The first recess portions 298a have an inner surface of a cylindrical surface shape, and the second recess portions 298b are flat faced.

The cover 290 of Embodiment 2 is the same as the cover 90 of Embodiment 1 except for the above description.

Figure 32A:
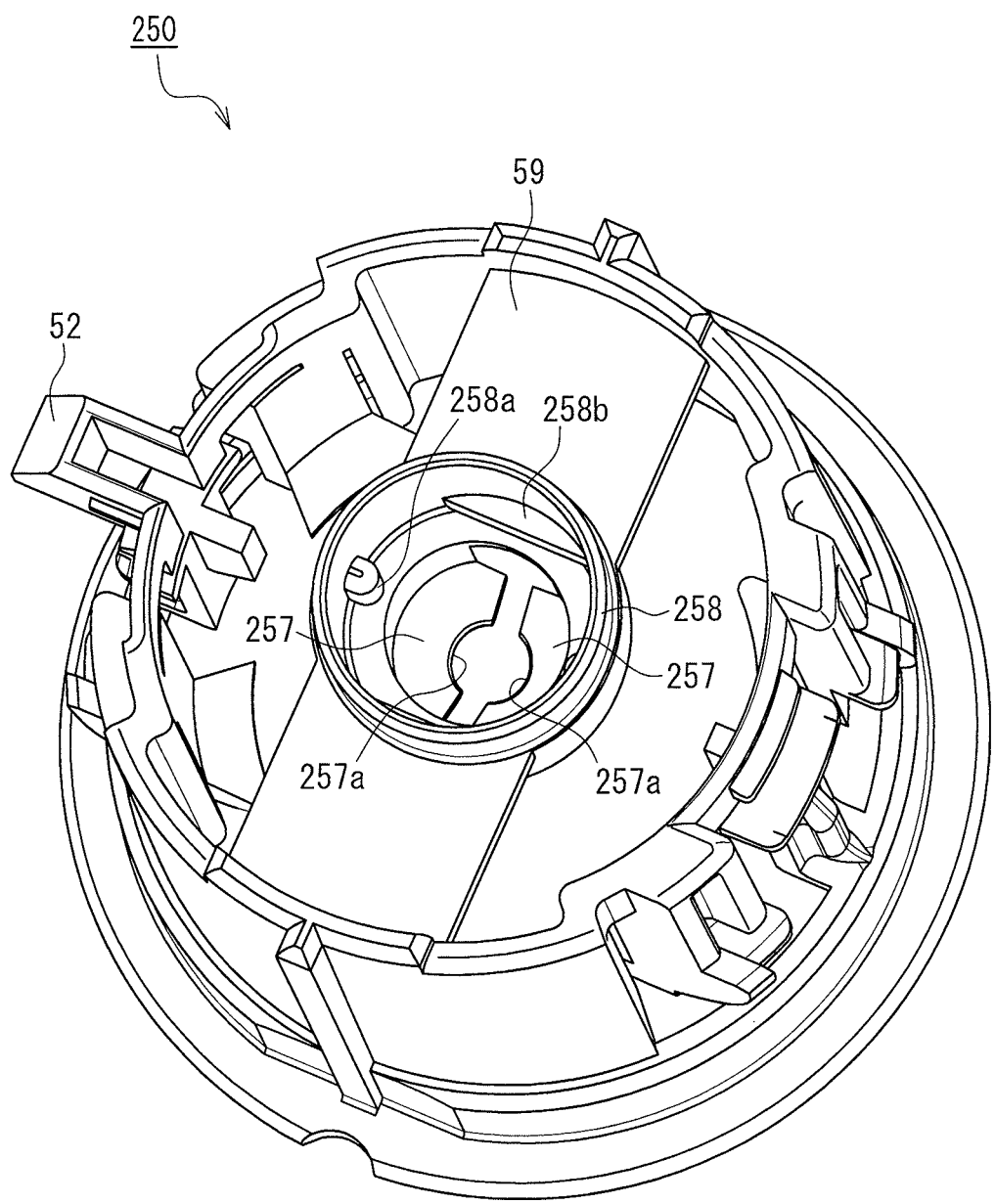
FIG. 32A is a perspective view of a slider that constitutes a connector according to Embodiment 2 of the present invention, the slider being seen from above.
Figure 32B:
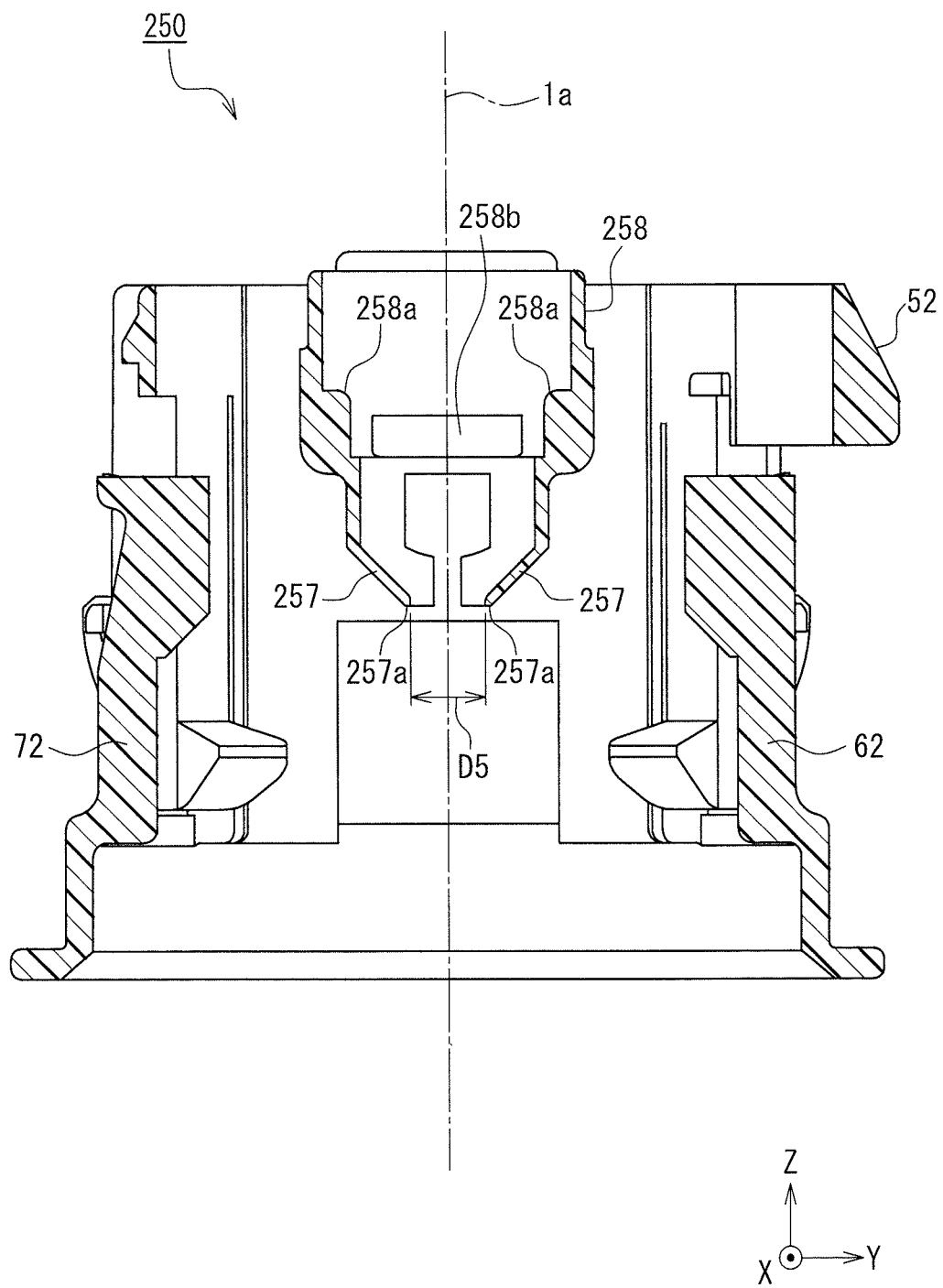
FIG. 32B is a cross-sectional view of the slider that constitutes the connector according to Embodiment 2 of the present invention.

FIG. 32A is a perspective view of a slider 250 constituting the connector 2 of Embodiment 2 that is seen from above, and FIG. 32B is a cross-sectional view of the slider 250. The cross section of FIG. 32B includes the central axis 1a of the connector 2 and the Y axis. The slider 250 is provided with a holder 258 that has a substantially cylindrical shape, and opens in the vertical direction. The holder 258 is fixed to the inner circumferential surface of the slider 250 via a holding bar 59 that is parallel to the X axis so as to be coaxial with the central axis 1a.

A pair of first projection portions 258a and a pair of second projection portions 258b (only one of the second projection portions 258b is shown in FIG. 32B) project toward the central axis 1a from the inner circumferential surface of the holder 258. The pair of first projection portions 258a are opposite to each other in the Y axis direction, and the pair of second projection portions 258b are opposite to each other in the X axis direction. The first projection portions 258a are projections that have a shape of a cylindrical surface extending parallel to the central axis 1a so as to be fitted to the first recess portions 298a (see FIG. 31A) of the cover 290. The second projection portions 258b have a plane parallel to the YZ surface so as to be fitted to the second recess portion 298b (see FIG. 31A) of the cover 290.

A pair of side walls 257 extend downward from the lower end of the holder 258. The pair of side walls 257 are opposite to each other in the Y axis direction. The opposing inner surfaces of the pair of side walls 257 are configured to conform to the outer circumferential surface of the deformable region 93 of the cover 290. Tips (lower ends) 257a of the side walls 257 substantially conform to an arc that is coaxial with the central axis 1a. A maximum inner dimension D5 (see FIG. 32B) between the tips 257a of the pair of side walls 257 in the direction (Y axis direction) in which the pair of side walls 257 are opposite to each other is slightly smaller than an outer diameter D9 (see FIG. 31A) of a tubular portion 96 that encloses a projection surface 97 of the cover 290. The side walls 257 have a cantilever support structure in which their upper ends (portions connected to the lower end of the holder 258) are fixed ends, and the tips 257a are free ends. The side walls 257 are elastically bendable and deformable in the Y axis direction in which their tips (free ends) 257a move away from the central axis 1a.

Figure 33:
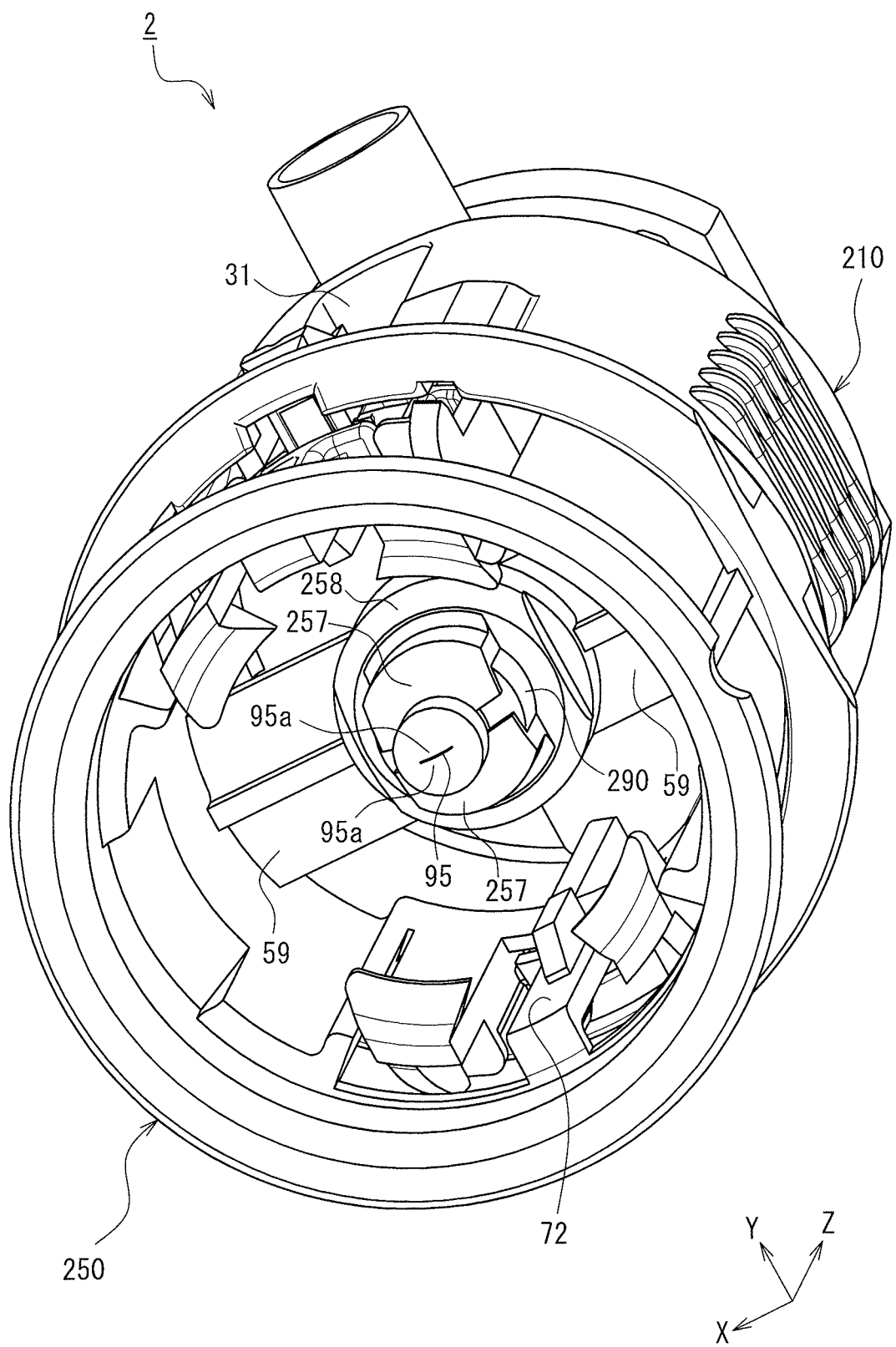
FIG. 33 is a perspective view of the connector according to Embodiment 2 of the present invention in an initial state, the connector being seen from the lower side.
Figure 34:
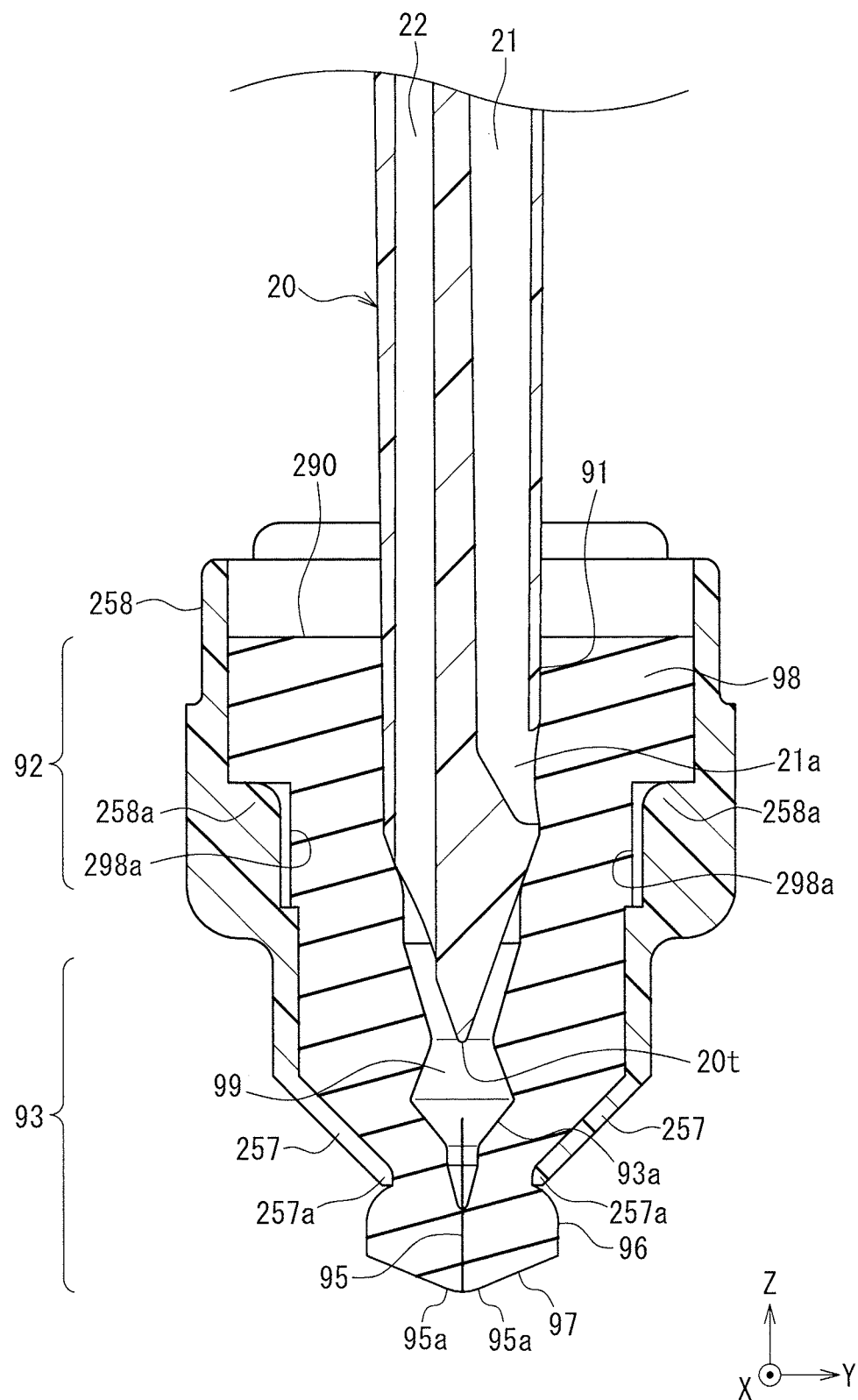
FIG. 34 is an enlarged cross-sectional view of the tip of a puncture needle of the connector according to Embodiment 2 of the present invention in the initial state, and a cover thereof that covers the puncture needle.

The cover 290 is stored in the holder 258 from an upward directed opening of the holder 258. Similar to Embodiment 1, the slider 250 provided with the cover 290 is inserted into the connector main body 210, and thereby the connector 2 of Embodiment 2 is assembled. FIG. 33 is a perspective view of the connector 2 in the initial state that is seen from below, and FIG. 34 is an enlarged cross-sectional view of the tip 20t of the puncture needle 20 and a cover 290 that covers it, according to the connector 2 in the initial state. Although not shown, the cover 290 is preferably fixed to the holder 258 so that the cover 290 does not move toward the holder 258 in the vertical direction. The fixing method is not limited, and it is possible to use a method for applying an adhesive agent, a method for heating the upper end of the holder 258 to fold it over the upper surface of the cover 290, or the like.

As described above, the hold portion 98 of the cover 290 has the pair of first recess portions 298a and the pair of second recess portions 298b (see FIG. 31A), and the holder 258 of the slider 250 has the pair of first projection portions 258a and the pair of second projection portions 258b (see FIGS. 32A and 32B). When the hold portion 98 is stored in the holder 258, the first recess portions 298a and the first projection portions 258a are fitted to each other, and the second recess portions 298b and the second projection portions 258b are fitted to each other. Accordingly, the position of the holder 258 in the direction of rotation about the central axis 1a of the cover 290 is defined. That is, as shown in FIG. 33, the cover 290 is held by the holder 258 so that the longitudinal direction of the linear slit 95 is orthogonal to the direction (Y axis direction) in which the pair of side walls 257 are opposite to each other.

The tips 257a of the side walls 257 are opposite to the tubular portion 96 provided in the deformable region 93 of the cover 290. The tubular portion 96 and the projection surface 97 of the cover 290 protrude downward from the tips 257a of the side walls 257. As described above, the maximum inner dimension D5, in the Y axis direction, between the tips 257a of the side walls 257 is slightly smaller than the outer diameter D9 of the tubular portion 96 of the cover 290. Accordingly, as is easily understandable from FIG. 34, the tips 257a of the pair of side walls 257 compress the tubular portion 96 of the cover 290 in the Y axis direction. Since the direction in which the pair of side walls 257 are opposite to each other matches the direction in which the pair of edges 95a constituting the slit 95 are opposite to each other, a compression force of the tips 257a of the side walls 257 acts so as to bring the pair of edges 95a of the slit 95 in intimate contact with each other.

The connector 2 is the same as the connector 1 of Embodiment 1 except for the above description, and can be used in the same manner as the connector 1 of Embodiment 1.

In the connector 2 of Embodiment 2, the side walls 257 (particularly, the tips 257a thereof) improve the intimate contact between the pair of edges 95a of the slit 95. This is advantageous for improving the sealing property of the slit 95. In the connector 1 of Embodiment 1 that does not have the side walls 257, once the puncture needle 20 has penetrated the slit 95, the sealing property of the slit 95 may deteriorate. In contrast, Embodiment 2 is particularly advantageous for improving the sealing property (that is, re-sealing property) of the slit 95 after the puncture needle 20 is drawn.

Similar to the description of Embodiment 1, also in Embodiment 2, the closed space 99 in the deformable region 93 of the cover 290 is at its smallest in the punctured state (see FIG. 22), and then reverts to the initial state (FIG. 34) when the cover 290 was separated from the plug 186 of the vial bottle 180. In this process, negative pressure is generated in the closed space 99, and thus a drug solution between the cover 290 and the plug 186 is suctioned into the closed space 99 via the slit 95. In Embodiment 2, the side walls 257 improve the re-sealing property of the slit 95, and thus the likelihood of a drug solution stored in the closed space 99 leaking to the outside through the slit 95 is reduced. Accordingly, it is possible to reduce the amount of a drug solution that is attached to the projection surface 97 of the cover 290 after the cover 290 and the plug 186 are separated from each other, as compared to Embodiment 1.

Since the tips 257a of the side walls 257 locally compress the tubular portion 96 of the cover 290, it is possible to efficiently improve the sealing property of the slit 95.

The side walls 257 have a cantilever support structure, and are elastically bendable and deformable. Accordingly, the side walls 257 bend and deform according to a change in the outer diameter of the cover 290 (particularly, the tubular portion 96).

When the diameter of the tubular portion 96 of the cover 290 increases due to, for example, the puncture needle 20 penetrating the slit 95, the side walls 257 elastically bend and deform so that the tips 257a of the opposing side walls 257 move away from each other. Therefore, the side walls 257 neither plastically deform nor break. Furthermore, the cover 290 is not damaged by being compressed by the puncture needle 20 and the tips 257a of the side walls 257 in the radial direction. Furthermore, an increase, due to the provision of the side walls 257, in resistance when the puncture needle 20 penetrates the slit 95 is small.

Thereafter, when the puncture needle 20 that has penetrated the slit 95 is stored in the seal region 92, the diameter of the tubular portion 96 is reduced to the initial state, and also the side walls 257 revert to the initial state in accordance with the reduction of the diameter (see FIG. 34). Because the tips 257a of the side walls 257 always compress the tubular portion 96, the side walls 257 can immediately reduce the diameter of the tubular portion 96 even when the puncture needle 20 is quickly drawn from the slit 95. Accordingly, the likelihood of a drug solution leaking to the outside through the slit 95 is low.

Even when the puncture needle 20 is drawn and inserted from and into the slit 95 repeatedly, the function of the side walls 257 does not deteriorate, and thus the re-sealing property of the slit 95 is not reduced.

The cover 290 and the holder 258 have engaging shapes that engage with each other (the recess portions 298a and 298b, and the projection portions 258a and 258b). Accordingly, when the cover 290 is mounted to the slider 250, it is easy to perform the operation of positioning the cover 290 with respect to the slider 250 in the direction of rotation about the central axis 1a. Furthermore, during use of the connector 2, the cover 290 does not rotate about the central axis 1a with respect to the slider 250. Therefore, the side walls 257 always compress the cover 290 so as to bring the pair of edges 95a of the slit 95 into intimate contact with each other. It is thus possible to stably achieve the excellent sealing property (re-sealing property) of the slit 95. Note that the engaging shapes of the cover 290 and the holder 258 and number thereof are not limited to those of the example of Embodiment 2, and may be changed suitably. The engaging shapes are not limited to projection portions and recess portions as in the above-described example. For example, it is also possible to configure the engaging shapes by defining the outer circumferential surface of the hold portion 98 and the inner circumferential surface of the holder 258 as columnar surfaces that engage with each other and that have a shape such as an ellipse, rectangle, or rhomboid when seen from above.

As described in Embodiment 1, also in Embodiment 2, the position of the cover 290 with respect to the plug 186 is fixed regardless of whether or not the puncture needle 20 has penetrated the plug 186, as long as the claws 66 and 67 of the slider 250 are engaged with the vial bottle 180. Therefore, the side walls 257 can be extended to the vicinity of the slit 95. In Embodiment 2, the tips 257a of the side walls 257 reach the tubular portion 96 provided in the deformable region 93 of the cover 290. Even when the tips 257a of the side walls 257 are arranged in the vicinity of the slit 95 in this manner, the side walls 257 do not collide with the plug 186 of the vial bottle 180. The side walls 257 of Embodiment 2 can achieve an effect of improving the sealing property of the slit 95 particularly significantly when it is applied to the connector 2 in which the slider 250 to which the cover 290 is mounted is movable with respect to the connector main body 210 provided with the puncture needle 20.

The shape of the tips 257a of the side walls 257 does not need to be an arc-shape as with the above-described example. For example, the tips 257a of the side walls 257 may have a shape of a straight line that is parallel to the longitudinal direction (X axis direction) of the slit 95.

The portion on the upper side relative to the tips 257a of the side walls 257 may be distanced from the cover 290 so as not to come in contact with the outer circumferential surface of the cover 290.

Embodiment 2 is the same as Embodiment 1 except for the above description. The description of Embodiment 1 is also applied to Embodiment 2.

In Embodiments 1 and 2 above, the vial bottle 180 serves as a female member, and the puncture needle 20 provided with a sharp tip capable of puncturing the plug 186 of the vial bottle 180 serves as a male member. However, the present invention is not limited to this. As described in Patent Document 2, a needle-less port provided with a partition wall member in which a linear slit (incision) si formed and that is made of an elastic material such as a rubber may serve as a female member. Furthermore, a rod-shaped male luer that is to be inserted into the slit of the partition wall member may serve as a male member. In this case, only a single flow channel through which liquid flows may be formed in the male luer. The cover of the present invention may cover an opening, on the tip side, of the flow channel of the male luer in the initial state.

INDUSTRIAL APPLICABILITY

The field of use of the present invention is not limited, and the present invention can be used preferably in the medical field in which a dangerous medicine is handled.

DESCRIPTION OF REFERENCE NUMERALS 1, 2 Connector (drug container connector)
1a Central axis of connector
10, 210 Connector main body
20 Puncture needle
20t Tip of puncture needle
21 Liquid flow channel
21a Lateral hole of liquid flow channel
22 Gas flow channel
50, 250 Slider
52 Release button
62, 72 Restricting arm (slide restricting arm)
64, 74 Abutting protrusion
64a, 74a Edge of abutting protrusion 65, 75 Grip arm
66, 76 Claw
90, 290 Cover
92 Seal region
93 Deformable region
95 Slit
95a Edge (lip) of slit
97 Tip (projection surface) of cover
98 Hold portion
99 Closed space
180 Vial bottle (container)
182 Flange
183 Mouth of vial bottle
186 Plug
188b Upper edge of plug (cap)
257 Side wall
257a Tip of side wall
258 Holder
258a, 258b Projection portion (engaging shape)
298a, 298b Recess portion (engaging shape)

The invention claimed is:

1. A drug container connector comprising:
a puncture needle capable of puncturing a plug that seals a mouth of a container; and
a cover that covers an opening, on a tip side, of a flow channel through which liquid flows and that is formed in the puncture needle, the puncture needle being configured to penetrate the cover and puncture the plug,
wherein the puncture needle is provided on a connector main body,
the cover is held by a slider,
the slider is movable with respect to the connector main body in a reciprocating manner along a longitudinal direction of the puncture needle between an initial position at which the slider is drawn to a maximum extent from the connector main body and a punctured position at which the slider is stored in the connector main body,
the slider is provided with a claw capable of engaging with a flange at the mouth of the container
the connector includes an intermediate stop position partway from the initial position to the punctured position,
when the slider is moved toward the initial position from a punctured state in which the puncture needle punctures the plug and the claw is engaged with the flange and the slider is at the punctured position, the slider collides with the connector main body in the longitudinal direction of the puncture needle at the intermediate stop position so as to restrict movement of the slider with respect to the connector main body toward the initial position, and
the intermediate stop position is positioned such that a hole in the plug formed by the puncture needle is able to close by a self-recovering force of the plug when the slider is stopped at the intermediate stop position.

2. The drug container connector according to claim 1, wherein the drug container connector is configured such that a tip of the cover abuts against the plug in a state in which the claw is engaged with the flange of the container.

3. The drug container connector according to claim 1, further comprising:
a lock mechanism for preventing disengagement between the claw and the flange.

4. The drug container connector according to claim 3, wherein the lock mechanism includes: a grip arm on which the claw is formed and that can elastically bend and deform outwardly; and the connector main body for restricting bending and deformation of the grip arm.

5. The drug container connector according to claim 3, wherein a locked state and an unlocked state of the lock mechanism can be switched based on a position of the slider with respect to the connector main body in the longitudinal direction of the puncture needle.

6. The drug container connector according to claim 3, wherein the lock mechanism does not function when the slider is drawn, to the maximum, from the connector main body.

7. The drug container connector according to claim 1, further comprising:
a release button for releasing the restriction of the movement of the slider with respect to the connector main body at the intermediate stop position.

8. The drug container connector according to claim 3, wherein the opening of the puncture needle is covered by the cover when the slider is located at an unlocked position at which the lock mechanism does not function.

9. The drug container connector according to claim 1, wherein the slider cannot move with respect to the connector main body in the longitudinal direction of the puncture needle when the claw is not engaged with the flange of the container.

10. The drug container connector according to claim 1, wherein the slider can move with respect to the connector main body in the longitudinal direction of the puncture needle when the claw is engaged with the flange of the container.

11. The drug container connector according to claim 1, wherein the slider includes: an abutting protrusion that abuts against an upper edge of the plug when the claw is engaged with the flange of the container; and a slide restricting arm on which the abutting protrusion is formed and that can elastically bend and deform outwardly.

12. The drug container connector according to claim 11, wherein, when the claw is not engaged with the flange of the container, the slide restricting arm collides with the connector main body, so as to restrict the slider from moving with respect to the connector main body in the longitudinal direction of the puncture needle, and
when the claw is engaged with the flange of the container, the slide restricting arm elastically bends and deforms to a position at which the slide restricting arm does not collide with the connector main body, so as to enable the slider to move with respect to the connector main body in the longitudinal direction of the puncture needle.

13. The drug container connector according to claim 11, wherein the edge of the abutting protrusion that abuts against the plug is inclined with respect to the longitudinal direction of the puncture needle.

14. The drug container connector according to claim 1, wherein the cover is provided with: a slit through which the puncture needle can penetrate and that is provided at a tip of the cover; a seal region that is in intimate contact with an outer circumferential surface of the puncture needle; and a deformable region that is arranged on a tip side relative to the seal region, and
the deformable region is more easily subjected to compression deformation and stretching deformation in the longitudinal direction of the puncture needle than the seal region.

15. The drug container connector according to claim 14, wherein a closed space is formed in the deformable region when the claw is not engaged with the flange of the container.

16. The drug container connector according to claim 15, wherein the closed space is reduced or has disappeared when the puncture needle has penetrated the plug.

17. The drug container connector according to claim 14, wherein the cover includes a hold portion that is used for the cover to be held to the slider, and
the hold portion is provided in the seal region.

18. The drug container connector according to claim 1, wherein a tip of the cover that is configured to be penetrated by the puncture needle has a projection surface that projects toward the plug.

19. The drug container connector according to claim 1, wherein the cover does not have an engaging shape to engage with the container.

20. The drug container connector according to claim 14, wherein the slit is a linear incision,
the slider further includes a pair of side walls that are opposite to each other in a direction orthogonal to a longitudinal direction of the slit, and
the pair of side walls compress the deformable region so as to bring a pair of edges forming the slit into intimate contact with each other.

21. The drug container connector according to claim 20, wherein the side walls can elastically bend and deform so that a distance between the pair of side walls increases.

22. The drug container connector according to claim 20, wherein the slider and the cover respectively have engaging shapes that engage with each other so as to define a position of the cover in a direction of rotation about the puncture needle.

* * * * *